(12) United States Patent
Menichincheri et al.

(10) Patent No.: US 8,354,399 B2
(45) Date of Patent: Jan. 15, 2013

(54) SUBSTITUTED INDAZOLE DERIVATIVES ACTIVE AS KINASE INHIBITORS

(75) Inventors: Maria Menichincheri, Milan (IT); Jay Aaron Bertrand, Villa Cortese (IT); Chiara Marchionni, Milan (IT); Marcella Nesi, Saronno (IT); Paolo Orsini, Legnano (IT); Achille Panzeri, Merate (IT)

(73) Assignee: Nerviano Medical Sciences S.R.L., Nerviano (IT)

( * ) Notice: Subject to any disclaimer, the term of this patent is extended or adjusted under 35 U.S.C. 154(b) by 0 days.

(21) Appl. No.: 13/140,208

(22) PCT Filed: Dec. 15, 2009

(86) PCT No.: PCT/EP2009/067206
§ 371 (c)(1),
(2), (4) Date: Jun. 16, 2011

(87) PCT Pub. No.: WO2010/069966
PCT Pub. Date: Jun. 24, 2010

(65) Prior Publication Data
US 2011/0281843 A1    Nov. 17, 2011

(30) Foreign Application Priority Data

Dec. 18, 2008   (EP) ..................................... 08172091

(51) Int. Cl.
| | | |
|---|---|---|
| A61K 31/416 | (2006.01) | |
| A61K 31/496 | (2006.01) | |
| A61K 31/454 | (2006.01) | |
| A61K 31/5377 | (2006.01) | |
| C07D 403/12 | (2006.01) | |
| C07D 401/14 | (2006.01) | |
| C07D 231/56 | (2006.01) | |
| C07D 401/12 | (2006.01) | |
| C07D 413/12 | (2006.01) | |
| C07D 405/14 | (2006.01) | |

(52) U.S. Cl. ......... 514/210.21; 514/254.06; 514/253.09; 514/407; 514/322; 514/234.5; 544/371; 544/364; 544/140; 546/199; 548/362.1

(58) Field of Classification Search ............. 514/210.21, 514/254.06, 253.09, 407, 322, 234.5; 544/371, 544/364, 140; 548/362.1; 546/199; 435/184
See application file for complete search history.

(56) References Cited

FOREIGN PATENT DOCUMENTS
WO      WO 03/028720 A1  *  4/2003

OTHER PUBLICATIONS

Cancer [online], [retrieved on Jul. 6, 2007] Retrieved from the Internet, URL: http://www.nlm.nih.gov/medlineplus/cancer.html.*
Lala et al., Role of nitric oxide in tumor progression: Lessons from experimental tumors, Cancer and Metastasis Reviews (1998), 17, 91-106.*
Golub et al., Molecular Classification of Cancer: Class Discovery and Class Prediction by Gene Expression Monitoring, Science (1999), vol. 286, 531-537.*

* cited by examiner

*Primary Examiner* — Kristin Bianchi
(74) *Attorney, Agent, or Firm* — Scully, Scott, Murphy & Presser, P.C.

(57) ABSTRACT

Substituted indazole derivatives of formula (I) and pharmaceutically acceptable salts thereof, as defined in the specification, process for their preparation and pharmaceutical compositions comprising them are disclosed; the compounds of the invention may be useful in therapy in the treatment of diseases associated with a deregulated protein kinase activity, like cancer.

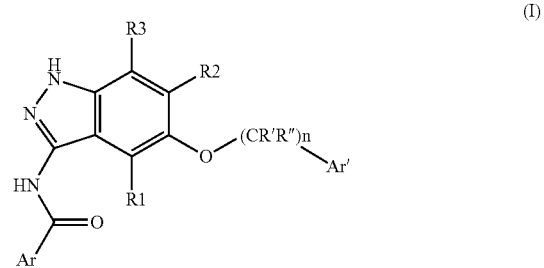

(I)

14 Claims, No Drawings

```
SEQUENCE LISTING

<160> NUMBER OF SEQ ID NOS: 4

<210> SEQ ID NO 1
<211> LENGTH: 76
<212> TYPE: DNA
<213> ORGANISM: Artificial
<220> FEATURE:
<223> OTHER INFORMATION: Forward primer

<400> SEQUENCE: 1
ggggacaagt ttgtacaaaa aagcaggctt actggaagtt ctgttccagg ggccccgccg    60
gaagcaccag gagctg                                                     76

<210> SEQ ID NO 2
<211> LENGTH: 57
<212> TYPE: DNA
<213> ORGANISM: Artificial
<220> FEATURE:
<223> OTHER INFORMATION: Reverse primer

<400> SEQUENCE: 2
ggggaccact ttgtacaaga aagctgggtt tcagggccca ggctggttca tgctatt       57

<210> SEQ ID NO 3
<211> LENGTH: 33
<212> TYPE: DNA
<213> ORGANISM: Artificial
<220> FEATURE:
<223> OTHER INFORMATION: Forward primer

<400> SEQUENCE: 3
ctcggatcca gaaagagaaa taacagcagg ctg                                  33

<210> SEQ ID NO 4
<211> LENGTH: 36
<212> TYPE: DNA
<213> ORGANISM: Artificial
<220> FEATURE:
<223> OTHER INFORMATION: Reverse primer
```

```
<400> SEQUENCE: 4
ctcggatcct cagcaggtcg aagactgggg cagcgg                36
```

SUBSTITUTED INDAZOLE DERIVATIVES ACTIVE AS KINASE INHIBITORS

The present invention relates to certain substituted indazole compounds, which modulate the activity of protein kinases. The compounds of this invention are therefore useful in treating diseases caused by deregulated protein kinase activity. The present invention also provides methods for preparing these compounds, pharmaceutical compositions comprising these compounds, and methods of treating diseases utilizing pharmaceutical compositions comprising these compounds.

The malfunctioning of protein kinases (PKs) is the hallmark of numerous diseases. A large share of the oncogenes and proto-oncogenes involved in human cancers encode for PKs. The enhanced activities of PKs are also implicated in many non-malignant diseases, such as benign prostate hyperplasia, familial adenomatosis, polyposis, neuro-fibromatosis, psoriasis, vascular smooth cell proliferation associated with atherosclerosis, pulmonary fibrosis, arthritis glomerulonephritis and post-surgical stenosis and restenosis.

PKs are also implicated in inflammatory conditions and in the multiplication of viruses and parasites. PKs may also play a major role in the pathogenesis and development of neuro-degenerative disorders.

For a general reference to PKs malfunctioning or deregulation see, for instance, Current Opinion in Chemical Biology 1999, 3, 459-465 and Carcinogenesis 2008, 29, 1087-191.

A subset of PK is a group of membrane receptors with intrinsic protein-tyrosine kinase activity (RPTK). Upon binding of grow factors, RPTKs become activated and phosphorylate themselves and a series of substrates in the cytoplasm. Through this mechanism, they can transduce intracellular signalings for proliferation, differentiation or other biological changes. Structural abnormalities, over-expression and activation of RTPKs are frequently observed in human tumors, suggesting that constitutive ignition of the signal transduction leading to cell proliferation can result in malignant transformation. Anaplastic lymphoma kinase (ALK) is a tyrosine kinase receptor belonging to the insulin receptor subfamily of RTKs: the ALK gene is located on cromosome 2 and is expressed mainly in neuronal cells, especially during development. The ALK gene is involved in a balanced chromosomal translocation with the Nucleophosmin (NPM) gene on cromosome 5 in a large subset of Anaplastic Large Cell Lymphomas (ALCL). In the ALK+ALCL, as a result of the translocation, the NPM ubiquitous promoter drives an ectopic expression of the fusion protein in which the NPM moiety dimerizes and the ALK kinase domain undergoes auto-phosphorylation and becomes constitutively active.

Many data from the literature have demonstrated that the NPM-ALK fusion protein has a strong oncogenic potential and its ectopic expression is responsible for cellular transformation. Moreover, the constitutive expression of human NPM-ALK in mouse T-cell lymphocytes is sufficient for the development of lymphoid neoplasia in transgenic animals with a short period of latency.

ALCL is a defined disease characterized by the surface expression of the CD30 antigen (Ki-1), and accounts for 2% of adult and 13% of pediatric non-Hodgkin's lymphomas, affecting predominantly young male patients. ALK+ ALCL accounts for 70% of all ALCLs and is an aggressive disease with systemic signs, and frequent extranodal involvment (bone marrow, skin, bone, soft tissues).

About 15-20% of ALK-expressing ALCLs were found to bear a different chromosomal translocation, involving the cytoplasmic portion of ALK, with different N-terminal moieties, all resulting in constitutive activation of the ALK kinase domain.

Moreover, cell lines established from solid tumors of ectodermal origin like melanomas, breast carcinomas, as well as neuroblastomas, glioblastomas, Ewings sarcomas, retinoblastomas, were found to express the ALK receptor.

In conclusion, interfering with the ALK signalling likely represents a specific and effective way to block tumor cell proliferation in ALCL and possibly other indications.

The insulin-like growth factor 1 receptor (IGF-1R, IGF1R) is also a member of the insulin receptor subfamily of RTKs. There exist several lines of evidence suggesting that IGF-1R signaling can contribute to tumorigenesis, and that interfering with IGF-1R function represents a valid therapeutic option in cancer. For an overview of IGFs and IGF-1R signalling, physiological function, and detailed description of the evidence supporting involvement of this system in human cancer that is summarised above, as well as in other pathologies, the reader is directed to the many reviews on the subject and references contained therein, for example Baserga R. et al, Biochim Biophys Acta vol. 1332, pages F105-F126, 1997; Khandwala H. M. et al, Endocr Rev vol. 21, pages 215-44, 2000; Le Roith D. et al, Endocr Rev vol. 22, pages 53-74, 2001; Valentinis B. et al, Mol Pathol vol. 54, pages 133-7, 2001; Wang Y. et al, Curr Cancer Drug Targets vol. 2, pages 191-207, 2002; Laron, Z. J Clin Endocrinol Metab vol. 89, pages 1031-1044, 2004; Hofmann Fetal, Drug Discov Today vol. 10, pages 1041-7, 2005.

JAK2 belongs to the Janus family of tyrosine kinases (JAK1, JAK2, JAK3 and TYK2), that are cytoplasmic protein tyrosine kinases that mediate signalling downstream of cytokines and growth factor receptors (Ihle J N. (1995) *Nature* 377: 591-594, Leonard W J and O'Shea J J. (1998). *Annu. Rev. Immunol.*, 16, 293-322). In particular, JAK2 is important for the activity of GM-CSF, IL-3, Thrombopoietin (TPO) and Erythropoietin (EPO). Upon ligand binding, the receptors form oligomers so that the associated JAK kinases can activate each other by transphosphorylation. The effector molecules of JAK kinases, which includes STATs (Signal Transducers and Activators of Transcription), regulate survival, proliferation, differentiation and apoptosis (Bromberg J. (2002). *J. Clin. Invest.*, 109, 1139-1142; Hou S X, et al. (2002. *Dev. Cell* 3, 765-768). Several groups have discovered an activating mutation in the JAK2 gene that appears to be responsible for several different myeloproliferative disorders, in particular Polycythemia Vera (PV), Essential Thrombocythemia (ET) and Idiopathic Myelofibrosis (IM) (Baxter et al., (2005) *Lancet* 365: 1054-1061. James et al., (2005) *Nature* 434: 1144-1148.; Kralovics et al., (2005) *N. Engl. J. Med.* 352: 1779-1790; Levine et al., (2005) *Cancer Cell* 4: 387-397). The mutation of a valine to a phenylalanine at codon 617 (V617F) occurs in the pseudokinase domain of JAK2, that was previously shown to be a negative regulator of the kinase activity of JAK2. In agreement with this finding, JAK2(V617F) behaves as a constitutively activated tyrosine kinase when expressed in cell lines, although its activity may be most pronounced when in association with the EPO receptor. Functional analysis demonstrates that this mutation confers cytokine-independent growth in vitro, deregulates signalling pathways downstream of JAK2, and causes a Polycythemia Vera like disease in a murine model. This mutation is found in most patients with PV (~90%) and in roughly one-half of patients with ET or IM. This mutation could also be identified in other hematological tumors like Chronic MyeloMonocitic Leukemia (3-20%), Philadelphia negative CML (19%), Chronic Neutrophilic Leukemia (16-33%) and others.

Based on the collection of data, JAK-2 kinase activation appears to be the triggering factor for an important group of hematological diseases, thereby suggesting that it could represent a good therapeutic target for the treatment of these pathologies.

Several indazole derivatives useful for the therapy of a variety of diseases such as cancers, neurodegeneration and atherosclerosis have been disclosed in WO2003028720, WO2005085206 and WO2008003396 in the name respectively of Pharmacia Italia spa, Hoffmann La Roche AG and Merck GMBH.

Despite these developments, there is still a need for more effective agents.

We have now discovered that a series of indazoles are potent protein kinase inhibitors and are thus useful in anticancer therapy.

Accordingly, a first object of the present invention is to provide a substituted indazole compound represented by formula (I),

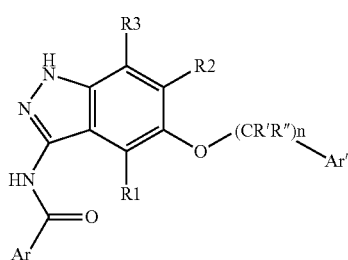

(I)

wherein:
Ar is aryl or heteroaryl substituted with Ra and Rb, wherein
Ra is $NO_2$, $NH_2$, NH-G, N-(E)-G, O-G', $(CH_2)_n$-A or $CH_2$-Hal and
Rb is hydrogen, halogen, $NO_2$, $NH_2$, NH-G, NH—CO-L, O-E or E, wherein
Hal is halogen,
A is optionally substituted heterocyclyl,
E is straight or branched unsubstituted $C_1$-$C_6$alkyl,
G is straight or branched substituted $C_1$-$C_6$ alkyl or an optionally substituted heterocyclyl,
G' is straight or branched $C_1$-$C_6$ alkyl substituted with $N(C_1$-$C_6$ alkyl$)_2$, or an optionally substituted heterocyclyl, and
L is optionally substituted heteroaryl;
Ar' is an optionally substituted aryl or heteroaryl;
R1, R2 and R3 are independently hydrogen, halogen, nitro, an optionally substituted straight or branched $C_1$-$C_6$ alkyl, NR4R5 or OR6, wherein
R4 and R5 are independently hydrogen, alkenyl, alkynyl, R8R9N—$C_2$-$C_6$ alkyl, R8O—$C_2$-$C_6$ an optionally further substituted straight or branched $C_1$-$C_6$ alkyl, $C_3$-$C_6$ cycloalkyl, heterocyclyl, aryl or heteroaryl, or R4 and R5, taken together with the nitrogen atom to which they are bonded, may form an optionally substituted heterocyclyl group;
R6 is hydrogen, alkenyl, alkynyl, COR7, SOR10, $SO_2$R10, R8R9N—$C_2$-$C_6$ alkyl, R8O—$C_6$ alkyl, an optionally further substituted straight or branched $C_1$-$C_6$ alkyl, $C_3$-$C_6$ cycloalkyl, heterocyclyl, aryl or heteroaryl;

R7 is hydrogen, alkenyl, alkynyl, NR4R5, OR6, SR6, R8R9N—$C_1$-$C_6$ alkyl, R8O—$C_1$-$C_6$ alkyl, an optionally further substituted straight or branched $C_1$-$C_6$ alkyl, $C_3$-$C_6$ cycloalkyl, heterocyclyl, aryl or heteroaryl, wherein R4, R5 and R6 are defined as above;
R8 and R9 are independently hydrogen, alkenyl, alkynyl, COR7, an optionally further substituted straight or branched $C_1$-$C_6$ alkyl, $C_3$-$C_6$ cycloalkyl, heterocyclyl, aryl or heteroaryl, or R8 and R9, taken together with the nitrogen atom to which they are bonded, may form an optionally substituted heterocyclyl group, wherein R7 is as defined above;
R10 is hydrogen, alkenyl, alkynyl, NR4R5, OR6, R8R9N—$C_1$-$C_6$ alkyl, R8O—$C_1$-$C_6$ alkyl, an optionally further substituted straight or branched $C_1$-$C_6$ alkyl, $C_3$-$C_6$ cycloalkyl, heterocyclyl, aryl or heteroaryl, wherein R4, R5, R6, R8 and R9 are as defined above;
R' and R" are each independently hydrogen or an optionally substituted straight or branched $C_1$-$C_6$ alkyl;
n is 0 or 1, and
pharmaceutically acceptable salt thereof.

The present invention also provides methods of synthesizing the substituted indazole derivatives of formula (I) prepared through a process consisting of standard synthetic transformations.

The present invention also provides a method for treating diseases caused by and/or associated with deregulated protein kinase activity, particularly PLK family, protein kinase C in different isoforms, Met, PAK-4, PAK-5, ZC-1, STLK-2, DDR-2, Aurora 1, Aurora 2, Bub-1, Chk1, Chk2, HER2, raf1, MEK1, MAPK, EGF-R, PDGF-R, FGF-R, FLT3, JAK2, IGF-R, ALK, PI3K, weel kinase, Src, Abl, Akt, MAPK, ILK, MK-2, IKK-2, Cdc7, Nek, Cdk/cyclin kinase family, more particulary JAK2, IGF-1R and ALK activity, and further more particularly ALK activity, which comprises administering to a mammal in need thereof an effective amount of a substituted indazole compound represented by formula (I) as defined above.

A preferred method of the present invention is to treat a disease caused by and/or associated with dysregulated protein kinase activity selected from the group consisting of cancer and cell proliferative disorders.

Another preferred method of the present invention, is to treat specific types of cancer including carcinoma, squamous cell carcinoma, hematopoietic tumors of myeloid or lymphoid lineage, tumors of mesenchymal origin, tumors of the central and peripheral nervous system, melanoma, seminoma, teratocarcinoma, osteosarcoma, xeroderma pigmentosum, keratocanthomas, thyroid follicular cancer and Kaposi's sarcoma.

Another preferred method of the present invention, is to treat specific types of cancer such as, but not restricted to, breast cancer, lung cancer, colorectal cancer, prostate cancer, ovarian cancer, endometrial cancer, gastric cancer, clear cell renal cell carcinoma, uveal melanoma, multiple myeloma, rhabdomyosarcoma, Ewing's sarcoma, Kaposi's sarcoma, and medulloblastoma.

Another preferred method of the present invention, is to treat ALK+ Anaplastic Large Cell Lymphomas (ALCL) and possibly other indications in which the ALK activity might play a role, like Neuroblastoma, Rhabdomyosarcoma, Glioblastoma, Inflammatory MyofibroblasticTumor, and some kind of Melanomas, Breast Carcinomas, Ewings sarcomas, Retinoblastomas and Non Small Cell Lung Carcinomas (NSCLC).

Another preferred method of the present invention, is to treat cell proliferative disorders such as, but not restricted to, benign prostate hyperplasia, familial adenomatosis polyposis, neuro-fibromatosis, psoriasis, atherosclerosis and conditions involving vascular smooth muscle proliferation or neointimal formation such as restenosis following angioplasty or surgery, pulmonary fibrosis, arthritis, glomerulonephritis, retinopathies including diabetic and neonatal retinopathies and age related macular degeneration, graft vessel disease, such as can occur following vessel or organ transplantation, acromegaly and disorders secondary to acromegaly as well as other hypertrophic conditions in which IGF/IGF-1R signalling is implicated, such as fibrotic lung disease, pathologies related to chronic or acute oxidative stress or hyperoxia induced tissue damage, and metabolic disorders in which elevated IGF levels or IGF-1R activity are implicated, such as obesity.

In addition, the method of the present invention also provides tumor angiogenesis and metastasis inhibition.

In a further preferred embodiment, the method of the present invention further comprises subjecting the mammal in need thereof to a radiation therapy or chemotherapy regimen in combination with at least one cytostatic or cytotoxic agent.

Moreover the invention provides an in-vitro method for inhibiting ALK protein activity which comprises contacting the said protein with an effective amount of a compound of formula (I).

The present invention also provides a pharmaceutical composition comprising one or more compounds of formula (I) or a pharmaceutically acceptable salt thereof and a pharmaceutically acceptable excipient, carrier or diluent.

The present invention further provides a pharmaceutical composition comprising a compound of formula (I) in combination with known anticancer treatments such as radiation therapy or chemotherapy regimen in combination with cytostatic or cytotoxic agents, antibiotic-type agents, alkylating agents, antimetabolite agents, hormonal agents, immunological agents, interferon-type agents, cyclooxygenase inhibitors (e.g. COX-2 inhibitors), matrixmetalloprotease inhibitors, telomerase inhibitors, tyrosine kinase inhibitors, anti-growth factor receptor agents, anti-HER agents, anti-EGFR agents, anti-angiogenesis agents (e.g. angiogenesis inhibitors), farnesyl transferase inhibitors, ras-raf signal transduction pathway inhibitors, cell cycle inhibitors, other cdks inhibitors, tubulin binding agents, topoisomerase I inhibitors, topoisomerase II inhibitors, and the like.

Additionally, the invention provides a product or kit comprising a compound of formula (I) or a pharmaceutically acceptable salt thereof, as defined above, or pharmaceutical compositions thereof and one or more chemotherapeutic agents, as a combined preparation for simultaneous, separate or sequential use in anticancer therapy.

In yet another aspect the invention provides a compound of formula (I) or a pharmaceutically acceptable salt thereof, as defined above, for use as a medicament.

Moreover the invention provides the use of a compound of formula (I) or a pharmaceutically acceptable salt thereof, as defined above, in the manufacture of a medicament with antitumor activity.

Finally, the invention provides a compound of formula (I) or a pharmaceutically acceptable salt thereof, as defined above, for use in a method for treating cancer.

The compounds of formula (I) may have one or more asymmetric centres, and may therefore exist as individual optical isomers or racemic mixtures. Accordingly, all the possible isomers, and their mixtures, of the compounds of formula (I) are within the scope of the present invention.

Derivatives of compounds of formula (I) originating from metabolism in a mammal, and the pharmaceutically acceptable bio-precursors (otherwise referred to as pro-drugs) of the compounds of formula (I) are also within the scope of the present invention.

In addition to the above, as known to those skilled in the art, the unsubstituted nitrogen on the pyrazole ring of the compounds of formula (I) rapidly equilibrates in solution to form a mixture of tautomers, as depicted below:

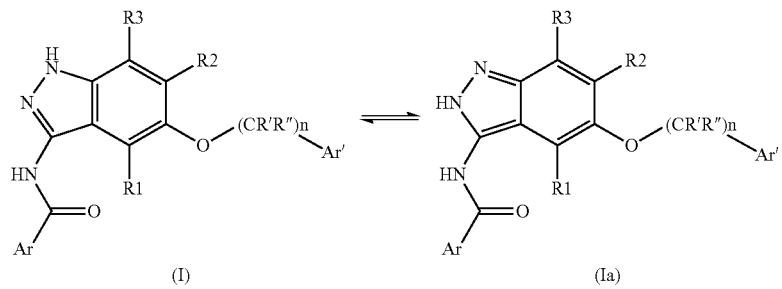

(I)         (Ia)

wherein n, Ar, Ar', R', R", R1, R2 and R3 are as defined above.

Accordingly, in the present invention, where only one tautomer is indicated for the compounds of formula (I), the other tautomer (Ia) is also within the scope of the present invention, unless specifically noted otherwise.

The general terms as used herein, unless otherwise specified, have the meaning reported below.

The term "straight or branched $C_1$-$C_6$ alkyl" refers to a saturated aliphatic hydrocarbon radical, including straight chain and branched chain groups of from 1 to 6 carbon atoms, e.g. methyl, ethyl, propyl, 2-propyl, n-butyl, iso-butyl, tert-butyl, pentyl and the like. The alkyl group may be substituted or unsubstituted. When substituted, the substituent groups are preferably one to three, independently selected from the group consisting of halogen, alkenyl, alkynyl, cyano, nitro, NHCOR7, COR7, NR4R5, NR4COR4, OR6, SR6, SOR10, $SO_2R_{10}$, NHSOR10, $NHSO_2R_{10}$, R8R9N—$C_1$-$C_6$ alkyl, R8O—$C_1$-$C_6$ alkyl, an optionally further substituted $C_3$-$C_6$ cycloalkyl, heterocyclyl, aryl and heteroaryl, wherein R4, R4, R5, R6, R8, R9 and R10 are as defined above.

The term "$C_3$-$C_6$ cycloalkyl" refers to a 3- to 6-membered all-carbon monocyclic ring, which may contain one or more double bonds but does not have a completely conjugated π-electron system. Examples of cycloalkyl groups, without limitation, are cyclopropyl, cyclobutyl, cyclopentyl, cyclopentenyl, cyclohexyl, cyclohexenyl and cyclohexadienyl. A cycloalkyl group may be substituted or unsubstituted. When sustituted, the substituent groups are preferably one or two substituents, independently selected from the group consisting of halogen, alkenyl, alkynyl, cyano, nitro, NHCOR7, COR7, NR4R5, NR4COR4, OR6, SR6, SOR10, SO$_2$R10, NHSOR10, NHSO$_2$R10, R8R9N—C$_1$-C$_6$ alkyl, R8O—C$_1$-C$_6$ alkyl, an optionally further substituted straight or branched C$_1$-C$_6$ alkyl, C$_3$-C$_6$ cycloalkyl, heterocyclyl, aryl and heteroaryl, wherein R4, R5, R6, R7, R8, R9 and R10 are as defined above.

The term "heterocyclyl" refers to a 3- to 7-membered, saturated or partially unsaturated carbocyclic ring where one or more carbon atoms are replaced by heteroatoms such as nitrogen, oxygen and sulfur. Not limiting examples of heterocyclyl groups are, for instance, oxiranyl, aziridinyl, oxetanyl, azetidinyl, tetrahydrofuranyl, dihydrofuranyl, tetrahydrothiophenyl, dihydrothiophenyl, pyrrolidinyl, dihydropyrrolyl, pyranyl, dihydropyranyl, tetrahydropyranyl, tetrahydrothiopyranyl, piperidinyl, pyrazolinyl, isoxazolidinyl, isoxazolinyl, thiazolidinyl, thiazolinyl, isothiazolinyl, dioxanyl, piperazinyl, morpholinyl, thiomorpholinyl, examethyleneiminyl, homopiperazinyl and the like. A heterocyclyl group may be substituted or unsubstituted. When substituted, the substituent groups are preferably one or two substituents, independently selected from the group consisting of halogen, alkenyl, alkynyl, cyano, nitro, NHCOR7, COR7, NR4R5, NR4COR4, OR6, SR6, SOR10, SO$_2$R10, NHSOR10, NHSO$_2$R10, R8R9N—C$_1$-C$_6$ alkyl, R8O—C$_1$-C$_6$ alkyl, an optionally further substituted straight or branched C$_1$-C$_6$ alkyl, C$_3$-C$_6$ cycloalkyl, heterocyclyl, aryl and heteroaryl, wherein R4, R4, R5, R6, R8, R9 and R10 are as defined above.

The term "aryl" refers to a mono-, bi- or poly-carbocyclic hydrocarbon with from 1 to 4 ring systems, optionally further fused or linked to each other by single bonds, wherein at least one of the carbocyclic rings is "aromatic", wherein the term "aromatic" refers to completely conjugated pi-electron bond system. Non limiting examples of such aryl groups are phenyl, α- or β-naphthyl or biphenyl groups.

The term "heteroaryl" refers to aromatic heterocyclic rings, typically 5- to 7-membered heterocycles with from 1 to 3 heteroatoms selected among N, O and S; the heteroaryl ring can be optionally further fused or linked to aromatic and non-aromatic carbocyclic and heterocyclic rings. Not limiting examples of such heteroaryl groups are, for instance, pyridyl, pyrazinyl, pyrimidinyl, pyridazinyl, indolyl, imidazolyl, thiazolyl, isothiazolyl, pyrrolyl, phenyl-pyrrolyl, furyl, phenyl-furyl, oxazolyl, isoxazolyl, pyrazolyl, thienyl, benzothienyl, isoindolinyl, benzoimidazolyl, quinolinyl, isoquinolinyl, 1,2,3-triazolyl, 1-phenyl-1,2,3-triazolyl, 2,3-dihydroindolyl, 2,3-dihydrobenzofuranyl, 2,3-dihydrobenzothiophenyl; benzopyranyl, 2,3-dihydrobenzoxazinyl, 2,3-dihydroquinoxalinyl and the like.

The aryl and heteroaryl groups can be optionally substituted by one or more, preferably one, two or three substituents independently selected from halogen, alkenyl, alkynyl, cyano, nitro, NHCOR7, COR7, NR4R5, NR4COR4, OR6, SR6, SOR10, SO$_2$R10, NHSOR10, NHSO$_2$R10, R8R9N—C$_1$-C$_6$ alkyl, R8O—C$_1$-C$_6$ alkyl, an optionally further substituted straight or branched C$_1$-C$_6$ alkyl, C$_3$-C$_6$ cycloalkyl, heterocyclyl, aryl and heteroaryl, wherein R4, R5, R6, R7, R8, R9 and R10 are as defined above.

The term "halogen" indicates fluorine, chlorine, bromine or iodine.

The term "alkenyl" indicates an aliphatic C2-06 hydrocarbon chain containing at least one carbon-carbon double bond and which can be straight or branched. Representative examples include, but are not limited to, ethenyl, 1-propenyl, 2-propenyl, 1- or 2-butenyl, and the like.

The term "alkynyl" indicates an aliphatic C$_2$-C$_6$ hydrocarbon chain containing at least one carbon-carbon triple bond and which can be straight or branched. Representative examples include, but are not limited to, ethynyl, 1-propynyl, 2-propynyl, 1- or 2-butynyl, and the like.

The term "pharmaceutically acceptable salt" of compounds of formula (I) refers to those salts that retain the biological effectiveness and properties of the parent compound. Such salts include acid addition salts with inorganic acids such as hydrochloric, hydrobromic, nitric, phosphoric, sulfuric, perchloric acid and the like, or with organic acids such as acetic, trifluoroacetic, propionic, glycolic, lactic, (D) or (L) malic, maleic, fumaric, methanesulfonic, ethanesulfonic, benzoic, p-toluenesulfonic, salicylic, cinnamic, mandelic, tartaric, citric, succinic, malonic acid and the like; salts formed when an acidic proton present in a compound of formula (I) is either replaced by a metal ion, e.g., an alkali metal ion such as sodium or potassium, or an alkaline earth ion such as calcium or magnesium, or coordinates with an organic base such as ethanolamine, diethanolamine, triethanolamine, tromethamine, N-methylglucamine, and the like.

A preferred class of compounds of formula (I) are the compounds wherein:

R' and R" are each independently hydrogen or C$_1$-C$_3$ alkyl, and

R1, R2 and R3 are independently hydrogen, halogen or hydroxy.

Another preferred class of compounds of formula (I) are the compounds wherein:

R' and R" are each independently hydrogen or methyl, and R1, R2 and R3 are hydrogen.

A more preferred class of compounds of formula (I) are the compounds wherein

Ar is a group of formula:

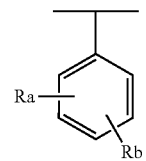

wherein Ra is (CH$_2$)$_n$A or O-G', wherein A, G' and n are as defined above, and Rb is as defined above.

Another more preferred class of compounds of formula (I) are the compounds wherein Ar is a group of formula:

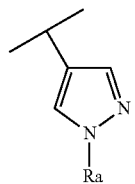

wherein Ra is (CH$_2$)$_n$-A and A and n are as defined above.

Specific compounds (cpd.) of the invention are listed below:

1. N-(5-benzyloxy-1H-indazol-3-yl)-4-(4-methyl-piperazin-1-yl)-benzamide,

2. N-[5-(3-fluoro-benzyloxy)-1H-indazol-3-yl]-4-(4-methyl-piperazin-1-yl)-benzamide,
3. N-(5-benzyloxy-1H-indazol-3-yl)-2-(2-methoxy-ethylamino)-4-(4-methyl-piperazin-1-yl)-benzamide,
4. N-[5-(2-chloro-3,6-difluoro-benzyloxy)-1H-indazol-3-yl]-4-(4-methyl-piperazin-1-yl)-benzamide,
5. N-[5-(3,5-difluoro-benzyloxy)-1H-indazol-3-yl]-2-(2-methoxy-ethylamino)-4-(4-methyl-piperazin-1-yl)-benzamide,
6. N-(5-benzyloxy-1H-indazol-3-yl)-4-(4-methyl-piperazin-1-yl)-2-(tetrahydro-pyran-4-ylamino)-benzamide,
7. N-[5-(3-fluoro-benzyloxy)-1H-indazol-3-yl]-4-(4-methyl-piperazin-1-yl)-2-(tetrahydro-pyran-4-ylamino)-benzamide,
8. N-[5-(3,5-difluoro-benzyloxy)-1H-indazol-3-yl]-4-(4-methyl-piperazin-1-yl)-2-(tetrahydro-pyran-4-ylamino)-benzamide,
9. N-(5-benzyloxy-1H-indazol-3-yl)-5-(4-methyl-piperazin-1-yl)-2-(tetrahydro-pyran-4-ylamino)-benzamide,
10. N-{5-[1-(3,5-difluoro-phenyl)-ethoxy]-1H-indazol-3-yl}-4-(4-methyl-piperazin-1-yl)-2-(tetrahydro-pyran-4-ylamino)-benzamide,
11. N-[5-(2,5-difluoro-benzyloxy)-1H-indazol-3-yl]-4-(4-methyl-piperazin-1-yl)-2-(tetrahydro-pyran-4-ylamino)-benzamide,
12. N-[5-(2,3-difluoro-benzyloxy)-1H-indazol-3-yl]-4-(4-methyl-piperazin-1-yl)-2-(tetrahydro-pyran-4-ylamino)-benzamide,
13. N-[5-(3,4-difluoro-benzyloxy)-1H-indazol-3-yl]-4-(4-methyl-piperazin-1-yl)-2-(tetrahydro-pyran-4-ylamino)-benzamide,
14. N-[5-(2-fluoro-benzyloxy)-1H-indazol-3-yl]-4-(4-methyl-piperazin-1-yl)-2-(tetrahydro-pyran-4-ylamino)-benzamide,
15. N-(5-benzyloxy-1H-indazol-3-yl)-4-[(3-dimethylamino-propyl)-methyl-amino]-2-nitro-benzamide,
16. N-{5-[(R)-1-(3,5-difluoro-phenyl)-ethoxy]-1H-indazol-3-yl}-4-(4-methyl-piperazin-1-yl)-2-(tetrahydro-pyran-4-ylamino)-benzamide,
17. N-{5-[(S)-1-(3,5-difluoro-phenyl)-ethoxy]-1H-indazol-3-yl}-4-(4-methyl-piperazin-1-yl)-2-(tetrahydro-pyran-4-ylamino)-benzamide,
18. 2-amino-N-[5-(3,5-difluoro-benzyloxy)-1H-indazol-3-yl]-4-[(3-dimethylamino-propyl)-methyl-amino]-benzamide,
19. N-[5-(2-chloro-5-fluoro-benzyloxy)-1H-indazol-3-yl]-4-(4-methyl-piperazin-1-yl)-2-(tetrahydro-pyran-4-ylamino)-benzamide,
20. N-[5-(3,5-difluoro-benzyloxy)-1H-indazol-3-yl]-4-[(3-dimethylamino-propyl)-methyl-amino]-2-(tetrahydro-pyran-4-ylamino)-benzamide,
21. N-[5-(3,5-difluoro-benzyloxy)-1H-indazol-3-yl]-4-[(3-dimethylamino-propyl)-methyl-amino]-2-nitro-benzamide,
22. N-[5-(3-chloro-5-fluoro-benzyloxy)-1H-indazol-3-yl]-4-(4-methyl-piperazin-1-yl)-2-(tetrahydro-pyran-4-ylamino)-benzamide,
23. N-[5-(3-fluoro-5-methyl-benzyloxy)-1H-indazol-3-yl]-4-(4-methyl-piperazin-1-yl)-2-(tetrahydro-pyran-4-ylamino)-benzamide,
24. N-[5-(5-fluoro-2-methyl-benzyloxy)-1H-indazol-3-yl]-4-(4-methyl-piperazin-1-yl)-2-(tetrahydro-pyran-4-ylamino)-benzamide,
25. 1H-pyrrole-2-carboxylic acid {2-[5-(3,5-difluoro-benzyloxy)-1H-indazol-3-ylcarbamoyl]-5-[(3-dimethylamino-propyl)-methyl-amino]-phenyl}-amide,
26. N-[5-(2-methoxy-benzyloxy)-1H-indazol-3-yl]-4-(4-methyl-piperazin-1-yl)-2-(tetrahydro-pyran-4-ylamino)-benzamide,
27. 2-amino-N-(5-benzyloxy-1H-indazol-3-yl)-4-[(3-dimethylamino-propyl)-methyl-amino]-benzamide,
28. N-[5-(4-fluoro-benzyloxy)-1H-indazol-3-yl]-4-(4-methyl-piperazin-1-yl)-2-(tetrahydro-pyran-4-ylamino)-benzamide,
29. N-(5-benzyloxy-1H-indazol-3-yl)-4-(4-methyl-piperazin-1-yl)-2-nitro-benzamide,
30. N-[5-(3,5-Difluoro-benzyloxy)-1H-indazol-3-yl]-4-(4-methyl-piperazin-1-yl)-2-nitro-benzamide,
31. N-[5-(3,5-difluoro-benzyloxy)-1H-indazol-3-yl]-2-(3-methoxy-propylamino)-4-(4-methyl-piperazin-1-yl)-benzamide,
32. N-[5-(3,5-difluoro-benzyloxy)-1H-indazol-3-yl]-2-((R)-2-methoxy-1-methyl-ethylamino)-4-(4-methyl-piperazin-1-yl)-benzamide,
33. N-[5-(3,5-difluoro-benzyloxy)-1H-indazol-3-yl]-2-fluoro-4-(4-methyl-piperazin-1-yl)-benzamide,
34. N-[5-(3,5-difluoro-benzyloxy)-1H-indazol-3-yl]-2-(2-methoxy-1,1-dimethyl-ethylamino)-4-(4-methyl-piperazin-1-yl)-benzamide,
35. 4-[2-[5-(3,5-difluoro-benzyloxy)-1H-indazol-3-ylcarbamoyl]-5-(4-methyl-piperazin-1-yl)-phenylamino]-piperidine-1-carboxylic acid ethyl ester,
36. N-[5-(3,5-difluoro-benzyloxy)-1H-indazol-3-yl]-2-(2-fluoro-ethylamino)-4-(4-methyl-piperazin-1-yl)-benzamide,
37. 2-benzylamino-N-[5-(3,5-difluoro-benzyloxy)-1H-indazol-3-yl]-4-(4-methyl-piperazin-1-yl)-benzamide,
38. N-[5-(3,5-difluoro-benzyloxy)-1H-indazol-3-yl]-2-(1,2-dimethoxy-ethylamino)-4-(4-methyl-piperazin-1-yl)-benzamide,
39. 4-(4-methylpiperazin-1-yl)-N-{5-[(3-phenoxybenzyl)oxy]-1H-indazol-3-yl}benzamide,
40. 3-chloromethyl-N-[5-(3,5-difluoro-benzyloxy)-1H-indazol-3-yl]-benzamide
41. N-[5-(3,5-difluoro-benzyloxy)-1H-indazol-3-yl]-3-piperidin-1-ylmethyl-benzamide,
42. 3-(azetidin-1-ylmethyl)-N-{5-[(3,5-difluorobenzyl)oxy]-1H-indazol-3-yl}benzamide,
43. N-{5-[(3,5-difluorobenzyl)oxy]-1H-indazol-3-yl}-3-(pyrrolidin-1-ylmethyl)benzamide,
44. N-{5-[(3,5-difluorobenzyl)oxy]-1H-indazol-3-yl}-3-[(2-methoxyethyl)(methyl)amino]benzamide,
45. N-{5-[1-(3,5-difluorophenyl)ethoxy]-1H-indazol-3-yl}-4-(4-methylpiperazin-1-yl)benzamide,
46. N-{5-[1-(3,5-difluorophenyl)ethoxy]-1H-indazol-3-yl}-3-(4-methylpiperazin-1-yl)benzamide,
47. N-{5-[(3,5-difluorobenzyl)oxy]-1H-indazol-3-yl}-3-[(1-methylpiperidin-4-yl)oxy]benzamide,
48. N-{5-[(3,5-difluorobenzyl)oxy]-1H-indazol-3-yl}-1-(1-methylpiperidin-4-yl)-1H-pyrazole-4-carboxamide,
49. N-{5-[(3,5-difluorobenzyl)oxy]-1H-indazol-3-yl}-4-[(1-methylpiperidin-4-yl)oxy]benzamide,
50. N-[5-(benzyloxy)-1H-indazol-3-yl]-3-(4-methylpiperazin-1-yl)benzamide,
51. N-[5-(benzyloxy)-1H-indazol-3-yl]-1-(piperidin-4-yl)-1H-pyrazole-4-carboxamide,
52. N-{5-[(2-chloro-3,6-difluorobenzyl)oxy]-1H-indazol-3-yl}-3-(4-methylpiperazin-1-yl)benzamide,
53. N-[5-(benzyloxy)-1H-indazol-3-yl]-3-(piperazin-1-yl)benzamide,
54. N-[5-(benzyloxy)-1H-indazol-3-yl]-2-methyl-4-(4-methylpiperazin-1-yl)benzamide, 55. N-{5-[(2-chloro-3,6-difluorobenzyl)oxy]-1H-indazol-3-yl}-2-methyl-4-(4-methylpiperazin-1-yl)benzamide,
56. N-{5-[(3,5-difluorobenzyl)oxy]-1H-indazol-3-yl}-4-(4-methylpiperazin-1-yl)benzamide,
57. N-[5-(benzyloxy)-1H-indazol-3-yl]-2-methoxy-4-(4-methylpiperazin-1-yl)benzamide,
58. N-{5-[(2-chloro-3,6-difluorobenzyl)oxy]-1H-indazol-3-yl}-2-methoxy-4-(4-methylpiperazin-1-yl)benzamide,
59. N-{5-[(3,5-difluorobenzyl)oxy]-1H-indazol-3-yl}-3-(4-methylpiperazin-1-yl)benzamide,
60. N-{5-[(3,5-difluorobenzyl)oxy]-1H-indazol-3-yl}-4-{[3-(dimethylamino)propyl](methyl)amino}benzamide,
61. N-{5-[(3,5-difluorobenzyl)oxy]-1H-indazol-3-yl}-4-(piperidin-1-ylmethyl)benzamide,
62. N-{5-[(3,5-difluorobenzyl)oxy]-1H-indazol-3-yl}-4-(morpholin-4-ylmethyl)benzamide,
63. N-{5-[(3,5-difluorobenzyl)oxy]-1H-indazol-3-yl}-3-[2-(dimethylamino)ethoxy]benzamide,
64. N-{5-[(3,5-difluorobenzyl)oxy]-1H-indazol-3-yl}-4-nitrobenzamide,
65. N-{5-[(3,5-difluorobenzyl)oxy]-1H-indazol-3-yl}-3-nitrobenzamide,
66. N-{5-[(3,5-difluorobenzyl)oxy]-1H-indazol-3-yl}-3-[(1-methylpiperidin-4-yl)amino]benzamide,
67. N-{5-[(3,5-difluorobenzyl)oxy]-1H-indazol-3-yl}-4-[(1-methylpiperidin-4-yl)amino]benzamide,
68. N-{5-[(2,5-difluorobenzyl)oxy]-1H-indazol-3-yl}-4-(4-methylpiperazin-1-yl)benzamide,
69. N-{5-[(3,5-difluorobenzyl)oxy]-1H-indazol-3-yl}-3-(4-methylpiperazin-1-yl)benzamide,
70. 4-(4-methylpiperazin-1-yl)-N-(5-phenoxy-1H-indazol-3-yl)benzamide,
71. N-[5-(3-fluorophenoxy)-1H-indazol-3-yl]-4-(4-methylpiperazin-1-yl)benzamide
72. N-{5-[4-(benzyloxy)phenoxy]-1H-indazol-3-yl}-4-(4-methylpiperazin-1-yl)benzamide,
73. 4-(4-methylpiperazin-1-yl)-N-[5-(4-phenoxyphenoxy)-1H-indazol-3-yl]benzamide,
74. N-{5-[3-(benzyloxy)phenoxy]-1H-indazol-3-yl}-4-(4-methylpiperazin-1-yl)benzamide,
75. N-[5-(3,5-difluorophenoxy)-1H-indazol-3-yl]-4-(4-methylpiperazin-1-yl)benzamide,
76. N-[5-(3,5-difluorophenoxy)-1H-indazol-3-yl]-4-(4-methylpiperazin-1-yl)-2-(tetrahydro-2H-pyran-4-ylamino)benzamide,
77. N-[5-(3,5-difluorophenoxy)-1H-indazol-3-yl]-3-[(1-methylpiperidin-4-yl)oxy]benzamide,
78. 2-methyl-4-(4-methylpiperazin-1-yl)-N-(5-phenoxy-1H-indazol-3-yl)benzamide
79. N-{5-(3,5-difluorophenoxy)-1H-indazol-3-yl}-1-(1-methylpiperidin-4-yl)-1H-pyrazole-4-carboxamide,
80. N-[5-(3,5-difluorophenoxy)-1H-indazol-3-yl]-4-[(1-methylpiperidin-4-yl)oxy]benzamide,
81. N-[5-(3,5-difluorophenoxy)-1H-indazol-3-yl]-3-(4-methylpiperazin-1-yl)benzamide,
82. N-[5-(3,5-difluorophenoxy)-1H-indazol-3-yl]-2-methyl-4-(4-methylpiperazin-1-yl)benzamide,
83. 3-(4-methylpiperazin-1-yl)-N-(5-phenoxy-1H-indazol-3-yl)benzamide,
84. N-[5-(3,5-difluorophenoxy)-1H-indazol-3-yl]-2-methoxy-4-(4-methylpiperazin-1-yl)benzamide hydrochloride,
85. 2-methoxy-4-(4-methylpiperazin-1-yl)-N-(5-phenoxy-1H-indazol-3-yl)benzamide hydrochloride,
86. N-[5-(3,5-difluorophenoxy)-1H-indazol-3-yl]-3-[2-(dimethylamino)ethoxy]benzamide,
87. N-[5-(3,5-difluorophenoxy)-1H-indazol-3-yl]-3-nitrobenzamide,
88. N-[5-(3,5-difluorophenoxy)-1H-indazol-3-yl]-4-nitrobenzamide,
89. 3-amino-N-[5-(3,5-difluorophenoxy)-1H-indazol-3-yl]benzamide,
90. 4-amino-N-[5-(3,5-difluorophenoxy)-1H-indazol-3-yl]benzamide,
91. N-[5-(3,5-difluorophenoxy)-1H-indazol-3-yl]-3-[(1-methylpiperidin-4-yl)amino]benzamide,
92. N-[5-(3,5-difluorophenoxy)-1H-indazol-3-yl]-4-[(1-methylpiperidin-4-yl)amino]benzamide,
93. N-[5-(3,5-difluorophenoxy)-1H-indazol-3-yl]-4-[2-(dimethylamino)ethoxy]benzamide,
94. N-{5-[(3,5-difluorobenzyloxy]-1H-indazol-3-yl}-4-amino-benzamide,
95. N-{5-[(3,5-difluorobenzyloxy]-1H-indazol-3-yl}-3-amino-benzamide and
96. 4-chloromethyl-N-[5-(3,5-difluoro-benzyloxy)-1H-indazol-3-yl]-benzamide.

The present invention also provides a process for the preparation of a compound of formula (I) as defined above, characterized in that the process comprises:

d) condensing a compound of formula (III):

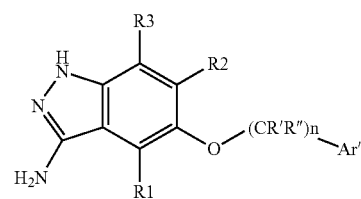

wherein n, Ar', R1, R2, R3, R' and R" are as defined above, with a compound of formula (II):

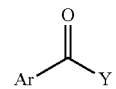

wherein Ar is as defined above and Y represents hydroxy, or a suitable leaving group such as halogen, optionally separating the resultant compound of formula (I) as defined above into the single isomers, converting the compound of formula (I) into a different compound of formula (I), and/or into a pharmaceutically acceptable salt if desired. The present invention further provides a process for the preparation of a compound of formula (I) as defined above, characterized in that the compound of formula (III) as defined above, is prepared according to the following steps:

a) condensing a compound of formula (VI):

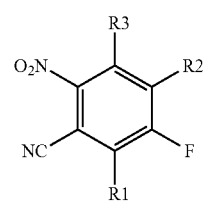

wherein R1, R2 and R3 are as defined above, with an alcohol derivative of formula (VII):

Ar'(CR'R")$_n$OH (VII)

wherein n, Ar', R' and R" are as defined above;

b) reducing the nitro group of the resultant compound of formula (V):

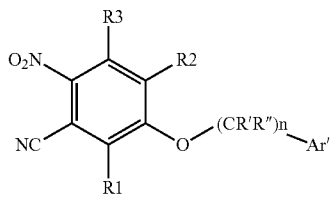

(V)

wherein n, Ar', R', R", R1, R2 and R3 are as defined above;

c) reducing the cyano group of the resultant compound of formula (IV):

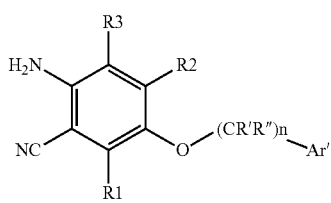

(IV)

wherein n, Ar', R', R", R1, R2 and R3 are as defined above, in the presence of a suitable reagent system like for example NaNO$_2$/HCl and SnCl$_2$, to give a compound of formula (III) as defined above.

A compound of formula (I) may be converted into another compound of formula (I), said conversion is carried out by one or more of the following reactions:

1) reducing a compound of formula (I) wherein Ar is a substituted aryl and one of the substituents is NO$_2$, for obtaining a compound of formula (I) wherein such substituent is NH$_2$;

2) acylating a compound of formula (I) wherein Ar is a substituted aryl and one of the substituents is NH$_2$, by reaction with an acylating agent of formula (VIII) or (IX):

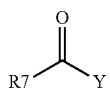

(VIII)

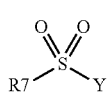

(IX)

wherein R7 and Y are as defined above, for obtaining a compound of formula (I) wherein such substituent is a NHCOR7 or NHSO$_2$R7 residue, wherein R7 is as defined above;

3) reacting a compound of formula (I) wherein Ar is a substituted aryl and one of the substituents is NH$_2$, with a suitable aldehyde or ketone in the presence of a reducing agent, for obtaining a compound of formula (I) wherein such substituent is a NR4R5 group, wherein one of the R4 or R5 is hydrogen and the other is an optionally further substituted straight or branched C$_1$-C$_6$ alkyl, C$_3$-C$_6$ cycloalkyl, heterocyclyl, aryl, heteroaryl, R8R9N—C$_2$-C$_6$ alkyl or R8O—C$_2$-C$_6$ alkyl, wherein R8 and R9 are as defined above;

4) converting a compound of formula (I) wherein n is 1, into another compound of formula (I) with a different Ar' group by a multi-step process consisting in:

4A) protecting a compound of formula (I);

4B) reducing the resultant compound of formula (Xa):

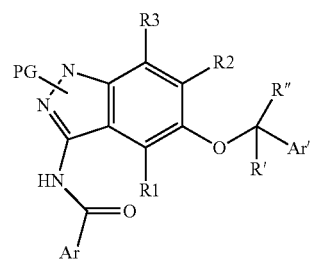

(Xa)

wherein Ar, Ar', R', R", R1, R2 and R3 are as defined above and PG is a suitable protecting group such as ethoxycarbonyl, methoxycarbonyl, tert-butoxycarbonyl or trifluoroacetyl;

4C) coupling the resultant compound of formula (XI):

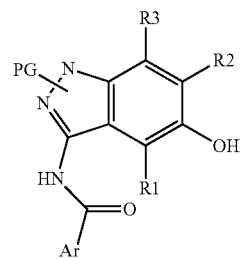

(XI)

wherein Ar, R1, R2, R3 and PG are as defined above, with a compound of formula (XII)

Ar'(CR'R")W (XII)

wherein Ar', R' and R" are as defined above but Ar' is different from Ar' of formula (Xa), and W represents a halogen atom, such as chlorine, bromine or iodine, or a suitable leaving group like hydroxy-group or sulphonates, such as p-toulenesulphonate, methanesulphonate or trifluoromethanesulphonate;

4D) removing the protecting group from the resultant compound of formula (X):

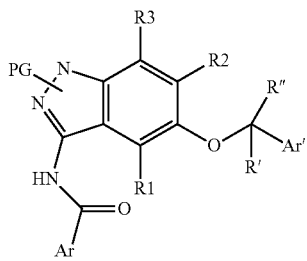

(X)

wherein Ar, Ar', R', R", R1, R2, R3 and PG are as defined above, to give a compound of formula (I) wherein n is 1 and Ar, Ar', R1, R2, R3, R' and R" are as defined above but Ar' is different from Ar' of formula (Xa).

The synthesis of a compound of formula (I), according to the synthetic process described above, can be conducted in a stepwise manner, whereby each intermediate is isolated and purified by standard purification techniques, like, for example, column chromatography, before carrying out the subsequent reaction. Alternatively, two or more steps of the synthetic sequence can be carried out in a so-called "one-pot" procedure, as known in the art, whereby only the compound resulting from the two or more steps is isolated and purified.

The reported Scheme 1 shows the preparation of a compound of formula (I) wherein n, Ar, Ar', R', R", R1, R2 and R3 have the above meanings.

(II) wherein Y is hydroxy is converted into its corresponding acyl chloride wherein Y is chlorine in the presence of thionyl chloride or oxalyl chloride, in a suitable solvent, such as toluene, dichloromethane, chloroform, diethyl ether, tetrahydrofuran, 1,4-dioxane, at a temperature ranging from about −10° C. to reflux and for a period of time varying from about 1 hour to about 96 hours. The acyl chloride is isolated by evaporation of the solvent and further reacted with (III) in the presence of a base such a pyridine, triethylamine or N-ethyldiisopropylamine in a suitable solvent, such as toluene, dichloromethane, chloroform, diethyl ether, tetrahydrofuran, 1,4-dioxane, at a temperature ranging from about −40° C. to reflux and for a period of time varying from about 1 hour to about 96 hours. Alternatively, a compound of formula (II) is reacted with a compound of formula (III) in the presence of an activating agent such as hydroxybenzotriazole, dicyclohexyl carbodiimide, diisopropyl carbodiimide, 1-ethyl-3-(3'-dimethylamino)carbodiimide hydrochloric acid salt. Preferably, this reaction is carried out in a suitable solvent such as, for instance, tetrahydrofuran, dichloromethane, toluene, 1,4-dioxane, and in the presence of a proton scavenger such as, for example, pyridine, triethylamine, N,N-diisopropylethylamine, at a temperature ranging from room temperature to reflux, for a time ranging from about 30 min. to about 96 hours.

According to step c), the transformation of a compound of formula (IV) into a compound of formula (III) can be accomplished in a variety of ways and experimental conditions, which are widely known in the art for the preparation of 3-aminoindazoles, for example using nitrous acid/tin chlo-

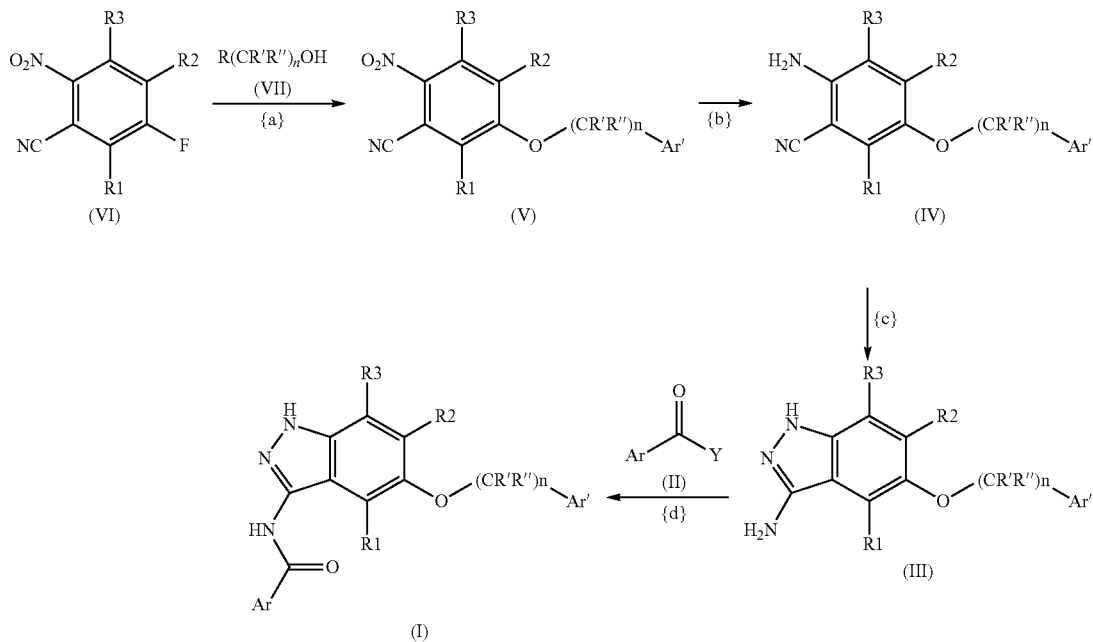

Scheme 1

According to step d) a compound of formula (I) can be obtained by reacting a compound of formula (III) with a compound of formula (II) in a variety of ways and experimental conditions, which are widely known in the art for condensation reactions. Preferably a compound of formula ride or nitrous acid/hydrazine. Preferably this reaction is carried out in a suitable solvent such as, for instance tetrahydrofuran, 1,4-dioxane, dimethyl sulfoxide, acetonitrile, water, methanol, ethanol or n-butanol at a temperature ranging from 0° C. to reflux and for a period of time varying from about 1 hour to about 96 hours.

According to step b), the reduction of a compound of formula (V) into a compound of formula (IV) can be carried out in a variety of ways, according to conventional methods well known in the literature. Preferably this conversion is carried out in a suitable solvent such as, for instance, dichloromethane, methanol, ethanol, water, tetrahydrofuran, 1,4-dioxane, N,N-dimethylformamide, acetic acid, or a mixture thereof, in the presence of a suitable reducing agent, such as, for instance, hydrogen and a hydrogenation catalyst, or by treatment with cyclohexene or cyclohexadiene, or formic acid or ammonium formate and a hydrogenation catalyst, or a metal such as iron or zinc in the presence of an inorganic acid, such as hydrochloric acid, or by treatment with tin (II) chloride or sodium hydrosulfite in the presence of tetrabutylammonium chloride, at a temperature ranging from 0° C. to reflux and for a time varying from about 1 hour to about 96 hours. The hydrogenation catalyst is usually a metal, most often palladium, which can be used as such or supported on carbon.

According to step a), the condensation of a compound of formula (VI) with a into a compound of formula (VII), can be carried out in a variety of ways, according to conventional methods for aromatic nucleofilic substitution. Preferably, this reaction is carried out in a suitable solvent such as, for instance, tetrahydrofuran, dioxane, N,N-dimethylformamide, dimethylsulfoxide, dimethoxyethane, toluene, xylene, or a mixture thereof, in the presence of a suitable base, such as, for instance, lithium diisopropylamide, lithium, sodium or potassium bis(trimethylsilyl)amide, triethylamine, diisopropylethylamine, sodium, potassium or cesium carbonate, sodium hydride, sodium hydroxide or cesium fluoride, at a temperature ranging from −20° C. to reflux and for a time varying from about 1 hour to about 96 hours.

According to the conversion 1), the reduction of a compound of formula (I) wherein Ar is a substituted aryl and one of the substituents is nitro, to a compound of formula (I) wherein such substituent is amino, can be carried out in a variety of ways, according to conventional methods well known in the literature. Preferably this conversion is carried out in a suitable solvent such as, for instance, methanol, ethanol, water, tetrahydrofuran, 1,4-dioxane, N,N-dimethylformamide, acetic acid, or a mixture thereof, in the presence of a suitable reducing agent, such as, for instance, hydrogen and a hydrogenation catalyst, or by treatment with cyclohexene or cyclohexadiene, or formic acid or ammonium formate and a hydrogenation catalyst, or a metal such as iron or zinc in the presence of an inorganic acid, such as hydrochloric acid, or by treatment with tin (II) chloride or sodium hydrosulfite in the presence of tetrabutylammonium chloride, at a temperature ranging from 0° C. to reflux and for a time varying from about 1 hour to about 96 hours. The hydrogenation catalyst is usually a metal, most often palladium, which can be used as such or supported on carbon.

According to the conversion 2), the acylation of a compound of formula (II) wherein Ar is a substituted aryl and one of the substituents is amino, by reaction with an acetylating agent of formula (VIII) or (IX) to give a compound of formula (I) wherein such substituent is a NHCOR7 or NHSO$_2$R7 residue, can be carried out in a variety of ways, according to conventional methods well known in the literature. Preferably this conversion is carried out under conditions analogous to that reported for step d).

According to the conversion 3), the reductive amination of a compound of formula (I) wherein Ar is a substituted aryl and one of the substituents is amino, by reaction with a suitable aldehyde or ketone can be conducted in a variety of ways, according to conventional methods for carrying out reductive alkylations. Preferably, this reaction is carried out in a suitable solvent such as, for instance, methanol, N,N-dimethylformamide, dichloromethane, tetrahydrofuran, or a mixture thereof, in the presence of a suitable reducing agent such as, for instance, sodium borohydride, tetra-alkylammonium borohydride, sodium cyano borohydride, sodium triacetoxyborohydride, tetramethylammonium triacetoxy borohydride and in presence of an acid catalyst, such as, for instance, acetic acid or trifluoroacetic acid, at a temperature ranging from about 0° C. to reflux and for a time varying from about 1 hour to about 96 hours.

According to the conversion 4), step 4A), the protection of a compound of formula (I) can be carried out in a variety of ways and experimental conditions which are widely known in the art for protection of the nitrogen atom. Preferably the reaction is carried out by treatment with an excess of trifluoroacetic anhydride or trifluoroacetyl chloride, ethyl or methyl chloroformate or tert-butoxycarbonyl anhydride in a suitable solvent such as 1,4-dioxane, acetonitrile, tetrahydrofuran, N,N-dimethylformamide, toluene, dichloromethane. Typically, the reaction is carried out under basic conditions, for instance in the presence of 1,8-diazabicyclo[5.4.0]undec-7-ene, N,N-dimethylaminopyridine, pyridine, triethylamine, at a temperature ranging from 0° C. to about 110° C. and for a time varying from about 30 minutes to about 96 hours.

According to the conversion 4), step 4B), the reduction a compound of formula (X) can be carried out in a variety of ways, according to conventional methods well known in the literature. Preferably it is carried out in a suitable solvent such as, for instance, methanol, ethanol, tetrahydrofuran, 1,4-dioxane, N,N-dimethylformamide, or a mixture thereof, in the presence of a suitable reducing agent, such as, for instance, hydrogen and a hydrogenation catalyst, or by treatment with cyclohexene or cyclohexadiene, or formic acid or ammonium formate and a hydrogenation catalyst, at a temperature ranging from 0° C. to reflux and for a time varying from about 1 hour to about 96 hours. The hydrogenation catalyst is usually a metal, most often palladium, which can be used as such or supported on carbon.

According to the conversion 4), step 4C), the condensation of a compound of formula (XI) with a compound of formula (XII) can be carried out in a variety of ways, according to conventional methods for O-alkylation reactions. Preferably, this reaction is carried out in a suitable solvent such as, for instance, tetrahydrofuran, 1,4-dioxane, N,N-dimethylformamide, dimethoxyethane, in the presence of a suitable base, such as, for instance, triethylamine, diisopropylethylamine, sodium, potassium or cesium carbonate, sodium hydride, at a temperature ranging from −78° C. to reflux and for a time varying from about 1 hour to about 96 hours. Alkylating agent is usually a halogen or a sulphonates derivative; most often the leaving group is iodo, bromo, triflate or mesylate. Other conventional methods for alcohol-derivatives coupling, namely Mitsunobu-like reactions, can be used. Preferably, these reactions are carried out in a suitable solvent such as, for instance, tetrahydrofuran, 1,4-dioxane, dimethoxyethane, toluene, dichloromethane, acetonitrile, in the presence of a suitable azodicarboxylate/phosphine system such as, for instance, diethylazodicarboxylate/triphenylphosphine at a temperature ranging from −20° C. to reflux and for a time varying from about 1 hour to about 96 hours.

According to the conversion 4), step 4D), the deprotection of a compound of formula (X) can be carried out according to conventional methods enabling the selective hydrolysis of tert-butoxycarbonyl, benzyl, 4-methoxybenzyl, 2,4-dimethoxybenzyl and triphenylmethyl protecting groups.

Preferably this reaction is run under acidic conditions, preferably in the presence of an inorganic or organic acid such as hydrochloric, trifluoroacetic or methanesulfonic acid, in a suitable solvent such as dichloromethane, 1,4-dioxane, a lower alcohol, such as methanol or ethanol, at a temperature ranging from room temperature to about 80° C. and for a period of time varying from about 1 hour to about 48 hours. In alternative, this reactions is carried out under reducing condition, such as, for instance, in the presence of hydrogen and a hydrogenation catalyst in a suitable solvent such as ethanol, methanol, ethyl acetate, or a mixture thereof. The catalyst is usually a metal, most often a palladium derivative such as, for instance, palladium hydroxide or palladium black. Hydrolysis of protecting groups such as the trifluoroacetyl, ethoxycarbonyl or methoxycarbonyl group, can be carried out according to well-known conventional methods. Preferably the reaction is carried out by treatment with an organic or inorganic base such as potassium carbonate, sodium hydroxide, ammonia, triethylamine, N,N-diisopropylethylamine in a suitable solvent such as, for instance, tetrahydrofuran, dichloromethane, toluene, 1,4-dioxane, methanol, ethanol, water or mixtures thereof at a temperature ranging from room temperature to reflux, for a time ranging from about 30 min. to about 96 hours.

It is known to the skilled person that when a compound of formula (II), formula (VIII) or formula (IX) carries functional groups that may interfere in acylation reactions, such groups have to be protected before carrying out the reaction. In particular, when a compound of formula (II), formula (VIII) or formula (IX) is substituted by residues of general formula NR4R5, OR6, SR6, R8R9N—$C_1$-$C_6$ alkyl, or R8O—$C_1$-$C_6$ alkyl wherein R6 or at least one of R4 and R5 or at least one of R8 and R9 represent hydrogen, such groups may be protected as known in the art. It is also known to the skilled person that such protecting group may be removed just after the reaction or at a later stage in the synthetic process.

The deprotection of a compound of formula (I) wherein Ar is a substituted aryl and one of the substituents is a protected amino group can be made in a variety of ways according to conventional methods for deprotecting amino groups. Depending on the amino protecting group, this reaction can be conducted in different ways. In one aspect, such reaction can be carried out by treatment with an inorganic acid, such as hydrochloric, sulphuric or perchloric acid, or an organic acid, such as trifluoroacetic or methanesulfonic acid, in a suitable solvent, such as water, methanol, ethanol, 1,4-dioxane, tetrahydrofuran, diethyl ether, diisopropyl ether, acetonitrile, N,N-dimethylformamide, dichloromethane or mixtures thereof, at a temperature ranging from −20° C. to 80° C., and for a period of time ranging from 30 minutes to 48 hours. In another aspect, such reaction can be carried out by treatment with an inorganic base, such as lithium or sodium or potassium hydroxide, or sodium or potassium or caesium carbonate, or with an organic base, such as triethylamine or N,N-diisopropylethylamine, or with anhydrous hydrazine or hydrazine hydrate in a suitable solvent such as water, methanol, ethanol, 1,4-dioxane, tetrahydrofuran, diethyl ether, diisopropyl ether, acetonitrile, N,N-dimethylformamide, dichlorometane or mixtures thereof, at a temperature ranging from −20° C. to 80° C., and for a period of time ranging from 30 minutes to 72 hours.

Substituted indazole derivatives can be prepared using standard procedures in organic synthesis as reported, for instance, in Smith, Michael—March's Advanced Organic Chemistry: reactions mechanisms and structure—5$^{th}$ Edition, Michael B. Smith and Jerry March, John Wiley & Sons Inc., New York (N.Y.), 2001. It is known to the skilled person that transformation of a chemical function into another may require that one or more reactive centers in the compound containing this function be protected in order to avoid undesired side reactions. Protection of such reactive centers, and subsequent deprotection at the end of the synthetic transformations, can be accomplished following standard procedures described, for instance, in: Green, Theodora W. and Wuts, Peter G. M.—Protective Groups in Organic Synthesis, Third Edition, John Wiley & Sons Inc., New York (N.Y.), 1999.

In cases where a compound of formula (I) contains one or more asymmetric centers, said compound can be separated into the single isomers by procedures known to those skilled in the art. Such procedures comprise standard chromatographic techniques, including chromatography using a chiral stationary phase, or crystallization. General methods for separation of compounds containing one or more asymmetric centers are reported, for instance, in Jacques, Jean; Collet, André; Wilen, Samuel H.,—Enantiomers, Racemates, and Resolutions, John Wiley & Sons Inc., New York (N.Y.), 1981.

A compound of formula (I) can also be transformed into a pharmaceutically acceptable salt according to standard procedures that are known to those skilled in the art. Alternatively, a compound of formula (I) that is obtained as a salt can be transformed into the free base or the free acid according to standard procedures that are known to the skilled person.

The starting materials of the process of the present invention, i.e. compounds of formula (VI), (VII), (VIII), (IX), and (XII) are either commercially available or can be prepared by using well-known methods such as: B. M. Trost and I. Fleming, Comprehensive Organic Synthesis, 1991, Pergamon Press; A. R. Katritzky, O. Meth-Cohn and C. W. Rees, Comprehensive Organic Functional Group Transformations, 1995, Elsevier Pergamon; A. R. Katritzky and R. J. K. Taylor, Comprehensive Organic Functional Group Transformations II, 2005, Elsevier Pergamon Compounds of formula (II) are prepared as described under Preparations from 3 to 9.

Pharmacology

The short forms and abbreviations used herein have the following meaning:
Ci Curie
DMSO dimethylsulfoxide
ID identity
KDa kiloDalton
microCi microCurie
mg milligram
microg microgram
mL milliliter
microL microliter
M molar
mM millimolar
microM micromolar
nM nanomolar
Assays Compounds of the present invention were tested in biochemical assays, as described below.
Preparation of ALK Cytoplasmic Domain for Use in Biochemical Assay
Cloning and Expression ALK cytoplasmic domain, corresponding to the residue 1060-1620 (the numbers of the amino acid residues refer to the Genbank accession number NP 004295.2) was PCR amplified from a human testis cDNA library.

Amplification was performed using the forward oligonucleotide:

```
                                                      [SEQ ID NO: 1]
5'GGGGACAAGTTTGTACAAAAAAGCAGGCTTACTGGAAGTTCTGTT

CCAGGGGCCCCGCCGGAAGCACCAGGAGCTG-3'
``` and the reverse oligonucleotide:

```
                                                      [SEQ ID NO: 2]
5'GGGGACCACTTTGTACAAGAAAGCTGGGTTTCAGGGCCCAGGCTG

GTTCATGCTATT-3'.
```

For cloning purposes, the oligonucleotides included attB sites in order to obtain an attB-flanked PCR product suitable for cloning using the Gateway technology (Invitrogen). Furthermore, for purification purposes, forward primer included a PreScission cleavage site (Amersham Biosciences). The resulting PCR product was cloned in the baculovirus expression vector pVL1393 (Invitrogen) Gateway-modified. For expression and purification purpose, a GST tag was added N-terminal to the ALK cytoplasmic domain. Cloning was performed according to the protocols described in the Gateway manual (Invitrogen).

Baculovirus was generated by cotransfecting Sf9 insect cells with expression vector and the viral DNA using the BaculoGold™ tranfection kit (Pharmingen).

Viral supernatant was recovered after 5 days and subjected to 3 rounds of amplification to increase viral titer.

Recombinant protein was produced by infecting Sf21 insect cells at the density of $1 \times 10^6$ cells/mL with 30 mL viral supernatant per billion cells with shaking at 27° C. After 48 hours of infections the cells were recovered, pelletted and freezed at −80° C.

Protein Purification

Cells were resuspended in lysis buffer (Tris-HCl 50 mM pH8, NaCl 150 mM, CHAPS 0.2%, DTT 20 mM, glycerol 20%, "Complete" protease inhibitor cocktail (Roche Diagnostics), $Na_3VO_4$ 1 mM and lysed by liquid extrusion with a Gaulin homogenizer (Niro Soavi Italy). The lysate was cleared by centrifugation at 20000 g for 30 minutes and loaded on a Glutathione Sepharose 4B (Amersham Biosciences) column.

After extensive wash, recombinant protein was eluted with 10 mM Glutathione in 100 mM Tris-HCl pH8, 10% glycerol.

Affinity purified GST-ALK was loaded on a Heparin Sepharose™ FF (Amersham Biosciences) column and eluted with 50 mM NaCl, 25 mM TRIS pH 7.5, 2 mM DTT, 20% glycerol.

The eluted fractions were pooled and dialyzed against 150 mM NaCl, 50 mM Tris-HCl pH 7.4, 2 mM DTT, 20% glycerol.

Purified protein was stored at −80° C. prior its use in biochemical assay.

Biochemical Assay for Inhibitors of ALK Kinase Activity

ALK enzyme needs pre-activation in order to linearize reaction kinetics.

i. Kinase Buffer (KB) for ALK

Kinase buffer was composed of 50 mM HEPES pH 7.5 containing 1 mM $MnCl_2$, 5 mM $MgCl_2$, 1 mM DTT, 3 microM $Na_3VO_4$, and 0.2 mg/mL BSA. 3×KB is buffer of the same composition and pH as KB, but with three times the concentration of each component.

ii. Assay Conditions

The kinase assay was run with a final enzyme concentration of 20 nM, in the presence of 8 microM ATP, 1 nM $^{33}$P-γ-ATP and 2 microM MBP. The MPB was purchased from Sigma-Aldrich, St. Louis, Mo., USA.

Cell-Based Assays for Inhibitors of ALK Kinase Activity

Western Blot Analysis of ALK and STAT3 Phosphorylation in Karpas-299, SR-786 and SUP-M2 Anaplastic Large Cell Lymphoma Cell Lines Karpas-299, SR-786 and SUP-M2 cells (DSMZ, Braunschwiegh, Germany) were seeded in 6-well tissue culture plates at $5 \times 10^5$ cells/mL in RPMI-1640 medium+2 mM glutamine+10% to 15% FCS (EuroClone, Italy) incubated overnight at 37° C., 5% $CO_2$, 100% relative humidity. After this incubation, cells were treated with desired concentrations of compound for 2 hours at 37° C. Cells were collected by centrifugation at 248×g for 5 minutes, washed with cold PBS, centrifuged again at 248×g for 5 minutes and then lysed in 100 mM Tris-HCl pH 7.4, 2% SDS, 1 mM $Na_3VO_4$, protease inhibitor cocktail [Sigma-Aldrich product #P8340], phosphatase inhibitor cocktail [Sigma-Aldrich products #P2850+ #P5726]). After brief sonication, cell lysates were cleared by centrifugation at 10,000×g for 20 minutes at room temperature and 20 microg/lane of cleared lysate protein were run on NuPAGE gels (NuPAGE 4-12% 10-lane Bis-Tris gels, Invitrogen) with MOPS running buffer, then transferred onto Hybond-ECL nitrocellulose filters (Amersham Biosciences, Little Chalfont, Buckinghamshire, UK) using Mini PROTEAN II chambers (Bio-Rad Laboratories, Hercules, Calif., USA). Filters bearing transferred protein were incubated for 1 hour in blocking buffer (TBS+5% Non-fat Dry Milk [#1706404 Bio-rad, Hercules, Calif., USA]+0.1% Tween 20), and probed over-night in TBS+5% BSA+0.1% Tween 20 at 4° C. containing 1/500 anti-phosho-ALK Tyr 1604 antibody (product #3341 Cell Signaling Technology, Beverly, Mass., USA) for detection of phosphorylated ALK or 1/500 mouse anti-ALK antibody (product #35-4300, Zymed Laboratories, South San Francisco, Calif., USA) for the detection of total ALK or 1/500 mouse anti-phospho STAT3 Tyr 705 antibody (product #612357, BD Transduction Laboratories, Canada) for dectection of phosphorylated STAT3 or 1/1000 mouse anti-STAT3 antibody (product #610190 BD Transduction Laboratories, Canada) for detection of total STAT3.

In all cases, filters were then washed for 20 minutes with several changes of TBS+0.1% Tween 20, and incubated for 1 hour in TBS+5% Non-fat Dry Milk+0.1% Tween 20 containing 1/10000 dilution of horseradish peroxidase conjugated anti-rabbit or mouse IgG (Amersham, product #NA934), then were washed again and developed using the ECL chemiluminescence system (Amersham) according to manufacturer's recommendations. Unless otherwise stated, reagents used were from Sigma-Aldrich, St. Louis, Mo., USA.

In vitro Cell Proliferation Assay for Inhibitors of ALK Kinase Activity

The human ALCL cell lines Karpas-299, SR-786 and SUP-M2 were seeded in 96 well plate (PerkinElmer, Wellesley, Mass., USA) $1 \times 10^5$ cells/mL in RPMI-1640 medium+2 mM glutamine+10% to 15% FCS (EuroClone, Italy), 100 microL/well) and maintained at 37° C., 5% $CO_2$, 100% relative humidity. The following day, plates were treated in duplicates with an appropriate dilution of compounds starting from a 10 mM stock solution in DMSO (final DMSO concentration: 0.1%). Eight untreated control wells were included in each plate. After 72 hours of treatment, 50 microL of CellTiter-Glo Assay (Promega, Madison, Wis., USA) were added to each well and after agitation the luminescence signal is measured using Envision Detector (PerkinElmer Wellesley, Mass., USA).

IC$_{50}$ values were calculated by LSW/Data Analysis using Microsoft Excel sigmoidal curve fitting.

Biochemical Assay for Inhibitors of JAK2 Kinase Activity

General Principle—A specific JAK2 peptide substrate is trans-phosphorylated by JAK2 kinase in the presence of ATP traced with $^{33}$P-γ-ATP. At the end of the phosphorylation reaction, 98% of the cold and radioactive ATP is captured by an excess of dowex ion exchange resin that eventually settles by gravity to the bottom of the reaction plate. The supernatant is subsequently withdrawn and transferred into a counting plate that is then evaluated by β-counting.

Dowex resin preparation—500 g of wet resin (SIGMA, custom prepared resin DOWEX 1×8 200-400 mesh, 2.5 Kg) are weighed out and diluted 2 to 1 in 150 mM sodium formate, pH 3.00. The resin is allowed to settle down overnight and then the supernatant is discarded. After three washes as above over a couple of days, the resin is allowed to settle and two volumes (with respect to the resin volume) are added of 150 mM sodium formate buffer.

Enzyme—The assay has been performed using the commercially available JAK2 kinase domain (Invitrogen, Eugene, Oreg.) The JAK2 kinase domain showed a linear kinetic without prephosphorylation.

JAK2 Kinase Buffer (KB—Kinase buffer was composed of 50 mM HEPES pH 7.5 containing 10 mM MgCl$_2$, 2.5 mM DTT, 10 microM Na$_3$VO$_4$, and 0.2 mg/mL BSA. 3× KB is buffer of the same composition and pH as KB, but with three times the concentration of each component.

Assay conditions—The JAK2 kinase assay was run with a final enzyme concentration of 1 nM, in the presence of 60 microM ATP, 3 nM 33P-γ-ATP and 64 microM of substrate Jaktide (Aminoacid sequence: LPLDKDYYVVREPGQ). The Jaktide was purchased from American Peptide Company (Sunnyvale, Calif.).

Compound Dilution—For IC$_{50}$ determination, test compounds are received as a 1 mM solution in 100% DMSO, distributed into 96 well plates: compounds are then plated into the first column of a microtiter plate (A1 to G1), 100 µl/well.

An automated station for serial dilutions (Biomek FX, Beckman) is used for producing 1:3 dilutions in 100% DMSO, from line A1 to A10, and for all the compounds in the column. Moreover, 4-5 copies of daughter plates are prepared by reformatting 5 microL of this first set of 100% DMSO dilution plates into 384 deep well-plates: one of these plates with the serial dilutions of test compounds will be thawed the day of the experiments, reconstituted at a 3× concentration with water and used in the IC$_{50}$ determination assays. In a standard experiment, the highest concentration (3×) of all compounds is 30 microM, while the lowest one is 1.5 nM.

Each 384 well-plate will contain at least one curve of the standard inhibitor staurosporine and reference wells (total enzyme activity vs. no enzymatic activity) for the Z' and signal to background evaluation.

Assay Scheme—384-well plates, V bottom (test plates) are prepared with 5 µl of the compound dilution (3×) and then placed onto a PlateTrak 12 robotized station (Perkin Elmer; the robot has one 384-tip pipetting head for starting the assay plus one 96-tip head for dispensing the resin) together with one reservoir for the Enzyme mix (3×) and one for the ATP mix (3×).

At the start of the run, the robot aspirates 5 µl of ATP mix, makes an air gap inside the tips (3 µl) and aspirates 5 µl of JAK2 mix. The following dispensation into the plates plus 3 cycles of mixing, done by the robot itself, starts the kinase reaction. At this point, the correct concentrations are restored for all the reagents.

The robot incubates the plates for 60 minutes at room temperature, and then stops the reaction by pipetting 60 µl of dowex resin suspension into the reaction mix. In order to avoid tip clogging, wide bore tips are used to dispense the resin suspension. Three cycles of mixing are done immediately after the addition of the resin.

Another mixing cycle is performed after all the plates are stopped, this time using normal tips: the plates are then allowed to rest for about one hour in order to maximize ATP capture. At this point, 27 µl of the supernatant are transferred into 384-Optiplates (Perkin-Elmer), with 50 µl of Microscint 40 (Perkin-Elmer); after 5 min of orbital shaking the plates are read on a Perkin-Elmer Top Count radioactivity counter.

Data Fitting—Data are analyzed by an internally customized version of the SW package "Assay Explorer" that provides sigmoidal fitting of the ten-dilutions curves for IC$_{50}$ determination in the secondary assays/hit confirmation routines.

Preparation of IGF-1R for Use in Biochemical Assay

Cloning and Expression

Human cDNA was used as template for amplification by polymerase chain reaction (PCR) of the predicted cytoplasmic portion of IGF-1R (amino acid residues 960-1367 of precursor protein; see NCBI Entrez Protein Accession #P08069) which includes the entire kinase domain. PCR was conducted using the forward primer sequence

[SEQ ID NO: 3]
5'-CTCGGATCCAGAAAGAGAAATAACAGCAGGCTG-3' and
the reverse primer sequence

[SEQ ID NO: 4]
5'-CTCGGATCCTCAGCAGGTCGAAGACTGGGGCAGCGG-3'.

In order to facilitate subsequent cloning steps, both primers comprise a BamHI restriction endonuclease site sequence. This PCR product was cloned in frame using BamHI sticky ends into a transfer vector for the baculovirus expression system, pVL1392 (Pharmingen), previously modified by insertion into the pVL1392 multiple cloning site of sequences encoding Glutathione S-transferase (GST) fusion protein, PreScission protease cleavage site and partial MCS cassette derived from the pGex-6P plasmid (Amersham BioSciences). Insertion of the IGF-1R PCR product described above into the pGex-6P derived BamHI site of the modified pVL1392 vector results in an open reading frame corresponding to the pGEX-6P GST protein and PreScission peptide fused with the human IGF-1R cytoplasmic domain. In order to obtain fusion protein, Sf21 insect cells (Invitrogen) are cotransfected with 2 microg of purified plasmid and 1 microg of virus DNA (BaculoGold™ Transfection Kit, Pharmingen), as described in the Baculovirus Instruction manual (Pharmingen). A first amplification of the virus is performed using 600 microL of cotransfected virus on 6×10$^6$ Sf21 in a monolayer culture, in 12 mL of medium (TNM-FH Grace's medium—Pharmingen). After 3 days the medium is collected, centrifuged and transferred to a sterile tube. A second amplification is prepared with the same method using 2 mL on 3×10$^7$ cells, diluted in 40 mL of medium. For the third amplification of virus, 1 mL of supernatant from the second round are used per 3×10$^7$ cells diluted in 40 mL of medium.

Protein expression is performed in H5 insect cells infected with 14 mL virus/1×10$^9$ insect cells (MOI=1.5) for 65 h with shaking at 27° C. Cells are harvested by centrifugation at 1200×g for 10 minutes.

Protein Purification

Cells were resuspended in phosphate buffered saline solution (PBS), 20 mM dithiothreitol (DTT), 0.2% CHAPS, 20% glycerol, 1 mM OVA, "Complete" protease inhibitor cocktail (1 tablet/50 mL buffer; Roche Diagnostics, Milan, Italy) and lysed by liquid extrusion with a Gaulin homogenizer (Niro Soavi, Italy). The lysate was centrifuged at 14000×g for 45 minutes and the supernatant was loaded onto a column containing 10 mL Glutathione Sepharose (Amersham Biosciences). The column was first washed with PBS buffer for 5 column volumes, then with 100 mM Tris pH 8.0, 20% glycerol for 5 column volumes, and lastly eluted with 10 mM glutathione in 100 mM Tris pH 8.0, 20% glycerol. Fractions of 10 mL were collected, and protein-rich fractions were pooled. Typically, 20 mg of fusion protein were recovered from $1 \times 10^9$ cells, and this was typically >85% pure as judged by SDS-PAGE followed by Coomassie staining. Purified protein was stored at −80° C. prior to its use in biochemical assays.

Biochemical Assay for Inhibitors of IGF-1R Kinase Activity

The inhibitory activity of putative kinase inhibitors and the potency of selected compounds were determined using a trans-phosphorylation assay.

A specific substrate was incubated with the kinase in appropriate buffer conditions in the presence of ATP traced with $^{33}$P-γ-ATP (gamma phosphate-labeled, Redivue™ Code Number AH9968, 1000-3000Ci/mmole, Amersham Biosciences Piscataway, N.J., USA), optimal cofactors and test compound.

At the end of the phosphorylation reaction, more than 98% cold and radioactive ATP were captured by an excess of Dowex ion exchange resin. The resin was allowed to settle to the bottom of reaction wells by gravity. Supernatant, containing substrate peptide, was subsequently withdrawn and transferred into a counting plate, and radioactivity (corresponding to phosphate incorporated into peptide) was evaluated by β-counting.

Reagents/Assay Conditions i. Dowex Resin Preparation 500 g of wet resin (SIGMA, custom prepared DOWEX resin 1×8 200-400 mesh, 2.5 Kg) were weighed out and diluted to 2 L in 150 mM sodium formate, pH 3.00.

The resin was allowed to settle for several hours and then the supernatant was discarded. This washing procedure was repeated three times over two days. Finally, the resin was allowed to settle, supernatant was discarded and two volumes (with respect to the resin volume) of 150 mM sodium formate buffer were added. The final pH was circa 3.0.

The washed resin was kept at 4° C. before use, and was stable for more than one week.

ii. Kinase Buffer (KB)

Kinase buffer was composed of 50 mM HEPES pH 7.9 containing 3 mM $MnCl_2$, 1 mM DTT, 3 microM $Na_3VO_4$, and 0.2 mg/mL BSA. 3× KB is buffer of the same composition and pH as KB, but with three times the concentration of each component.

iii. Enzyme Pre-Activation and Preparation of 3× Enzyme Mix.

Prior to starting the kinase inhibition assay, IGF-1R was pre-phosphorylated in order to linearize reaction kinetics. To achieve this, the desired total quantity of enzyme was prepared at an enzyme concentration of 360 nM in KB containing 100 microM ATP, and this preparation was incubated for 30 min at 28° C. 3× Enzyme Mix was obtained by diluting this preactivated enzyme 20-fold in 3× KB.

iv. Assay Conditions

The kinase assay was run with a final enzyme concentration of 6 nM, in the presence of 6 microM ATP, 1 nM $^{33}$P-γ-ATP and 10 microM substrate, a carboxy-terminally biotinylated peptide of the following sequence: KKKSPGEYVNIEFGGGGK-biotin. The peptide was obtained in batches of >95% peptide purity from American Peptide Company, Inc. (Sunnyvale, Calif., USA).

Robotized Dowex Assay

Test reactions were performed in a total final volume of 21 microL consisting of:

a) 7 microL/well of 3× Enzyme Mix (18 nM preactivated enzyme in 3× kinase buffer), b) 7 microL/well of 3× substrate/ATP mix (30 microM substrate, 18 microM ATP, 3 nM $^{33}$P-γ-ATP in double-distilled water ($ddH_2O$), c) 7 microL/well 3× test compounds diluted into $ddH_2O$-3% DMSO.

Compound Dilution and Assay Scheme is Reported Below.

i. Dilution of Compounds 10 mM stock solutions of test compounds in 100% DMSO were distributed into 96 well 12×8 format microtiter plates.

For % inhibition studies, dilution plates at 1 mM, 100 microM and 10 microM were prepared in 100% DMSO, then diluted to 3× final desired concentration (30, 3 and 0.3 microM) in $ddH_2O$, 3% DMSO. A Multimek 96 (Beckman Coulter, Inc. 4300 N. Harbor Boulevard, P.O. Box 3100 Fullerton, Calif. 92834-3100 USA) was used for compound pipetting into test plates.

For $IC_{50}$ determination, starting solutions of 30 microM compound in 3% DMSO were derived from 1 mM/100% DMSO stock solutions. These 30 microM starting solutions were used for generation of a further 9 serial ⅓ dilutions in $ddH_2O$, 3% DMSO, so as to generate a 10-point dilution curve at 3× the final assay concentration. Serial dilution was conducted in 96-well plates using a Biomek 2000 (Beckman Coulter) system. Dilution curves of 7 compounds/plate were prepared, and each plate also included a 10-point dilution curve of Staurosporine, as well as several negative and positive control wells.

ii. Assay Scheme 7 microL of each test compound dilution (or control) in $ddH_2O$, 3% DMSO were pipetted into each well of a 384-well, V-bottom assay plate, which was then transferred to a PlateTrak 12 robotized station (Perkin Elmer, 45 William Street Wellesley, Mass. 02481-4078, USA) equipped with one 384-tip pipetting head for starting the assay, plus one 96-tip head for dispensing the resin) prepared with reservoirs containing sufficient 3× Enzyme mix and 3×ATP mix (3×) to complete the assay run.

At the start of the assay the liquid handling system aspirates 7 microL of ATP mix, introduces an air gap inside the tips (5 microL) and then aspirates 7 microL of 3× Enzyme Mix. To start the reaction, tips contents were dispensed into the test wells already containing 7 microL test compound (at 3× desired final concentration), followed by 3 cycles of mixing, so as to restore desired final concentration for all reaction components.

Plates were incubated for 60 minutes at room temperature, and then the reaction was stopped by pipetting 70 microL of Dowex resin suspension into the reaction mix, followed by three cycles of mixing. After stopping the reaction, plates were allowed to rest for one hour in order to maximize ATP capture. At this point, 20 microL of supernatant were transferred from each well into wells of 384-Optiplates (Perkin Elmer) containing 70 microL/well of Microscint 40 (Perkin Elmer); after 5 min of orbital shaking the plates were read on a Perkin-Elmer Top Count radioactivity counter.

iii. Data Analysis

Data were analysed using a customized version of the "Assay Explorer" software package (Elsevier MDL, San Leandro, Calif. 94577). For single compound concentrations, inhibitory activity was typically expressed as % inhibition obtained in presence of compound, compared to total activity of enzyme obtained when inhibitor is omitted.

Compounds showing desired inhibition were further analysed in order to study the potency of the inhibitor through $IC_{50}$ calculation. In this case, inhibition data obtained using serial dilutions of the inhibitor were fitted by non-linear regression using the following equation:

$$v = v_0 + \frac{(v_0 - v_b)}{1 + 10^{n(\log IC_{50} - \log[I])}}$$

where $v_b$ is the baseline velocity, v is the observed reaction velocity, $v_o$ is the velocity in the absence of inhibitors, and [I] is the inhibitor concentration.

Cell-Based Assays for Inhibitors of IGF-1R Kinase Activity

Western Blot Analysis of Receptor Phosphorylation Following Stimulation with IGF-1 in MCF-7 Human Breast Cancer Cells MCF-7 cells (ATCC# HTB-22) were seeded in 12-well tissue culture plates at $2\times10^5$ cells/well in E-MEM medium (MEM+Earle's BSS+2 mM glutamine+0.1 mM non-essential amino acids)+10% FCS, and incubated overnight at 37° C., 5% CO2, 100% relative humidity. Cells were then starved by replacing E-MEM+10% FCS with E-MEM+0.1% BSA, and incubating overnight. After this incubation, wells were treated with desired concentrations of compound for 1 hour at 37° C., and were then stimulated with 10 nM recombinant human IGF-1 (Invitrogen, Carlsbad, Calif., USA) for 10 minutes at 37° C. Cells were then washed with PBS and lysed in 100 microL/well cell lysis buffer (M-PER Mammalian Protein Extraction Reagent [Product #78501, Pierce, Rockford, Ill., USA]+10 mM EDTA+Protease inhibitor cocktail [Sigma-Aldrich product #P8340]+phosphatase inhibitor cocktail [Sigma-Aldrich products #P2850+#P5726]). Cell lysates were cleared by centrifugation at 10,000×g for 5 minutes, and 10 microg/lane of cleared lysate protein were run on NuPAGE gels (NuPAGE 4-12% 10-lane Bis-Tris gels, Invitrogen) with MOPS running buffer, then transferred onto Hybond-ECL nitrocellulose filters (Amersham Biosciences, Little Chalfont, Buckinghamshire, UK) using Mini PROTEAN II chambers (Bio-Rad Laboratories, Hercules, Calif., USA). Filters bearing transferred protein were incubated for 1 hour in blocking buffer (TBS+5% BSA+0.15% Tween 20), and probed for 2 hours in the same buffer containing 1/1000 rabbit anti-phospho IGF-1R Tyr1131/InsR Tyr 1146 antibody (product #3021, Cell Signaling Technology, Beverly, Mass., USA) for the detection of phosphorylated IGF-1R, or 1/1000 dilution of rabbit IGF-Irβ(H-60) antibody (product #sc-9038, Santa Cruz Biotechnology, Inc., Santa Cruz, Calif., USA) for detecting total IGF-1R β chain. In either case, filters were then washed for 30 minutes with several changes of TBS+ 0.15% Tween 20, and incubated for 1 hour in washing buffer containing 1/5000 dilution of horseradish peroxidase conjugated anti-rabbit IgG (Amersham, product #NA934), then were washed again and developed using the ECL chemiluminescence system (Amersham) according to manufacturer's recommendations. Unless otherwise stated, reagents used were from Sigma-Aldrich, St. Louis, Mo., USA.

Growth Factor Induced S6 Ribosomal Protein Phosphorylation in Primary Human Fibroblasts Phosphorylation of S6 ribosomal protein in response to growth factor stimulation of normal human dermal fibroblasts (NHDF) was used to assess compound potency in inhibiting IGF-1 induced signal transduction in cells, and selectivity towards EGF and PDGF stimulus. NHDF cells obtained from PromoCell (Heidelberg, Germany), were maintained at 37° C. in a humidified atmosphere with 5% $CO_2$ in complete Fibroblast Growth Medium (PromoCell). For assay, NHDF were seeded in 384-well tissue culture plates (clear- and flat-bottomed black plates; Matrix Technologies Inc., Hudson, N.H., USA) at a density of 5000 cells/well in serum-free medium containing 0.1% bovine serum albumin (BSA) and incubated for 5 days. Starved cells were treated for 1 hour with desired doses of compounds and then stimulated for a further 2 hours with either 10 nM IGF-1 (Invitrogen Corp., CA, USA), 10 nM EGF (Gibco BRL, USA) or 1 nM PDGF-B/B (Roche Diagnostics GmbH, Germany). Cells were then fixed in PBS/3.7% paraformaldehyde for 20 minutes at room temperature, washed ×2 with PBS, and permeabilized with PBS/0.3% Triton X-100 for 15 minutes. Wells were then saturated with PBS/1% non-fat dry milk (Bio-Rad Laboratories, Hercules, Calif., USA) for 1 hour, and then probed for 1 hour at 37° C. with anti-phospho-S6 (Ser 235/236) antibody (Cell Signaling Technology, Beverly, Mass., USA, cat. #2211) at 1/200 dilution in PBS/1% milk/ 0.3% Tween 20. Wells were then washed twice with PBS, and incubated for 1 hour at 37° C. with PBS/1% milk/0.3% Tween 20+1 microg/mL DAPI (4,6-diamidino-2-phenylindole)+1/ 500 Goat anti-rabbit Cy5™-conjugated secondary antibody (Amersham Biosciences, Little Chalfont, Buckinghamshire, UK). Wells were then washed ×2 with PBS, and and 40 microL PBS are left in each well for immunofluorescence analysis. Fluorescence images in the DAPI and Cy5™ channels were automatically acquired, stored and analysed using a Cellomics ArrayScan™ IV instrument (Cellomics, Pittsburgh, USA); the Cellomics Cytotoxicity Algorithm was used to quantify cytoplasmic fluorescence associated with phospho-S6 (Cy5™ signal parameter: "Mean Lyso Mass-pH") for each cell in 10 fields/well, and eventually expressed as a mean population value. Unless otherwise stated, reagents were obtained from Sigma-Aldrich, St. Louis, Mo., USA.

The compounds of formula (I) tested as described above, resulted to possess a remarkable ALK, IGF-1R and JAK-2 inhibitory activity. In biochemical assays the inhibitory activity is tipically lower than 0.3 microM.

See, as an example, the following Table I reporting the experimental data of some representative compounds of the invention being tested in biochemical assay as ALK, IGF-1R and JAK-2 kinase inhibitors ($IC_{50}$ μM) in comparison with the closest compound of the prior art (Ref. compound), described in WO 03/028720, page 72, Table XI, compound A07-M1-B01.

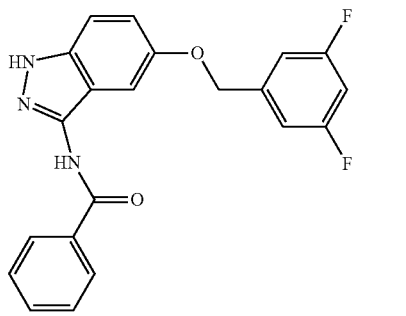

Ref. Compound

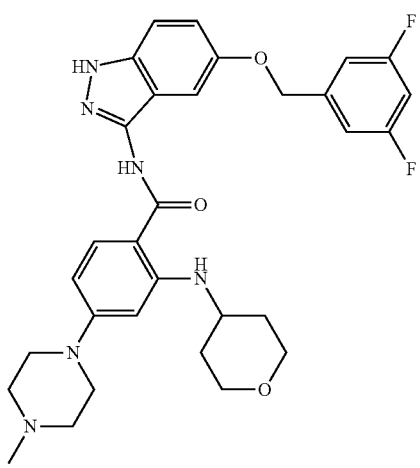

Cpd. 8

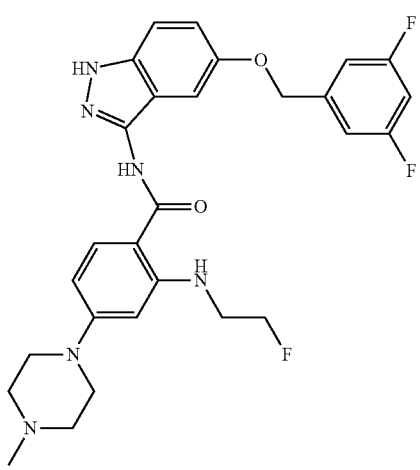

Cpd. 36

TABLE 1

| Cpd No. | ALK IC$_{50}$ (µM) Biochemical assay | IGF-1R IC$_{50}$ (µM) Biochemical assay | JAK2 IC$_{50}$ (µM) Biochemical assay |
|---|---|---|---|
| 8 | 0.02 | 0.14 | 0.02 |
| 36 | 0.01 | 0.20 | 0.01 |
| Ref. compound | 1.87 | >10 | 0.22 |

The compounds of the present invention can be administered either as single agents or, alternatively, in combination with known anticancer treatments such as radiation therapy or chemotherapy regimen in combination with cytostatic or cytotoxic agents, antibiotic-type agents, alkylating agents, antimetabolite agents, hormonal agents, immunological agents, interferon-type agents, cyclooxygenase inhibitors (e.g. COX-2 inhibitors), matrixmetalloprotease inhibitors, telomerase inhibitors, tyrosine kinase inhibitors, anti-growth factor receptor agents, anti-HER agents, anti-EGFR agents, anti-angiogenesis agents (e.g. angiogenesis inhibitors), farnesyl transferase inhibitors, ras-raf signal transduction pathway inhibitors, cell cycle inhibitors, other cdks inhibitors, tubulin binding agents, topoisomerase I inhibitors, topoisomerase II inhibitors, and the like.

If formulated as a fixed dose, such combination products employ the compounds of this invention within the dosage range described below and the other pharmaceutically active agent within the approved dosage range.

Compounds of the formula (I) may be used sequentially with known anticancer agents when a combination formulation is inappropriate.

The compounds of the formula (I) of the present invention, suitable for administration to a mammal, e.g., to humans, can be administered by the usual routes and the dosage level depends upon the age, weight, conditions of the patient and administration route.

For example, a suitable dosage adopted for oral administration of a compound of the formula (I) may range from about 10 to about 500 mg per dose, from 1 to 5 times daily. The compounds of the invention can be administered in a variety of dosage forms, e.g., orally, in the form tablets, capsules, sugar or film coated tablets, liquid solutions or suspensions; rectally in the form suppositories; parenterally, e.g., intramuscularly, or through intravenous and/or intrathecal and/or intraspinal injection or infusion.

The present invention also includes pharmaceutical compositions comprising a compound of the formula (I) or a pharmaceutically acceptable salt thereof in association with a pharmaceutically acceptable excipient, which may be a carrier or a diluent.

The pharmaceutical compositions containing the compounds of the invention are usually prepared following conventional methods and are administered in a suitable pharmaceutical form. For example, the solid oral forms may contain, together with the active compound, diluents, e.g., lactose, dextrose saccharose, sucrose, cellulose, corn starch or potato starch; lubricants, e.g., silica, talc, stearic acid, magnesium or calcium stearate, and/or polyethylene glycols; binding agents, e.g., starches, arabic gum, gelatine methylcellulose, carboxymethylcellulose or polyvinyl pyrrolidone; disintegrating agents, e.g., starch, alginic acid, alginates or sodium starch glycolate; effervescing mixtures; dyestuffs; sweeteners; wetting agents such as lecithin, polysorbates, laurylsulphates; and, in general, non-toxic and pharmacologically inactive substances used in pharmaceutical formulations. These pharmaceutical preparations may be manufactured in known manner, for example, by means of mixing, granulating, tabletting, sugar-coating, or film-coating processes.

The liquid dispersions for oral administration may be, e.g., syrups, emulsions and suspensions. As an example, the syrups may contain, as carrier, saccharose or saccharose with glycerine and/or mannitol and sorbitol.

The suspensions and the emulsions may contain, as examples of carriers, natural gum, agar, sodium alginate, pectin, methylcellulose, carboxymethylcellulose, or polyvinyl alcohol. The suspension or solutions for intramuscular injections may contain, together with the active compound, a pharmaceutically acceptable carrier, e.g., sterile water, olive oil, ethyl oleate, glycols, e.g., propylene glycol and, if desired, a suitable amount of lidocaine hydrochloride.

The solutions for intravenous injections or infusions may contain, as a carrier, sterile water or preferably they may be in the form of sterile, aqueous, isotonic, saline solutions or they may contain propylene glycol as a carrier.

The suppositories may contain, together with the active compound, a pharmaceutically acceptable carrier, e.g., cocoa butter, polyethylene glycol, a polyoxyethylene sorbitan fatty acid ester surfactant or lecithin.

With the aim of better illustrating the present invention, without posing any limitation to it, the following examples are now given.

EXPERIMENTAL SECTION

For a reference to any specific compound of formula (I) of the invention, optionally in the form of a pharmaceutically acceptable salt, see the experimental section and claims. Referring to the examples that follow, compounds of the present invention were synthesized using the methods described herein, or other methods, which are well known in the art.

The short forms and abbreviations used herein have the following meaning:

g (grams) mg (milligrams)

ml (milliliters) mM (millimolar)

μM (micromolar) mmol (millimoles)

h (hours) MHz (Mega-Hertz)

mm (millimetres) Hz (Hertz)

M (molar) min (minutes)

mol (moles) TLC (thin layer chromatography)

r.t. (room temperature) TEA (triethylamine)

TFA (trifluoroacetic acid) DMF (N,N-dimethyl formamide)

DIPEA (N,N-diisopropyl-N-ethylamine) DCM (dichloromethane)

THF (tetrahydrofuran) Hex (hexane)

MeOH (Methanol) DMSO (dimethylsulfoxide)

EtOAc (Ethyl acetate) b. s. (broad singlet)

TBDMS (dimethyl-tert-butylsilyl) Ac (acetyl)

Boc=(tert-butyloxycarbonyl) $Ac_2O$ acetic anhydride

NaH=sodium hydride, 60% in mineral oil ESI=electrospray ionization

RP-HPLC (reverse phase high performance liquid chromatography)

With the aim to better illustrate the present invention, without posing any limitation to it, the following examples are now given.

As used herein the symbols and conventions used in the processes, schemes and examples are consistent with those used in the contemporary scientific literature, for example, the *Journal of the American Chemical Society* or the *Journal of Biological Chemistry*.

Unless otherwise noted, all materials were obtained from commercial suppliers, of the best grade and used without further purification. Anhydrous solvent such as DMF, THF, $CH_2Cl_2$ and toluene were obtained from the Aldrich Chemical Company. All reactions involving air- or moisture-sensitive compounds were performed under nitrogen or argon atmosphere.

General Purification and Analytical Methods

Flash Chromatography was performed on silica gel (Merck grade 9395, 60A). HPLC was performed on Waters X Terra RP 18 (4.6×50 mm, 3.5 μm) column using a Waters 2790 HPLC system equipped with a 996 Waters PDA detector and Micromass mod. ZQ single quadrupole mass spectrometer, equipped with an electrospray (ESI) ion source. Mobile phase A was ammonium acetate 5 mM buffer (pH 5.5 with acetic acid-acetonitrile 95:5), and Mobile phase B was water-acetonitrile (5:95). Gradient from 10 to 90% B in 8 minutes, hold 90% B 2 minutes. UV detection at 220 nm and 254 nm. Flow rate 1 mL/min. Injection volume 10 microL. Full scan, mass range from 100 to 800 amu. Capillary voltage was 2.5 KV; source temperature was 120° C.; cone was 10 V. Retention times (HPLC r.t.) are given in minutes at 220 nm or at 254 nm. Mass are given as m/z ratio.

When necessary, compounds were purified by preparative HPLC on a Waters Symmetry C18 (19×50 mm, 5 um) column or on a Waters X Terra RP 18 (30×150 mm, 5 μm) column using a Waters preparative HPLC 600 equipped with a 996 Waters PDA detector and a Micromass mod. ZMD single quadrupole mass spectrometer, electron spray ionization, positive mode. Mobile phase A was water-0.01% trifluoroacetic acid, and mobile phase B was acetonitrile. Gradient from 10 to 90% B in 8 min, hold 90% B 2 min. Flow rate 20 mL/min. In alternative, mobile phase A was water-0.1% $NH_3$, and mobile phase B was acetonitrile. Gradient from 10 to 100% B in 8 min, hold 100% B 2 min. Flow rate 20 mL/min.

1H-NMR spectrometry was performed on a Mercury VX 400 operating at 400.45 MHz equipped with a 5 mm double resonance probe [1H (15N-31P) ID_PFG Varian].

Preparation 1

Step a

Preparation of
5-[(3,5-difluorobenzyl)oxy]-2-nitrobenzonitrile

A solution of 5-fluoro-2-nitrobenzonitrile (60 g, 354 mmol), (3,5-difluorophenyl)methanol (52.14 mL, 460 mmol) and cesium carbonate (155 g, 460 mmol) in dry DMF (720 mL) was stirred at 70° C. for 6 hours. The reaction mixture was cooled at room temperature and poured into water (7 L) under stirring. The so obtained precipitated was filtered, washed with water and dried under vacuum at 50° C., affording 95 g (yield 92%) of the title compound.

1H-NMR (400 MHz), δ (ppm, DMSO-$d_6$): 5.37 (s, 2H) 7.18-7.30 (m, 3H) 7.55 (dd, J=9.27, 2.80 Hz, 1H) 7.86 (d, J=2.80 Hz, 1H) 8.39 (d, J=9.27 Hz, 1H)

Operating in an analogous way, the following compounds were obtained:

5-(benzyloxy)-2-nitrobenzonitrile

1H-NMR (400 MHz), δ (ppm, DMSO-$d_6$): 5.32 (s, 2H) 7.36-7.56 (m, 6H) 7.82 (d, J=2.82 Hz, 1H) 8.35 (d, J=9.31 Hz, 1H)

5-[(2,5-difluorobenzyl)oxy]-2-nitrobenzonitrile

1H-NMR (400 MHz), δ (ppm, DMSO-$d_6$): 5.38 (s, 2H) 7.34 (m, 2H) 7.50 (m, 1H) 7.59 (dd, J=9.33, 2.87 Hz, 1H) 7.91 (d, J=2.80 Hz, 1H) 8.40 (d, J=9.27 Hz, 1H)

5-[(3-fluorobenzyl)oxy]-2-nitrobenzonitrile

ESI (+) MS m/z 273 (MH$^+$)

5-[(2-chloro-3,6-difluorobenzyl)oxy]-2-nitrobenzonitrile

ESI (+) MS m/z 325 (MH$^+$)

5-[1-(3,5-difluorophenyl)ethoxy]-2-nitrobenzonitrile

ESI (+) MS m/z 305 (MH+)

2-nitro-5-[(3-phenoxybenzyl)oxy]benzonitrile

ESI (+) MS m/z 347 (MH+)

Step b

Preparation of
2-amino-5-[(3,5-difluorobenzyl)oxy]benzonitrile

A mixture of 5-[(3,5-difluorobenzyl)oxy]-2-nitrobenzonitrile (1 g, 3.44 mmol) and palladium 5% on carbon (150 mg) in 1,4-dioxane (20 mL) was treated under hydrogen atmosphere (40 psi) at room temperature. After 4 hours, the mixture was filtered on a celite pad and evaporated to dryness affording 770 mg (yield 86%) of the title compound.

1H-NMR (400 MHz), δ (ppm, DMSO-$d_6$): 5.03 (s, 2H) 5.63 (s, 2H) 6.77 (d, J=9.15 Hz, 1H), 7.04-7.06 (m, 1H) 7.07-7.12 (m, 1H) 7.11-7.15 (m, 2H) 7.16-7.22 (m, 1H)

Operating in an analogous way, the following compounds were obtained:

2-amino-5-(benzyloxy)benzonitrile

1H-NMR (400 MHz), δ (ppm, DMSO-$d_6$): 4.97 (s, 2H) 5.57 (br. s., 2H) 6.74 (d, J=8.92 Hz, 1H) 7.03 (m, 2H) 7.30-7.40 (m, 5H)

2-amino-5-[(2,5-difluorobenzyl)oxy]benzonitrile

1H-NMR (400 MHz), δ (ppm, DMSO-$d_6$): 5.03 (s, 2H) 5.65 (s, 2H) 6.76-6.79 (m, 1H) 7.08-7.12 (m, 2H), 7.22-7.27 (m, 1H) 7.28-7.34 (m, 1H) 7.35-7.41 (m, 1H)

2-amino-5-[(3-fluorobenzyl)oxy]benzonitrile

ESI (+) MS m/z 243 (MH+)

2-amino-5-[(2-chloro-3,6-difluorobenzyl)oxy]benzonitrile

ESI (+) MS m/z 295 (MH+)

2-amino-5-[1-(3,5-difluorophenyl)ethoxy]benzonitrile

ESI (+) MS m/z 275 (MH+)

2-amino-5-[(3-phenoxybenzyl)oxy]benzonitrile

ESI (+) MS m/z 317 (MH+)

Step b

Preparation of
2-amino-5-[(3,5-difluorobenzyl)oxy]benzonitrile

A solution of 85% sodium hydrosulfite (38.1 g, 186 mmol) in water (200 mL) was added dropwise to a mixture of 5-[(3,5-difluorobenzyl)oxy]-2-nitrobenzonitrile (9 g, 31 mmol) and tetrabutylammonium chloride (5.86 g, 21.1 mmol) in dichloromethane (200 mL) under vigorous stirring. After 2 hours, the reaction mixture was cooled at 0° C. and 2N NaOH (200 mL) was added to reach a pH value of 12. The organic phase was separated and the acqueous layer was washed with dichloromethane. Organic phases were collected and treated for 3 hours with 4M hydrochloric acid in dioxane (50 mL). The reaction mixture was washed with water, NaHCO$_3$ saturated solution and brine. Organic phase was dried over sodium sulphate, filtered and evaporated to dryness affording 7.6 g (yield 94%) of the title compound.

Step c

Preparation of
5-[(3,5-difluorobenzyl)oxy]-1H-indazol-3-amine

A solution of sodium nitrite (13 gr, 190 mmol) in water (15 mL) was added dropwise to a cooled (0° C.) mixture of 2-amino-5-[(3,5-difluorobenzyl)oxy]benzonitrile (42.9 g, 165 mmol) in 37% hydrochloric acid (340 mL). After 2 hours, the resulting reaction mixture was added over a period of 1 hour to a previously prepared cooled suspension of tin(II) chloride (250 gr, 1.32 mol) in 37% hydrochloric acid (286 mL) trying to keep the temperature below 10° C. After 1 hour, the resulting reaction mixture was diluted with water (400 mL) and 35% NaOH (735 mL) was added to obtain a pH value of 9-10. The reaction mixture was extracted with EtOAc (1 L) and washed with EtOAc (2×0.5 L). Collected organic phases were dried over sodium sulfate, filtered and evaporated to dryness. The crude residue was purified by chromatography on silica gel using dichloromethane/7M NH$_3$ in MeOH 96:4 as the eluant, affording 34.7 g of the title compound (76% yield).

1H-NMR (400 MHz), δ (ppm, DMSO-$d_6$): 5.11 (s, 2H) 5.14 (s, 2H) 6.95 (dd, J=8.90, 2.44 Hz, 1H) 7.14-7.24 (m, 4H) 7.26 (d, J=2.32 Hz, 1H) 11.21 (s, 1H)

Operating in an analogous way, the following compounds were obtained:

5-(benzyloxy)-1H-indazol-3-amine

1H-NMR (400 MHz), δ (ppm, DMSO-$d_6$): 5.04 (s, 2H) 5.15 (s, 2H) 7.01 (dd, J=8.93, 2.36 Hz, 1H) 7.13 (dd, J=8.92, 0.65 Hz, 1H) 7.26-7.47 (m, 6H)

5-[(2,5-difluorobenzyl)oxy]-1H-indazol-3-amine

1H-NMR (400 MHz), δ (ppm, DMSO-$d_6$): 5.11 (s, 2H) 5.14-5.28 (m, 2H) 7.01 (dd, J=8.90, 2.44 Hz, 1H) 7.16-7.20 (m, 1H) 7.22-7.29 (m, 1H) 7.29-7.36 (m, 1H) 7.32 (d, J=1.83 Hz, 1H) 7.43 (ddd, J=8.87, 5.64, 3.17 Hz, 1H) 11.23 (br. s., 1H)

5-[(3-fluorobenzyl)oxy]-1H-indazol-3-amine

ESI (+) MS m/z 258 (MH+)

5-[(2-chloro-3,6-difluorobenzyl)oxy]-1H-indazol-3-amine

ESI (+) MS m/z 310 (MH+)

5-[1-(3,5-difluorophenyl)ethoxy]-1H-indazol-3-amine

1H-NMR (400 MHz), δ (ppm, DMSO-$d_6$):1.55 (d, J=6.46 Hz, 3H) 5.39 (q, J=6.46 Hz, 1H) 6.96 (dd, J=8.96, 2.26 Hz, 1H) 7.05-7.19 (m, 5H) 11.22 (br. s., 1H)

5-[(3-phenoxybenzyl)oxy]-1H-indazol-3-amine

ESI (+) MS m/z 332 (MH$^+$)

Preparation 2

Step a

Preparation of
5-(3,5-difluoro-phenoxy)-2-nitro-benzonitrile

5-Fluoro-2-nitro-benzonitrile (5 g, 30.1 mmol) in dry DMF (60 mL) was treated first with cesium carbonate (11.7 g, 36.12 mmol) followed by 3,5-difluoro-phenol. The reaction was stirred at room temperature for 1 hour and then poured into iced water (600 mL). After stirring for 2 hours, a pale yellow solid was filtered with suction, washed with water furnishing, after drying at 50° C. under vacuum, 7.73 g of title compound in 93% yield.

1H-NMR (400 MHz), δ (ppm, DMSO-d$_6$): 7.05-7.13 (m, 2H) 7.22 (tt, J=9.39, 2.32 Hz, 1H) 7.56 (dd, J=9.27, 2.80 Hz, 1H) 7.96 (d, J=2.56 Hz, 1H) 8.41 (d, J=9.15 Hz, 1H)

Operating in an analogous way, the following compounds were obtained:

2-nitro-5-phenoxybenzonitrile

ESI (+) MS m/z 241 (MH$^+$)

5-(3-fluorophenoxy)-2-nitrobenzonitrile

ESI (+) MS m/z 259 (MH$^+$)

5-[4-(benzyloxy)phenoxy]-2-nitrobenzonitrile

ESI (+) MS m/z 347 (MH$^+$)

2-nitro-5-(4-phenoxyphenoxy)benzonitrile

ESI (+) MS m/z 333 (MH$^+$)

5-[3-(benzyloxy)phenoxy]-2-nitrobenzonitrile

ESI (+) MS m/z 347 (MH$^+$)

Step b

Preparation of
2-amino-5-(3,5-difluorophenoxy)benzonitrile 5-(3,5-Difluoro-phenoxy)-2-nitro-benzonitrile (7.65 g, 27.7 mmol) in dioxane (80 mL) was treated with 10% Pd/C (765 mg) and hydrogenated at 45 psi. After 6 hours the reaction was filtered through a celite funnel and washed with MeOH. The volatiles were evaporated. After purification over silica gel (eluent: hexane:EtOAc 7:3), 4.82 g of title compound were obtained as a pale yellow solid in 71% yield.

1H-NMR (400 MHz), δ (ppm, DMSO-d$_6$): 6.07 (s, 2H) 6.57-6.66 (m, 2H) 6.85 (d, J=9.02 Hz, 1H) 6.91 (tt, J=9.33, 2.32 Hz, 1H) 7.16 (dd, J=9.02, 2.93 Hz, 1H) 7.27 (d, J=2.80 Hz, 1H)

Operating in an analogous way, the following compounds were obtained:

2-amino-5-phenoxybenzonitrile

ESI (+) MS m/z 211 (MH$^+$)

5-(3-fluorophenoxy)-2-aminobenzonitrile

ESI (+) MS m/z 229 (MH$^+$)

5-[4-(benzyloxy)phenoxy]-2-aminobenzonitrile

ESI (+) MS m/z 317 (MH$^+$)

2-amino-5-(4-phenoxyphenoxy)benzonitrile

ESI (+) MS m/z 303 (MH$^+$)

5-[3-(benzyloxy)phenoxy]-2-aminobenzonitrile

ESI (+) MS m/z 317 (MH$^+$)

Step c

Preparation of
5-(3,5-difluorophenoxy)-1H-indazol-3-amine

2-Amino-5-(3,5-difluoro-phenoxy)-benzonitrile (4.78 g, 19.45 mmol) was suspended in 36% hydrochloric acid (45 mL), cooled with an ice bath and treated drop wise with sodium nitrite (1.54 g, 22.37 mmol) in water (2 mL). The reaction mixture was stirred at 4° C. for 3 hours and then carefully added at this temperature to tin chloride (29.51 g, 155.62 mmol) in 36% hydrochloric acid (45 mL) at 4° C., with stirring. After two hours, 35% sodium hydroxide (110 mL) was added with cooling (final pH: 10). The grey mixture was taken up with EtOAc (100 mL), stirred for 1 hour and filtered. The grey solid was then washed thoroughly with fresh EtOAc (400 mL). The organic phase was separated, washed with brine, dried over sodium sulfate and evaporated to leave 4.5 g of a pale yellow solid. The solid was treated with 25 mL of hexane:EtOAc 7:3 and heated to reflux temperature, cooled and filtered to afford after drying at 50° C., under vacuum 3.17 g of title compound as whitish solid in 62% yield.

1H-NMR (400 MHz), δ (ppm, DMSO-d$_6$): 5.33 (s, 2H) 6.57-6.67 (m, 2H) 6.92 (tt, J=9.33, 2.32 Hz, 1H) 7.06 (dd, J=8.90, 2.32 Hz, 1H) 7.32 (dd, J=8.84, 0.55 Hz, 1H) 7.48 (d, J=2.32 Hz, 1H) 11.50 (s, 1H)

Operating in an analogous way, the following compounds were obtained:

5-phenoxy-1H-indazol-3-amine

ESI (+) MS m/z 226 (MH$^+$)

5-(3-fluorophenoxy)-1H-indazol-3-amine

ESI (+) MS m/z 244 (MH$^+$)

5-[4-(benzyloxy)phenoxy]-1H-indazol-3-amine

ESI (+) MS m/z 332 (MH$^+$)

5-(4-phenoxyphenoxy)-1H-indazol-3-amine

ESI (+) MS m/z 318 (MH$^+$)

5-[3-(benzyloxy)phenoxy]-1H-indazol-3-amine

ESI (+) MS m/z 332 (MH$^+$)

Example 1

Step d

N-{5-[(2,5-difluorobenzyl)oxy]-1H-indazol-3-yl}-4-(4-methylpiperazin-1-yl)-2-(tetrahydro-2H-pyran-4-ylamino)benzamide (Cpd. 11)

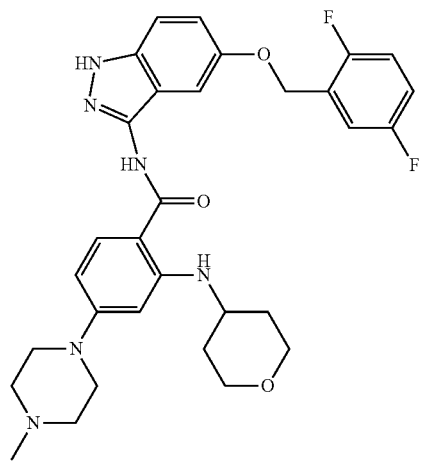 [SMILES: CN1CCN(c2ccc(C(=O)Nc3n[nH]c4ccc(OCc5cc(F)ccc5F)cc34)c(NC3CCOCC3)c2)CC1]

4-(4-Methylpiperazin-1-yl)-2-[tetrahydro-2H-pyran-4-yl(trifluoroacetyl)amino]benzoic acid hydrochloride (590 mg, 1.31 mmol) in dry DCM (10 mL), under nitrogen, was cooled with an ice bath and treated first with a drop of DMF and then with oxalyl chloride (2.62 mmol, 0.228 mmol). After stirring for 4 hours at room temperature, the solution was evaporated and the solid was dried under vacuum. The crude acid chloride was dissolved in 20 mL of dry pyridine, cooled with an ice bath and treated drop-wise with 5-[(2,5-difluorobenzyl)oxy]-1H-indazol-3-amine (300 mg, 1.09 mmol) in 15 mL of pyridine. The reaction was left overnight at 4° C. Volatiles were evaporated and the residue was diluted with water (300 mL) and extracted with EtOAc (3×300 mL). Organic phases were collected, dried over sodium sulfate and evaporated. Crude product was diluted with MeOH (10 mL) and heated at 80° C. in the presence of triethylamine (2.5 mL). After 3 hours, volatiles were evaporated and the residue was dissolved in DCM (100 mL), washed with NaHCO$_3$ saturated solution, water and brine. The organic layer was dried over sodium sulfate, filtered and evaporated under vacuum. Crude product was purified by flash chromatography over silica gel (DCM/MeOH 92:8) affording 470 mg (yield 75%) of title compound 1H-NMR (400 MHz), δ (ppm, DMSO-d$_6$): 1.29-1.44 (m, 2H) 1.88-1.99 (m, 2H) 2.25 (s, 3H) 2.46 (br. s., 4H) 3.24-3.29 (m, 4H) 3.45-3.55 (m, 2H) 3.64-3.73 (m, 1H) 3.78-3.86 (m, 2H) 5.11 (s, 2H) 6.15 (d, J=1.95 Hz, 1H) 6.25 (dd, J=9.08, 2.13 Hz, 1H) 7.09-7.14 (m, 2H) 7.21-7.27 (m, 1H) 7.27-7.34 (m, 1H) 7.41 (dd, J=8.54, 0.73 Hz, 1H) 7.40-7.45 (m, 1H) 7.80 (d, J=9.15 Hz, 1H) 8.28 (d, J=7.80 Hz, 1H) 10.06 (s, 1H) 12.59 (s, 1H)

Operating in an analogous way, the following compounds were obtained:

N-[5-(benzyloxy)-1H-indazol-3-yl]-4-(4-methylpiperazin-1-yl)benzamide (Cpd. 1)

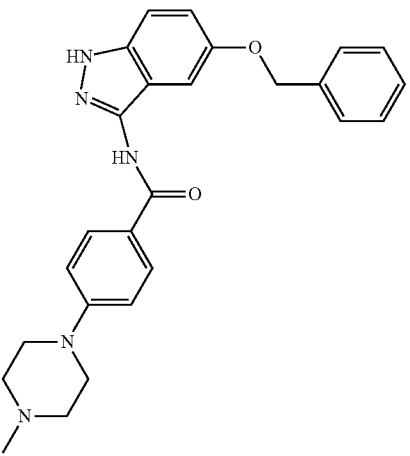 [SMILES: CN1CCN(c2ccc(C(=O)Nc3n[nH]c4ccc(OCc5ccccc5)cc34)cc2)CC1]

1H-NMR (400 MHz), δ (ppm, DMSO-d$_6$): 2.28 (s, 3H) 2.43-2.59 (m, 4H) 3.24-3.35 (m, 4H) 5.06 (s, 2H) 7.04 (d, J=9.14 Hz, 2H) 7.11 (dd, J=9.02, 2.07 Hz, 1H) 7.18 (d., J=2.19 Hz, 1H) 7.31-7.43 (m, 3H) 7.46-7.50 (m, 2H) 7.98 (m, 2H) 10.35 (br. s., 1H) 12.60 (s, 1H)

N-{5-[(3-fluorobenzyl)oxy]-1H-indazol-3-yl}-4-(4-methylpiperazin-1-yl)benzamide (Cpd. 2)

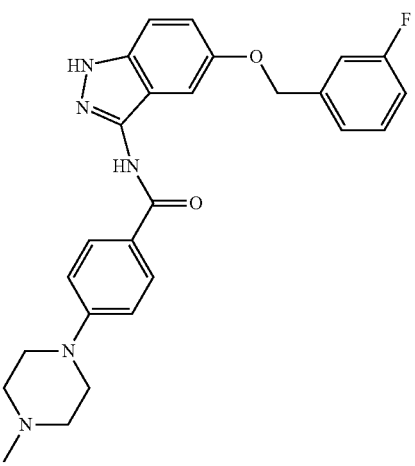 [SMILES: CN1CCN(c2ccc(C(=O)Nc3n[nH]c4ccc(OCc5cccc(F)c5)cc34)cc2)CC1]

1H-NMR (400 MHz), δ (ppm, DMSO-$d_6$): 2.35 (bs, 3H) 2.55-2.67 (m, 4H) 3.27-3.40 (m, 4H) 5.09 (s, 2H) 7.04 (d, J=9.02 Hz, 2H) 7.10-7.20 (m, 3H) 7.26-7.35 (m, 2H) 7.39-7.47 (m, 2H) 7.98 (d, J=8.90 Hz, 2H) 10.36 (s, 1H) 12.62 (s, 1H)

N-{5-[(2-chloro-3,6-difluorobenzyl)oxy]-1H-indazol-3-yl}-4-(4-methylpiperazin-1-yl)benzamide (Cpd. 4)

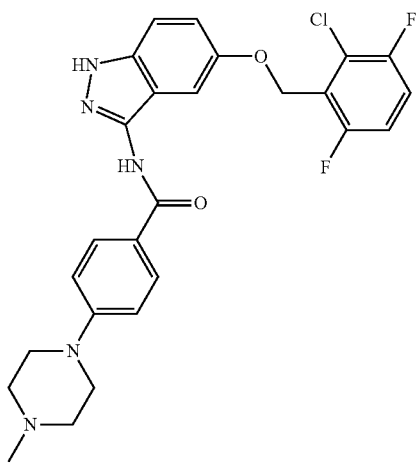 [SMILES: CN1CCN(c2ccc(C(=O)Nc3n[nH]c4ccc(OCc5c(F)ccc(F)c5Cl)cc34)cc2)CC1]

1H-NMR (400 MHz), δ (ppm, DMSO-$d_6$): 2.24 (s, 3H) 2.44-2.48 (m, 4H) 3.30 (m, 4H) 5.14 (d, J=1.46 Hz, 2H) 7.02 (d, J=9.15 Hz, 2H) 7.06 (dd, J=8.96, 2.38 Hz, 1H) 7.24 (d, J=2.32 Hz, 1H) 7.34 (m, 1H) 7.39-7.45 (m, 1H) 7.57 (d, J=4.76 Hz, 1H) 7.98 (d, J=9.02 Hz, 2H) 10.37 (s, 1H) 12.64 (s, 1H)

N-[5-(benzyloxy)-1H-indazol-3-yl]-2-[(2-methoxyethyl)amino]-4-(4-methylpiperazin-1-yl)benzamide (Cpd. 3)

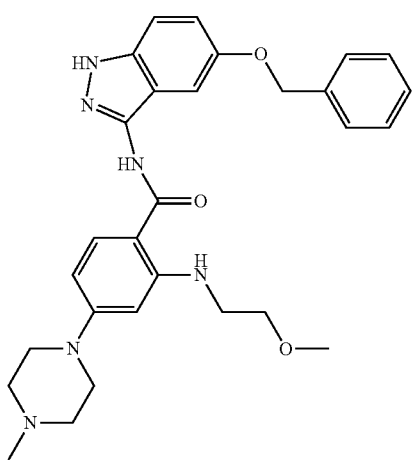 [SMILES: COCCNc1cc(N2CCN(C)CC2)ccc1C(=O)Nc1n[nH]c2ccc(OCc3ccccc3)cc12]

1H-NMR (400 MHz), δ (ppm, DMSO-$d_6$): 3.26 (s, 3H) 3.55 (t, J=5.30 Hz, 2H) 5.06 (s, 2H) 6.13 (d, J=1.95 Hz, 1H) 6.28 (dd, J=8.96, 2.13 Hz, 1H) 7.06-7.12 (m, 2H) 7.30-7.35 (m, 1H) 7.36-7.43 (m, 2H) 7.45-7.49 (m, 2H) 7.81 (d, J=9.02 Hz, 1H) 8.26 (t, J=5.12 Hz, 1H) 10.07 (s, 1H) 12.57 (s, 1H)

N-{5-[(3,5-difluorobenzyl)oxy]-1H-indazol-3-yl}-2-[(2-methoxyethyl)amino]-4-(4-methylpiperazin-1-yl)benzamide (Cpd. 5)

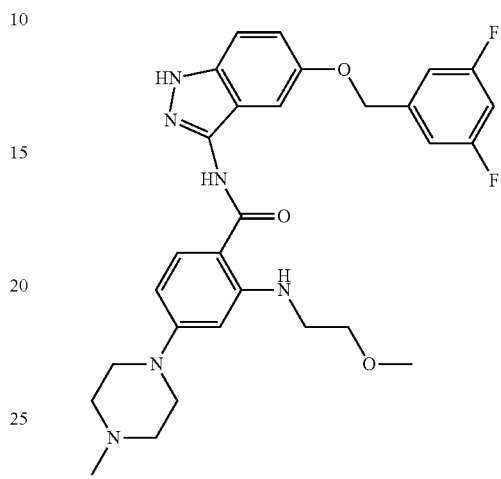

1H-NMR (400 MHz), δ (ppm, DMSO-$d_6$): 2.23 (s, 3H) 2.40-2.47 (m, 4H) 3.25 (s, 3H) 3.25-3.31 (m, 6H) 3.53 (t, J=5.30 Hz, 2H) 5.10 (s, 2H) 6.08 (d, J=2.19 Hz, 1H) 6.24 (dd, J=9.02, 2.19 Hz, 1H) 7.08 (d, J=2.19 Hz, 1H) 7.12 (dd, J=8.96, 2.38 Hz, 1H) 7.15-7.23 (m, 3H) 7.41 (d, J=9.02 Hz, 1H) 7.77 (d, J=9.15 Hz, 1H) 8.22 (t, J=5.24 Hz, 1H) 10.02 (s, 1H) 12.58 (s, 1H)

N-{5-[(3-fluorobenzyl)oxy]-1H-indazol-3-yl}-4-(4-methylpiperazin-1-yl)-2-(tetrahydro-2H-pyran-4-ylamino)benzamide (Cpd. 7)

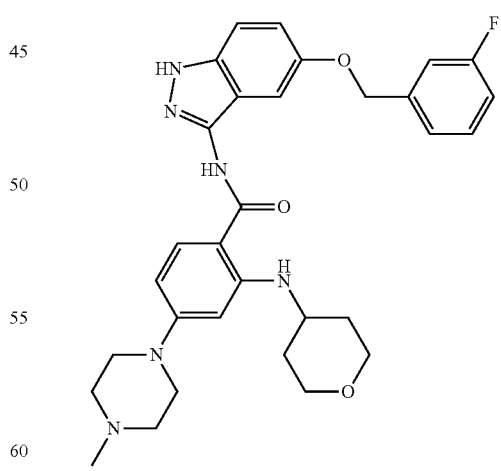

1H-NMR (400 MHz), δ (ppm, DMSO-$d_6$): 1.29-1.42 (m, 2H) 1.90-1.97 (m, 2H) 2.23 (s, 3H) 2.42-2.46 (m, 4H) 3.25 (d, J=5.24 Hz, 4H) 3.46-3.53 (m, 2H) 3.64-3.73 (m, 1H) 3.81 (ddd, J=11.58, 3.90, 3.78 Hz, 2H) 5.09 (s, 2H) 6.14 (d, 1H) 6.24 (dd, 1H) 7.07 (d, J=2.07 Hz, 1H) 7.09-7.12 (m, 1H)

7.12-7.16 (m, 1H) 7.27 (d, J=2.07 Hz, 1H) 7.30 (d, J=7.68 Hz, 1H) 7.39 (d, 1H) 7.41-7.45 (m, 1H) 7.79 (d, 1H) 8.28 (d, 1H) 10.04 (s, 1H) 12.57 (s, 1H)

N-{5-[(3,5-difluorobenzyl)oxy]-1H-indazol-3-yl}-4-(4-methylpiperazin-1-yl)-2-(tetrahydro-2H-pyran-4-ylamino)benzamide (Cpd. 8)

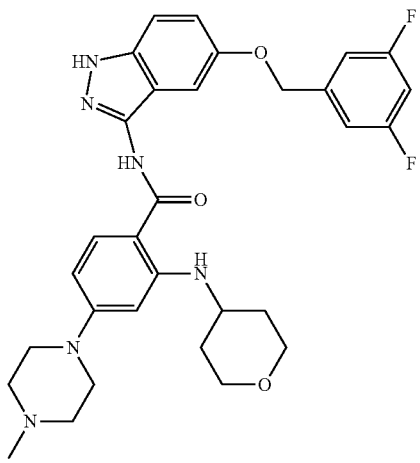 [SMILES: CN1CCN(c2ccc(C(=O)Nc3n[nH]c4ccc(OCc5cc(F)cc(F)c5)cc34)c(NC3CCOCC3)c2)CC1]

1H-NMR (400 MHz), δ (ppm, DMSO-d₆): 1.30-1.42 (m, 2H) 1.89-1.99 (m, 2H) 2.25 (s, 3H) 2.46 (br. s., 4H) 3.26 (br. s., 4H) 3.44-3.55 (m, 2H) 3.63-3.76 (m, 1H) 3.78-3.86 (m, 2H) 5.12 (s, 2H) 6.15 (d, J=1.95 Hz, 1H) 6.25 (dd, J=9.02, 2.19 Hz, 1H) 7.07 (d, J=2.19 Hz, 1H) 7.12-7.15 (m, 1H) 7.15-7.21 (m, 3H) 7.42 (d, J=9.02 Hz, 1H) 7.79 (d, J=9.15 Hz, 1H) 8.28 (d, J=7.93 Hz, 1H) 10.05 (s, 1H) 12.60 (s, 1H)

N-[5-(benzyloxy)-1H-indazol-3-yl]-4-(4-methylpiperazin-1-yl)-2-(tetrahydro-2H-pyran-4-ylamino)benzamide (Cpd. 6)

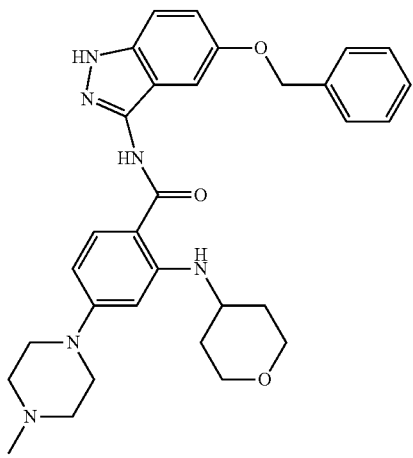 [SMILES: CN1CCN(c2ccc(C(=O)Nc3n[nH]c4ccc(OCc5ccccc5)cc34)c(NC3CCOCC3)c2)CC1]

1H-NMR (400 MHz), δ (ppm, DMSO-d₆): 1.31-1.46 (m, 2H) 1.95 (dd, J=13.66, 2.80 Hz, 2H) 2.24 (s, 3H) 2.42-2.47 (m, 4H) 3.23-3.31 (m, 4H) 3.46-3.54 (m, 2H) 3.66-3.75 (m, 1H) 3.78-3.87 (m, 2H) 5.07 (s, 2H) 6.15 (d, J=2.07 Hz, 1H) 6.25 (dd, J=8.84, 2.26 Hz, 1H) 7.07-7.12 (m, 2H) 7.29-7.35 (m, 1H) 7.36-7.42 (m, 3H) 7.45-7.49 (m, 2H) 7.80 (d, J=9.15 Hz, 1H) 8.31 (d, J=7.68 Hz, 1H) 10.04 (s, 1H) 12.57 (s, 1H)

4-(4-methylpiperazin-1-yl)-N-{5-[(3-phenoxybenzyl)oxy]-1H-indazol-3-yl}benzamide (Cpd. 39)

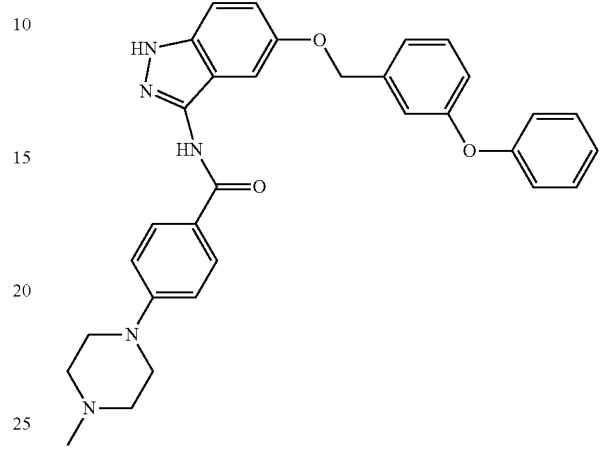

1H-NMR (400 MHz), δ (ppm, DMSO-d₆): 2.27 (s, 3H) 2.52 (m, 4H) 3.35 (m, 4H) 5.07 (s, 2H) 6.96 (m, 1H) 7.03 (m, 4H) 7.11 (m, 4H) 7.25 (m, 1H) 7.40 (m, 4H) 7.96 (d, J=9.02 Hz, 2H) 10.34 (s, 1H) 12.61 (m, 1H)

N-{5-[(3,5-difluorobenzyl)oxy]-1H-indazol-3-yl}-2-[(3-methoxypropyl)amino]-4-(4-methylpiperazin-1-yl)benzamide (Cpd. 31)

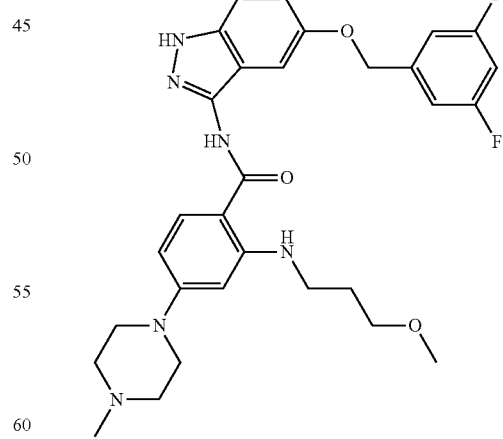

1H-NMR (400 MHz), δ (ppm, DMSO-d₆): 1.80 (quin, J=6.29 Hz, 2H) 2.23 (s, 3H) 2.42-2.47 (m, 4H) 3.15-3.21 (m, 2H) 3.22 (s, 3H) 3.25-3.29 (m, 4H) 3.42 (t, J=6/29 Hz, 2H) 5.11 (s, 2H) 6.07 (d, J=2.04 Hz, 1H) 6.24 (dd, J=8.93, 2.04 Hz, 1H) 7.09 (d, J=2.19 Hz, 1H) 7.13 (dd, J=9.02, 2.44 Hz, 1H) 7.15-7.23 (m, 3H) 7.42 (d, J=9.02 Hz, 1H) 7.80 (d, J=8.93 Hz, 1H) 8.19 (t, J=5.18 Hz, 1H) 10.05 (s, 1H) 12.58 (s, 1H)

N-{5-[(3,5-difluorobenzyl)oxy]-1H-indazol-3-yl}-2-fluoro-4-(4-methylpiperazin-1-yl)benzamide (Cpd. 33)

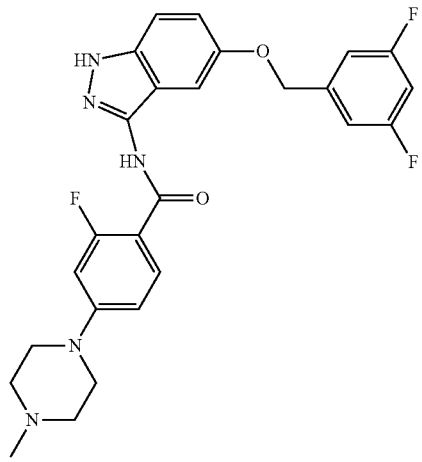 [SMILES: CN1CCN(c2ccc(C(=O)Nc3n[nH]c4ccc(OCc5cc(F)cc(F)c5)cc34)c(F)c2)CC1]

1H-NMR (400 MHz), δ (ppm, DMSO-d₆): 2.24 (s, 3H) 2.46 (br. s., 4H) 3.26-3.34 (m, 4H) 5.12 (s, 2H) 6.79-6.85 (m, 1H) 6.84-6.88 (m, 1H) 7.14 (dd, J=9.02, 2.32 Hz, 1H) 7.16-7.20 (m, 1H) 7.21 (d, J=2.20 Hz, 1H) 7.21-7.25 (m, 2H) 7.42 (d, J=9.02 Hz, 1H) 7.68 (t, J=8.84 Hz, 1H) 10.04 (d, J=3.54 Hz, 1H) 12.63 (s, 1H)

ethyl 4-{[2-({5-[(3,5-difluorobenzyl)oxy]-1H-indazol-3-yl}carbamoyl)-5-(4-methylpiperazin-1-yl)phenyl]amino}piperidine-1-carboxylate (Cpd. 35)

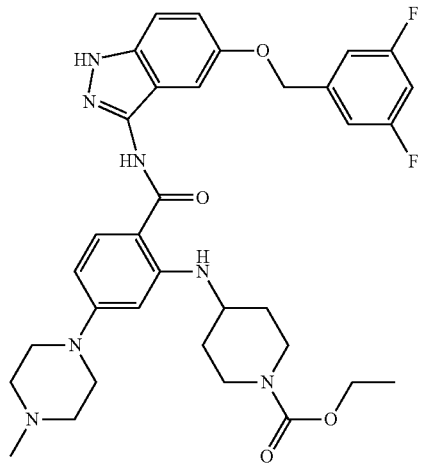 [SMILES: CCOC(=O)N1CCC(Nc2cc(N3CCN(C)CC3)ccc2C(=O)Nc2n[nH]c3ccc(OCc4cc(F)cc(F)c4)cc23)CC1]

1H-NMR (400 MHz), δ (ppm, DMSO-d₆): 1.15 (t, J=7.07 Hz, 3H) 1.22-1.33 (m, 2H) 1.89-1.97 (m, 2H) 2.25 (s, 3H) 2.42-2.49 (m, 4H) 3.09-3.19 (m, 4H) 3.26-3.31 (m, 4H) 3.66-3.72 (m, 1H) 3.72-3.81 (m, 2H) 4.01 (q, J=7.07 Hz, 2H) 5.11 (s, 2H) 6.15 (d, J=1.97 Hz, 1H) 6.25 (dd, J=8.99, 1.97 Hz, 1H) 7.06 (d, J=2.42 Hz, 1H) 7.13 (dd, J=9.02, 2.42 Hz, 1H)

7.13-7.16 (m, 1H) 7.16-7.22 (m, 2H) 7.42 (d, J=9.02 Hz, 1H) 7.80 (d, J=8.99 Hz, 1H) 8.29 (d, J=7.93 Hz, 1H) 10.06 (s, 1H) 12.60 (s, 1H)

N-{5-[(3,5-difluorobenzyl)oxy]-1H-indazol-3-yl}-2-[(1-methoxy-2-methylpropan-2-yl)amino]-4-(4-methylpiperazin-1-yl)benzamide (Cpd. 34)

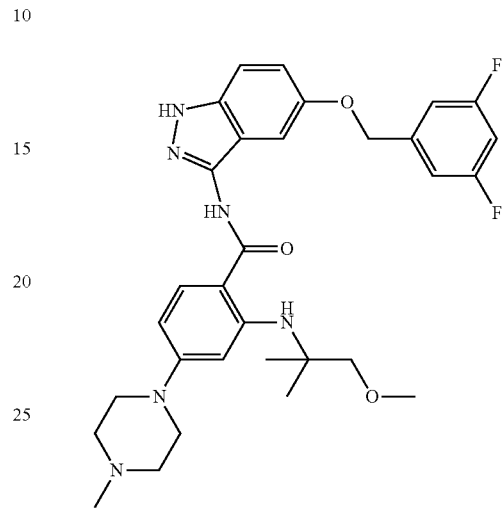

1H-NMR (400 MHz), δ (ppm, DMSO-d₆): 1.31 (s, 6H) 2.25 (s, 3H) 2.44-2.49 (m, 4H) 3.22-3.26 (m, 4H) 3.27 (s, 3H) 3.36 (s, 2H) 5.12 (s, 2H) 6.28 (dd, J=8.87, 2.26 Hz, 1H) 6.31 (d, J=2.32 Hz, 1H) 7.10 (d, J=2.19 Hz, 1H) 7.14 (dd, J=9.02, 2.44 Hz, 1H) 7.16-7.23 (m, 3H) 7.42 (d, J=9.02 Hz, 1H) 7.75 (d, J=8.87 Hz, 1H) 8.21 (s, 1H) 10.11 (s, 1H) 12.59 (s, 1H)

N-[5-(benzyloxy)-1H-indazol-3-yl]-5-(4-methylpiperazin-1-yl)-2-(tetrahydro-2H-pyran-4-ylamino)benzamide (Cpd. 9)

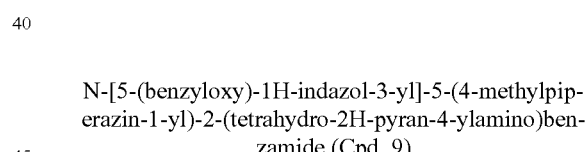
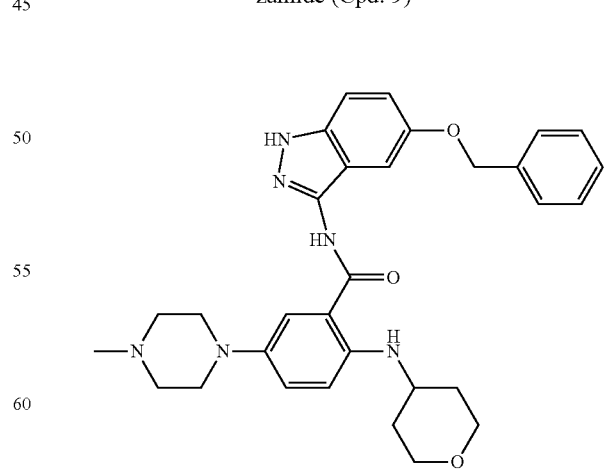

1H-NMR (400 MHz), δ (ppm, DMSO-d₆): 1.28-1.42 (m, 2H) 1.89-1.96 (m, 2H) 2.24 (s, 3H) 2.46-2.50 (m, 4H) 3.03-3.08 (m, 4H) 3.41-3.49 (m, 2H) 3.51-3.63 (m, 1H) 3.77-3.87

(m, 2H) 5.08 (s, 2H) 6.81 (d, J=9.27 Hz, 1H) 7.06-7.14 (m, 3H) 7.30-7.44 (m, 6H) 7.47 (d, J=6.83 Hz, 2H) 10.53 (s, 1H) 12.65 (s, 1H)

N-{5-[1-(3,5-difluorophenyl)ethoxy]-1H-indazol-3-yl}-4-(4-methylpiperazin-1-yl)-2-(tetrahydro-2H-pyran-4-ylamino)benzamide (Cpd. 10)

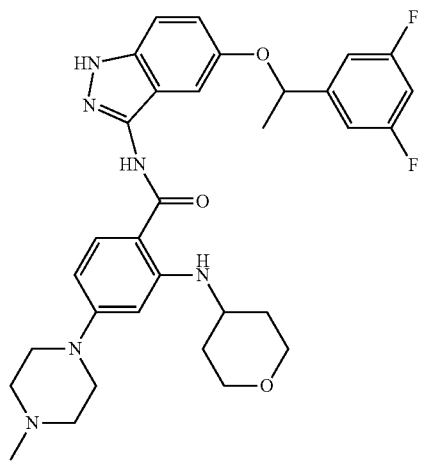 [SMILES: CC(Oc1ccc2[nH]nc(NC(=O)c3ccc(N4CCN(C)CC4)cc3NC3CCOCC3)c2c1)c1cc(F)cc(F)c1]

1H-NMR (400 MHz), δ (ppm, DMSO-d$_6$): 1.30-1.42 (m, 2H) 1.54 (d, J=6.34 Hz, 3H) 1.91-1.98 (m, 2H) 2.27 (br. s., 3H) 2.44-2.50 (m, 4H) 3.24-3.31 (m, 4H) 3.46-3.54 (m, 2H) 3.63-3.74 (m, 1H) 3.83 (d, J=10.73 Hz, 1H) 5.50 (q, J=6.30 Hz, 1H) 6.15 (d, J=1.95 Hz, 1H) 6.24 (dd, J=8.96, 2.13 Hz, 1H) 7.01 (d, J=2.19 Hz, 1H) 7.04-7.12 (m, 2H) 7.12-7.17 (m, 2H) 7.37 (d, J=8.90 Hz, 1H) 7.77 (d, J=9.02 Hz, 1H) 8.27 (d, J=7.80 Hz, 1H) 10.01 (s, 1H) 12.55 (s, 1H)

Single enantiomers (Cpd. 16 and Cpd. 17) have been obtained by preparative chiral-HPLC by using Daicel Chiralpak AD 250×20 mm 10 μm as column system and hexane/ethanol 30:70 as eluant.

N-{5-[(3,5-difluorobenzyl)oxy]-1H-indazol-3-yl}-2-[(2-fluoroethyl)amino]-4-(4-methylpiperazin-1-yl)benzamide (Cpd. 36)

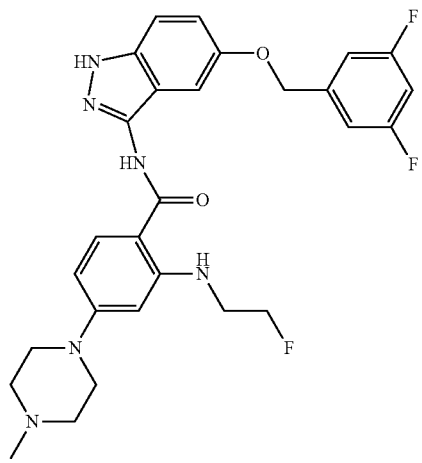 [SMILES: CN1CCN(c2ccc(C(=O)Nc3n[nH]c4ccc(OCc5cc(F)cc(F)c5)cc34)c(NCCF)c2)CC1]

1H-NMR (400 MHz), δ (ppm, DMSO-d$_6$): 2.23 (s, 3H) 2.44 (br. s., 4H) 3.28 (br. s., 4H) 3.42-3.54 (m, 2H) 4.52-4.66 (m, 2H) 5.10 (s, 2H) 6.12 (d, J=2.12 Hz, 1H) 6.27 (dd, J=8.98, 2.12 Hz, 1H) 7.07 (d, J=2.26 Hz, 1H) 7.12 (dd, J=9.05, 2.26 Hz, 1H) 7.15-7.22 (m, 3H) 7.41 (d, J=9.05, 1H) 7.80 (d, J=8.98 Hz, 1H) 8.38 (t, J=5.49 Hz, 1H) 10.10 (s, 1H) 12.61 (s, 1H)

2-(benzylamino)-N-{5-[(3,5-difluorobenzyl)oxy]-1H-indazol-3-yl}-4-(4-methylpiperazin-1-yl)benzamide (Cpd. 37)

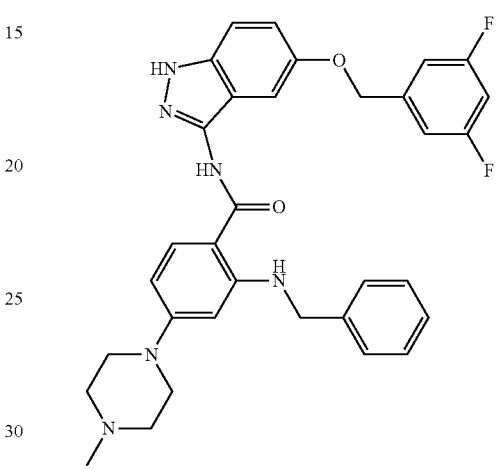

1H-NMR (400 MHz), δ (ppm, DMSO-d$_6$): 2.23 (s, 3H) 2.39-2.44 (m, 4H) 3.19-3.24 (m, 4H) 4.40 (d, J=5.37 Hz, 2H) 5.10 (s, 2H) 6.09 (d, J=2.32 Hz, 1H) 6.26 (dd, J=9.02, 2.32 Hz, 1H) 7.09 (d, J=2.07 Hz, 1H) 7.10-7.17 (m, 1H) 7.17-7.21 (m, 3H) 7.21-7.26 (m, 1H) 7.29-7.35 (m, 2H) 7.36-7.40 (m, 2H) 7.41 (d, J=9.27 Hz, 1H) 7.81 (d, J=9.15 Hz, 1H) 8.62 (t, J=5.55 Hz, 1H) 10.09 (s, 1H) 12.59 (s, 1H)

N-{5-[(3,5-difluorobenzyl)oxy]-1H-indazol-3-yl}-2-{[(2R)-1-methoxypropan-2-yl]amino}-4-(4-methylpiperazin-1-yl)benzamide (Cpd. 32)

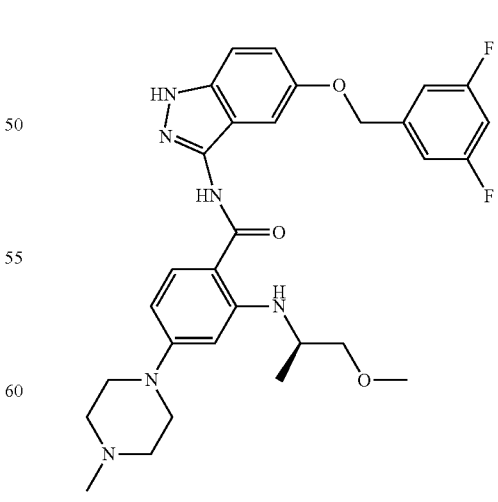

1H-NMR (400 MHz), δ (ppm, DMSO-d$_6$): 1.14 (d, J=6.46 Hz, 3H) 2.23 (s, 3H) 2.42-2.47 (m, 4H) 3.24-3.28 (m, 4H)

3.27 (s, 3H) 3.29-3.33 (m, 1H) 3.35-3.40 (m, 1H) 3.74-3.84 (m, 1H) 5.12 (s, 2H) 6.13 (d, J=2.13 Hz, 1H) 6.24 (dd, J=9.02, 2.13 Hz, 1H) 7.08 (d, J=2.29 Hz, 1H) 7.13 (dd, J=8.99, 2.29 Hz, 1H) 7.16-7.24 (m, 3H) 7.42 (d, J=8.99 Hz, 1H) 7.77 (d, J=9.02 Hz, 1H) 8.19 (d, J=7.80 Hz, 1H) 10.01 (s, 1H) 12.59 (s, 1H)

N-{5-[(3,5-difluorobenzyl)oxy]-1H-indazol-3-yl}-2-[(1,3-dimethoxypropan-2-yl)amino]-4-(4-methylpiperazin-1-yl)benzamide (Cpd. 38)

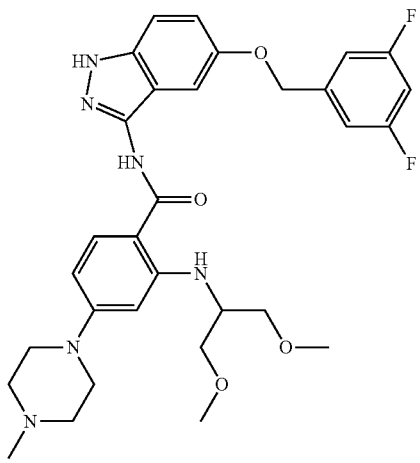 [SMILES: COCC(COC)Nc1cc(N2CCN(C)CC2)ccc1C(=O)Nc1n[nH]c2ccc(OCc3cc(F)cc(F)c3)cc12]

1H-NMR (400 MHz), δ (ppm, DMSO-d$_6$): 2.25 (s, 3H) 2.47 (m, 4H) 3.27-3.35 (m, 10H) 3.42 (d, J=5.12 Hz, 4H) 3.79-3.90 (m, 1H) 5.11 (s, 2H) 6.19 (d, J=2.07 Hz, 1H) 6.26 (dd, J=9.02, 2.19 Hz, 1H) 7.08 (d, J=2.19 Hz, 1H) 7.14 (dd, J=9.02, 2.44 Hz, 1H) 7.16-7.22 (m, 3H) 7.43 (d, J=8.90 Hz, 1H) 7.77 (d, J=9.15 Hz, 1H) 8.31 (d, J=8.05 Hz, 1H) 10.02 (s, 1H) 12.60 (s, 1H)

N-{5-[(3,5-difluorobenzyl)oxy]-1H-indazol-3-yl}-3-[(2-methoxyethyl)(methyl)amino]benzamide (Cpd. 44)

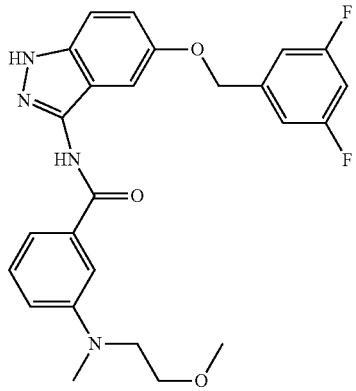 [SMILES: COCCN(C)c1cccc(C(=O)Nc2n[nH]c3ccc(OCc4cc(F)cc(F)c4)cc23)c1]

1H-NMR (400 MHz), δ (ppm, DMSO-d$_6$): 3.00 (s, 3H) 3.27 (s, 3H) 3.50-3.62 (m, 4H) 5.12 (s, 2H) 6.94 (m, 1H) 7.13-7.22 (m, 5H) 7.31 (m, 2H) 7.36 (s, 1H) 7.41-7.46 (m, 1H) 10.56 (s, 1H) 12.68 (s, 1H)

N-{5-[1-(3,5-difluorophenyl)ethoxy]-1H-indazol-3-yl}-4-(4-methylpiperazin-1-yl)benzamide (Cpd. 45)

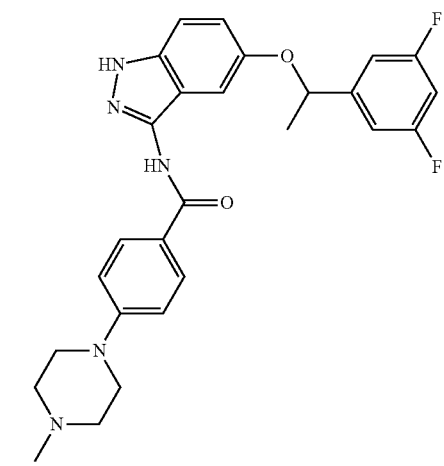 [SMILES: CC(Oc1ccc2[nH]nc(NC(=O)c3ccc(N4CCN(C)CC4)cc3)c2c1)c1cc(F)cc(F)c1]

1H-NMR (400 MHz), δ (ppm, DMSO-d$_6$): 1.54 (d, J=6.34 Hz, 3H) 2.24 (s, 3H) 2.45-2.49 (m, 4H) 3.28-3.34 (m, 4H) 5.48 (q, J=6.34 Hz, 1H) 7.02 (d, J=9.15 Hz, 2H) 7.05-7.18 (m, 5H) 7.34-7.39 (m, 1H) 7.94 (d, J=8.90 Hz, 2H) 10.30 (s, 1H) 12.57 (s, 1H)

N-{5-[1-(3,5-difluorophenyl)ethoxy]-1H-indazol-3-yl}-3-(4-methylpiperazin-1-yl)benzamide (Cpd. 46)

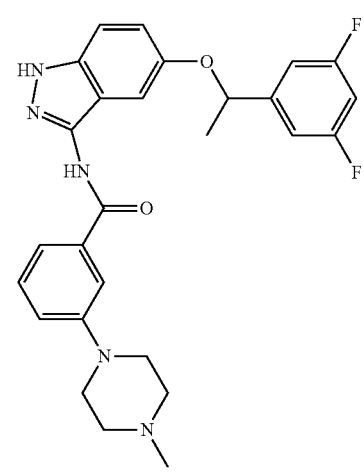 [SMILES: CC(Oc1ccc2[nH]nc(NC(=O)c3cccc(N4CCN(C)CC4)c3)c2c1)c1cc(F)cc(F)c1]

1H-NMR (400 MHz), δ (ppm, DMSO-d$_6$): 1.55 (d, J=6.34 Hz, 3H) 2.26 (s, 3H) 2.47-2.53 (m, 4H) 3.21-3.28 (m, 4H)

5.49 (q, J=6.10 Hz, 1H) 7.05-7.20 (m, 6H) 7.32-7.40 (m, 2H) 7.45 (d, J=7.44 Hz, 1H) 7.60 (s, 1H) 10.55 (s, 1H) 12.63 (s, 1H)

N-[5-(benzyloxy)-1H-indazol-3-yl]-3-(4-methylpiperazin-1-yl)benzamide (Cpd. 50)

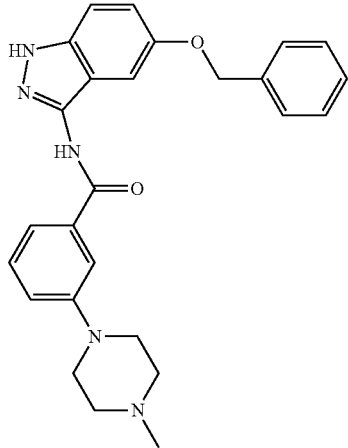 [SMILES: CN1CCN(c2cccc(C(=O)Nc3n[nH]c4ccc(OCc5ccccc5)cc34)c2)CC1]

1H-NMR (400 MHz), δ (ppm, DMSO-d₆): 2.85 (d, J=4.63 Hz, 3H) 3.09-3.26 (m, 4H) 3.58 (br. s., 2H) 3.95-4.00 (m, 2H) 5.07 (s, 2H) 7.12 (dd, J=9.02, 2.44 Hz, 1H) 7.19-7.22 (m, 1H) 7.25-7.50 (m, 8H) 7.58 (d, J=7.44 Hz, 1H) 7.68 (s, 1H) 10.66 (s, 1H) 12.69 (br. s., 1H)

N-{5-[(3,5-difluorobenzyl)oxy]-1H-indazol-3-yl}-3-(4-methylpiperazin-1-yl)benzamide (Cpd. 59)

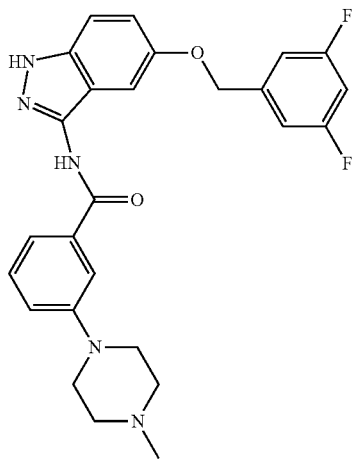 [SMILES: CN1CCN(c2cccc(C(=O)Nc3n[nH]c4ccc(OCc5cc(F)cc(F)c5)cc34)c2)CC1]

1H-NMR (400 MHz), δ (ppm, DMSO-d₆): 2.29-2.38 (m, 3H) 2.57 (d, J=18.17 Hz, 4H) 3.22-3.35 (m, 4H) 5.12 (s, 2H)

7.12-7.27 (m, 6H) 7.37 (t, J=7.93 Hz, 1H) 7.44 (d, J=8.78 Hz, 1H) 7.47-7.51 (m, 1H) 7.63 (s, 1H) 10.62 (s, 1H) 12.69 (s, 1H)

N-{5-[(2-chloro-3,6-difluorobenzyl)oxy]-1H-indazol-3-yl}-3-(4-methylpiperazin-1-yl)benzamide (Cpd. 52)

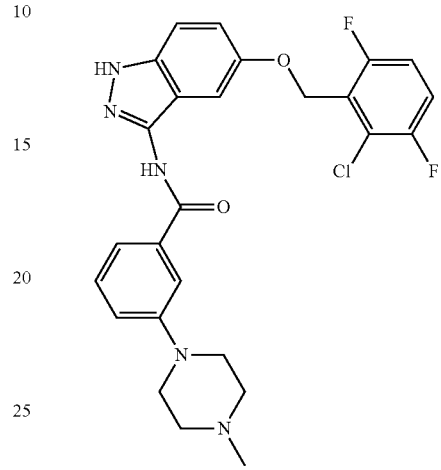

1H-NMR (400 MHz), δ (ppm, DMSO-d₆): 2.83 (m, 3H) 3.18 (m, 4H) 3.58 (m, 2H) 3.99 (m, 2H) 5.15 (d, J=1.22 Hz, 2H) 7.09 (dd, J=9.02, 2.44 Hz, 1H) 7.20-7.33 (m, 3H) 7.37-7.46 (m, 2H) 7.55-7.61 (m, 2H) 7.69 (m, 1H) 10.68 (s, 1H) 12.76 (s, 1H)

N-{5-[(2-chloro-3,6-difluorobenzyl)oxy]-1H-indazol-3-yl}-2-methoxy-4-(4-methylpiperazin-1-yl)benzamide (Cpd. 58)

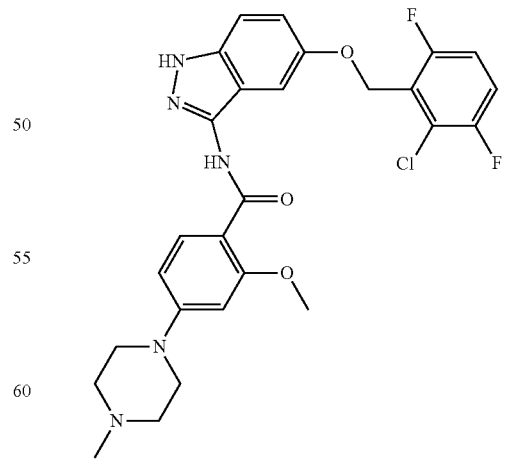

1H-NMR (400 MHz), δ (ppm, DMSO-d₆): 2.85 (d, J=4.63 Hz, 3H) 3.10-3.29 (m, 4H) 3.48-3.56 (m, 2H) 4.04 (s, 3H) 4.11 (d, J=11.83 Hz, 2H) 5.17 (d, J=1.46 Hz, 2H) 6.71-6.77

(m, 2H) 7.08 (dd, J=9.15, 2.32 Hz, 1H) 7.36-7.44 (m, 3H) 7.58 (td, J=8.99, 4.82 Hz, 1H) 7.92 (d, 1H) 10.02 (s, 1H) 12.66 (br. s., 1H)

N-[5-(benzyloxy)-1H-indazol-3-yl]-2-methoxy-4-(4-methylpiperazin-1-yl)benzamide (Cpd. 57)

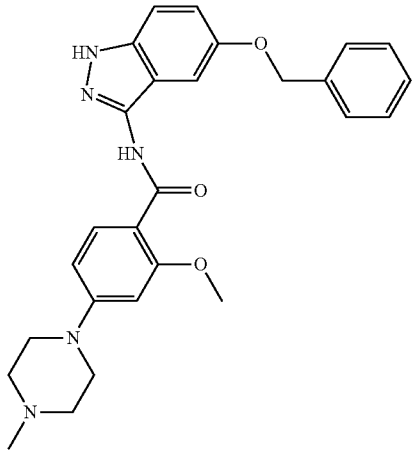 [SMILES: COc1cc(N2CCN(C)CC2)ccc1C(=O)Nc1n[nH]c2ccc(OCc3ccccc3)cc12]

1H-NMR (400 MHz), δ (ppm, DMSO-d$_6$): 2.85 (d, J=4.63 Hz, 3H) 3.09-3.28 (m, 4H) 3.49-3.58 (m, 2H) 4.04 (s, 3H) 4.07-4.15 (m, 2H) 5.08 (s, 2H) 6.73 (s, 1H) 6.74-6.77 (m, 1H) 7.11 (dd, J=9.02, 2.44 Hz, 1H) 7.31-7.35 (m, 1H) 7.35-7.43 (m, 4H) 7.47-7.51 (m, 2H) 7.92 (d, J=8.66 Hz, 1H) 10.00 (s, 1H) 12.61 (br. s., 1H)

N-{5-[(3,5-difluorobenzyl)oxy]-1H-indazol-3-yl}-4-(4-methylpiperazin-1-yl)benzamide (Cpd. 56)

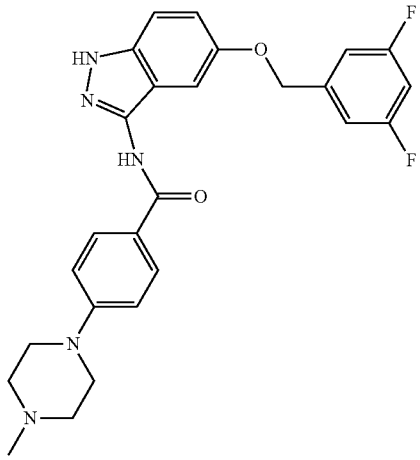 [SMILES: CN1CCN(c2ccc(C(=O)Nc3n[nH]c4ccc(OCc5cc(F)cc(F)c5)cc34)cc2)CC1]

1H-NMR (400 MHz), δ (ppm, DMSO-d$_6$): 2.24 (s, 3H) 2.47 (br. s., 4H) 3.30 (m, 4H) 5.10 (s, 2H) 7.02 (d, J=9.15 Hz, 2H) 7.12-7.22 (m, 5H) 7.42 (dd, J=8.90, 0.73 Hz, 1H) 7.96 (d, J=9.02 Hz, 2H) 10.35 (s, 1H) 12.61 (s, 1H)

N-{5-[(3,5-difluorobenzyl)oxy]-1H-indazol-3-yl}-3-[2-(dimethylamino)ethoxy]benzamide (Cpd. 63)

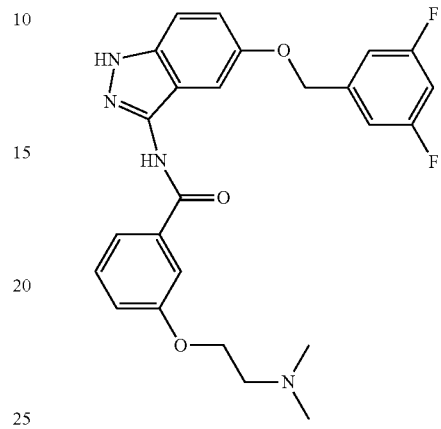

1H-NMR (400 MHz), δ (ppm, DMSO-d$_6$): 2.26 (s, 6H) 2.70 (t, J=5.43 Hz, 2H) 4.16 (t, J=5.73 Hz, 2H) 5.11 (s, 2H) 7.12-7.21 (m, 6H) 7.43 (m, 2H) 7.64 (m, 2H) 10.65 (s, 1H) 12.70 (s, 1H)

N-{5-[(2,5-difluorobenzyl)oxy]-1H-indazol-3-yl}-4-(4-methylpiperazin-1-yl)benzamide (Cpd. 68)

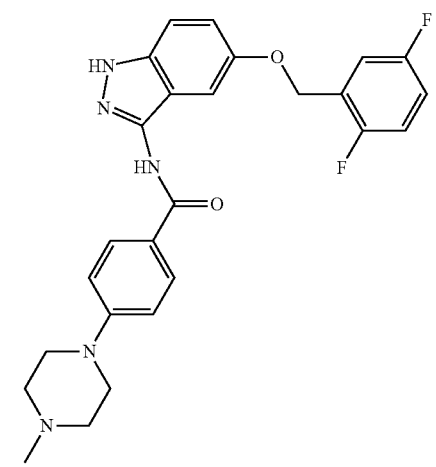 [SMILES: CN1CCN(c2ccc(C(=O)Nc3n[nH]c4ccc(OCc5cc(F)ccc5F)cc34)cc2)CC1]

1H-NMR (400 MHz), δ (ppm, DMSO-d$_6$): 2.23 (s, 3H) 2.45 (t, J=4.80 Hz, 4H) 3.30 (t, J'4.70 Hz, 4H) 5.09 (s, 2H) 7.01 (d, J=8.91 Hz, 2H) 7.10 (dd, J=9.03, 2.32 Hz, 1H) 7.20 (d, J=2.32 Hz, 1H) 7.24 (ddd, J=9.03, 7.57. 3.70 Hz, 1H) 7.30

(td, J=9.09, 4.58 Hz, 1H) 7.43 (ddd, J=8.79, 5.74, 3.17 Hz, 1H) 7.41 (d, J=9.03 Hz, 1H) 7.96 (d, J=8.91 Hz, 2H) 10.35 (s, 1H) 12.61 (s, 1H)

N-{5-[(3,5-difluorobenzyl)oxy]-1H-indazol-3-yl}-3-[(1-methylpiperidin-4-yl)oxy]benzamide (Cpd. 47)

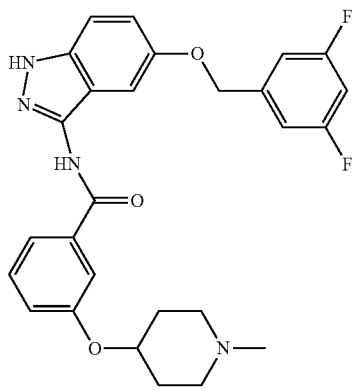 [SMILES: CN1CCC(Oc2cccc(C(=O)Nc3n[nH]c4ccc(OCc5cc(F)cc(F)c5)cc34)c2)CC1]

1H-NMR (400 MHz), δ (ppm, DMSO-d$_6$): 1.68 (br. s., 2H) 1.98 (br. s., 2H) 2.10-2.30 (m, 2H) 2.20 (s, 3H) 2.57-2.73 (m, 2H) 4.42-4.56 (m, 1H) 5.11 (s, 2H) 7.13-7.21 (m, 6H) 7.41-7.45 (m, 2H) 7.62 (m, 2H) 10.63 (s, 1H) 12.70 (s, 1H)

N-{5-[(3,5-difluorobenzyl)oxy]-1H-indazol-3-yl}-4-[(1-methylpiperidin-4-yl)oxy]benzamide (Cpd. 49)

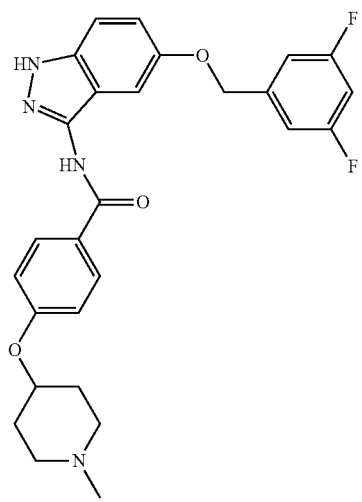 [SMILES: CN1CCC(Oc2ccc(C(=O)Nc3n[nH]c4ccc(OCc5cc(F)cc(F)c5)cc34)cc2)CC1]

1H-NMR (400 MHz), δ (ppm, DMSO-d$_6$): 1.70 (m, 2H) 1.98 (m, 2H) 2.23 (d, J=0.49 Hz, 3H) 2.28 (m, 2H) 2.67 (m, 2H) 4.53 (tt, J=7.70, 3.50 Hz, 1H) 5.10 (s, 2H) 7.08 (d, J=8.90

Hz, 2H) 7.11-7.23 (m, 5H) 7.42 (dd, J=8.60, 1.04 Hz, 1H) 8.03 (d, J=8.78 Hz, 2H) 10.49 (s, 1H) 12.65 (s, 1H)

N-{5-[(3,5-difluorobenzyl)oxy]-1H-indazol-3-yl}-3-(4-methylpiperazin-1-yl)benzamide (Cpd. 69)

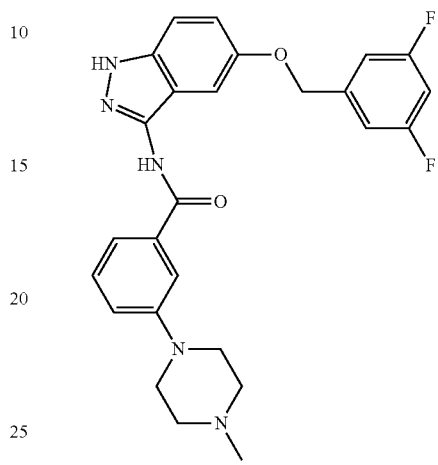

1H-NMR (400 MHz), δ (ppm, DMSO-d$_6$): 2.24 (s, 3H) 2.48 (t, J=4.80 Hz, 4H) 3.24 (t, J=4.80 Hz, 4H) 5.10 (s, 2H) 7.11 (dd, J=8.97, 2.38 Hz, 1H) 7.16 (dd, J=8.36, 2.01 Hz, 1H) 7.22 (d, J=2.32 Hz, 1H) 7.23-7.28 (m, 1H) 7.30 (td, J=9.03, 4.64 Hz, 1H) 7.36 (t, J=7.87 Hz, 1H) 7.42 (dd, J=9.03, 0.37 Hz, 1H) 7.44 (ddd, J=8.90, 5.50, 3.42 Hz, 1H) 7.47 (d, J=7.20 Hz, 1H) 7.61 (br. s., 1H) 10.61 (s, 1H) 12.68 (s, 1H)

N-{5-[(3,5-difluorobenzyl)oxy]-1H-indazol-3-yl}-1-(1-methylpiperidin-4-yl)-1H-pyrazole-4-carboxamide (Cpd. 48)

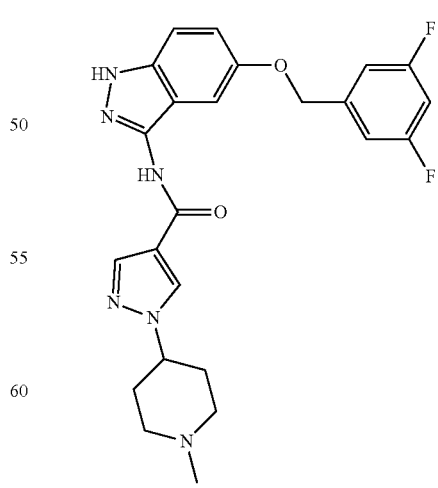

1H-NMR (400 MHz), δ (ppm, DMSO-d$_6$): 2.05 (m, 6H) 2.24 (s, 3H) 2.89 (d, J=11.34 Hz, 2H) 4.20 (tt, J=11.10, 4.50

Hz, 1H) 5.09 (s, 2H) 7.13 (dd, J=9.02, 2.44 Hz, 1H) 7.16-7.22 (m, 4H) 7.41 (d, J=9.02 Hz, 1H) 8.10 (s, 1H) 8.45 (s, 1H) 10.33 (s, 1H) 12.63 (s, 1H)

tert-butyl 4-(4-{[5-(benzyloxy)-1H-indazol-3-yl]carbamoyl}-1H-pyrazol-1-yl)piperidine-1-carboxylate

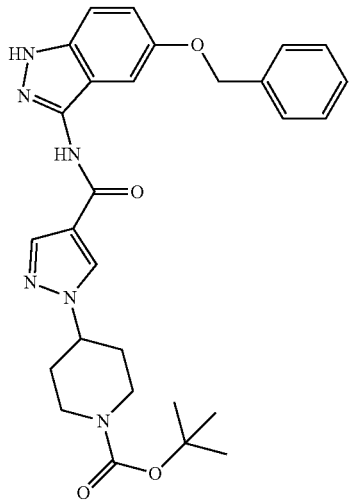 [SMILES: CC(C)(C)OC(=O)N1CCC(n2cc(C(=O)Nc3n[nH]c4ccc(OCc5ccccc5)cc34)cn2)CC1]

ESI(+) MS: m/z 517 (MH$^+$).

tert-butyl 4-(3-{[5-(benzyloxy)-1H-indazol-3-yl]carbamoyl}phenyl)piperazine-1-carboxylate

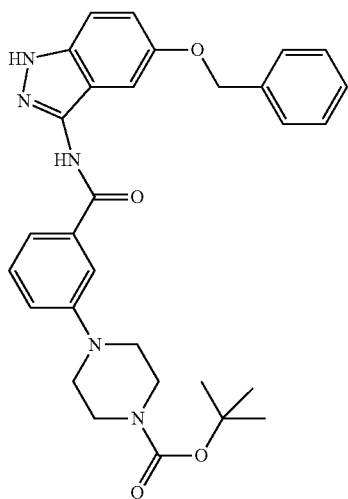 [SMILES: CC(C)(C)OC(=O)N1CCN(c2cccc(C(=O)Nc3n[nH]c4ccc(OCc5ccccc5)cc34)c2)CC1]

ESI(+) MS: m/z 528 (MH$^+$).

N-{5-[(3,5-difluorobenzyl)oxy]-1H-indazol-3-yl}-4-{[3-(dimethylamino)propyl](methyl)amino}benzamide (Cpd. 60)

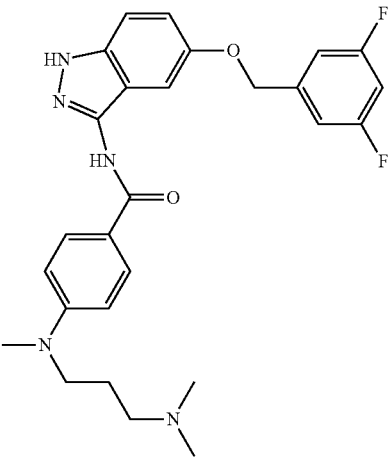 [SMILES: CN(C)CCCN(C)c1ccc(C(=O)Nc2n[nH]c3ccc(OCc4cc(F)cc(F)c4)cc23)cc1]

1H-NMR (400 MHz), δ (ppm, DMSO-d$_6$): 1.67 (quin, J=6.95 Hz, 2H) 2.16 (s, 6H) 2.25 (t, J=6.89 Hz, 2H) 2.98 (s, 3H) 3.44 (t, J=7.19 Hz, 2H) 5.09 (s, 2H) 6.76 (d, J=9.15 Hz, 2H) 7.10-7.22 (m, 5H) 7.41 (dd, 1H) 7.93 (d, J=9.15 Hz, 2H) 10.23 (s, 1H) 12.59 (s, 1H)

N-[5-(benzyloxy)-1H-indazol-3-yl]-2-methyl-4-(4-methylpiperazin-1-yl)benzamide (Cpd. 54)

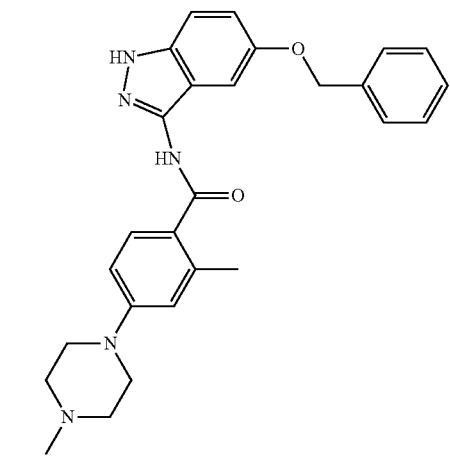 [SMILES: Cc1cc(N2CCN(C)CC2)ccc1C(=O)Nc1n[nH]c2ccc(OCc3ccccc3)cc12]

1H-NMR (400 MHz), δ (ppm, DMSO-d$_6$): 2.47 (s, 3H) 2.84 (s, 3H) 3.07-3.20 (m, 4H) 2.46-3.55 (m, 2H) 3.93-4.01 (m, 2H) 5.08 (s, 2H) 6.88-6.95 (m, 2H) 7.11 (dd, J=8.96, 2.38

Hz, 1H) 7.21 (d, J=2.07 Hz, 1H) 7.30-7.36 (m, 1H) 7.37-7.43 (m, 3H) 7.45-7.51 (m, 2H) 7.56 (d, J=8.17 Hz, 1H) 10.29 (s, 1H) 12.56 (s, 1H)

N-{5-[(2-chloro-3,6-difluorobenzyl)oxy]-1H-indazol-3-yl}-2-methyl-4-(4-methylpiperazin-1-yl)benzamide (Cpd. 55)

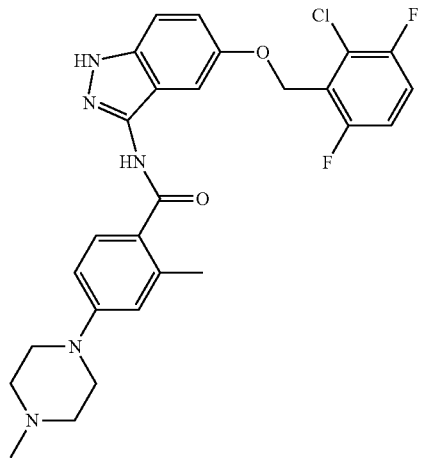 [SMILES: Cc1cc(N2CCN(C)CC2)ccc1C(=O)Nc1n[nH]c2ccc(OCc3c(F)ccc(F)c3Cl)cc12]

1H-NMR (400 MHz), δ (ppm, DMSO-d$_6$): 2.48 (s, 3H) 2.84 (s, 3H) 3.07-3.21 (m, 4H) 3.44-3.55 (m, 2H) 3.97 (d, J=9.76 Hz, 2H) 5.17 (d, J=1.34 Hz, 2H) 6.88-6.96 (m, 2H) 7.08 (dd, J=8.96, 2.38 Hz, 1H) 7.28 (d, J=2.19 Hz, 1H) 7.36-7.42 (m, 1H) 7.40-7.44 (m, 1H) 7.58 (td, J=8.99, 4.82 Hz, 2H) 10.32 (s, 1H_) 12.61 (s, 1H)

N-[5-(3,5-difluorophenoxy)-1H-indazol-3-yl]-4-(4-methylpiperazin-1-yl)benzamide (Cpd. 75)

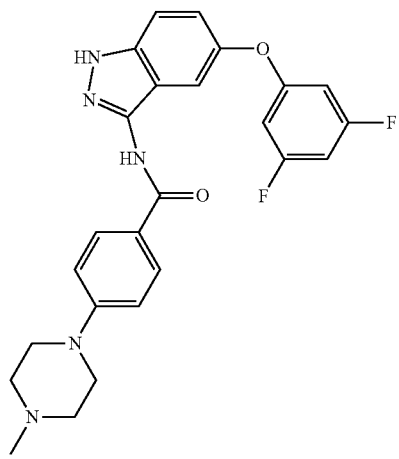 [SMILES: CN1CCN(c2ccc(C(=O)Nc3n[nH]c4ccc(Oc5cc(F)cc(F)c5)cc34)cc2)CC1]

1H-NMR (400 MHz), δ (ppm, DMSO-d$_6$): 2.26 (s, 3H) 2.49 (s, 4H) 3.31 (s, 4H) 6.64 (dd, J=8.84, 2.26 Hz, 2) 6.93 (tt, J=9.31, 2.27 Hz, 1H) 7.01 (d, J=9.02 Hz, 2H) 7.20 (dd, J=8.90, 2.32 Hz, 1H) 7.48 (d, J=2.32 Hz, 1H) 7.58 (dd, J=8.90, 0.49 Hz, 1H) 7.95 (d, J=9.02 Hz, 2H) 10.53 (s, 1H) 12.88 (s, 1H)

N-[5-(3,5-difluorophenoxy)-1H-indazol-3-yl]-4-(4-methylpiperazin-1-yl)-2-(tetrahydro-2-(tetrahydro-2H-pyran-4-ylamino)benzamide (Cpd. 76)

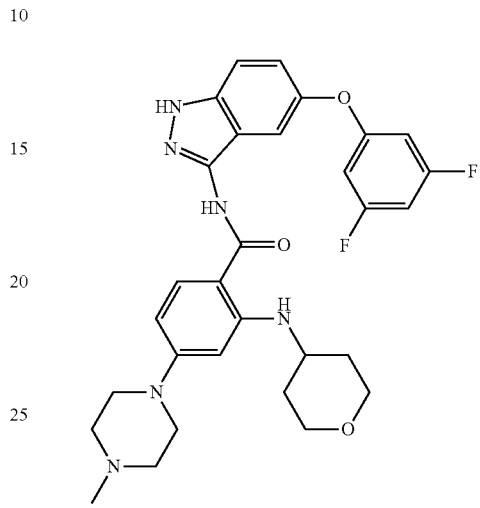

1H-NMR (400 MHz), δ (ppm, DMSO-d$_6$): 1.23-1.40 (m, 2H) 1.91 (dd, J=12.50, 2.87 Hz, 2H) 2.27 (br. s., 3H) 2.42-2.56 (m, 4H) 3.24-3.34 (m, 4H) 3.43-3.52 (m, 2H) 3.66 (d, J=11.95 Hz, 1H) 3.75-3.83 (m, 2H) 6.13 (d, J=2.19 Hz, 1H) 6.23 (dd, J=8.96, 2.26 Hz, 1H) 6.62-6.73 (m, 2H) 6.89-6.97 (m, 1H) 7.19 (dd, J=9.02, 2.32 Hz, 1H) 7.34 (d, J=2.19 Hz, 1H) 7.57 (dd, J=8.90, 0.61 Hz, 1H) 7.78 (d, J=9.15 Hz, 1H) 8.21 (d, J=7.68 Hz, 1H) 10.20 (s, 1H) 12.83 (s, 1H)

N-[5-(3,5-difluorophenoxy)-1H-indazol-3-yl]-3-[(1-methylpiperidin-4-yl)oxy]benzamide (Cpd. 77)

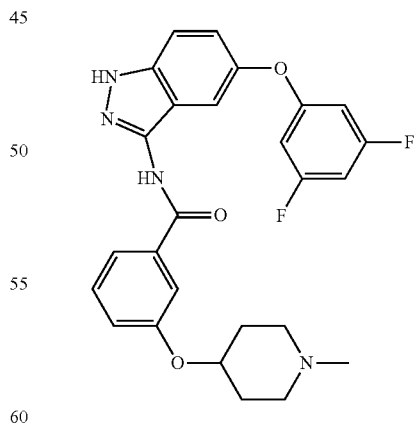

1H-NMR (400 MHz), δ (ppm, DMSO-d$_6$): 1.58-1.74 (m, 2H) 1.88-2.01 (m, 2H) 2.10-2.28 (m, 2H) 2.18 (s, 3H) 2.57-2.66 (m, 2H) 4.48 (tt, J=8.30, 3.90 Hz, 1H) 6.58-6.68 (m, 2H) 6.92 (tt, J=9.33, 2.32 Hz, 1H) 7.16 (ddd, J=8.20, 2.41, 0.85 Hz, 1H) 7.20 (dd, J=9.02, 2.32 Hz, 1H) 7.41 (t, J=8.17 Hz, 1H) 7.49 (d, J=2.32 Hz, 1H) 7.59 (dd, J=8.90, 0.49 Hz, 1H) 7.60 (m, 2H) 10.80 (s, 1H) 12.95 (s, 1H)

J=8.90, 2.32 Hz, 1H) 7.34-7.42 (m, 2H) 7.56 (dd, J=8.90, 0.49 Hz, 1H) 7.94 (d, J=9.02 Hz, 2H) 10.50 (s, 1H) 12.84 (s, 1H)

4-(4-methylpiperazin-1-yl)-N-(5-phenoxy-1H-indazol-3-yl)benzamide (Cpd. 70)

N-{5-[4-(benzyloxy)phenoxy]-1H-indazol-3-yl}-4-(4-methylpiperazin-1-yl)benzamide (Cpd. 72)

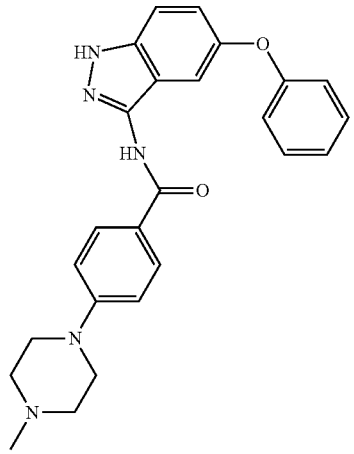 [SMILES: CN1CCN(c2ccc(C(=O)Nc3n[nH]c4ccc(Oc5ccccc5)cc34)cc2)CC1]

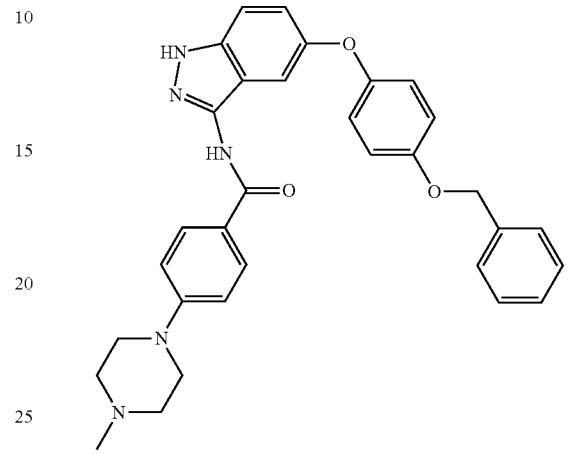

1H-NMR (400 MHz), δ (ppm, DMSO-d$_6$): 2.26 (s, 3H) 2.49 (m, 4H) 3.31 (m, 4H) 6.93-7.02 (m, 4H) 7.07 (tt, J=7.44, 1.10 Hz, 1H) 7.15 (dd, J=9.02, 2.32 Hz, 1H) 7.32-7.38 (m, 3H) 7.53 (td, J=8.90, 0.61 Hz, 1H) 7.93 (d, J=8.90 Hz, 2H) 10.46 (s, 1H) 12.80 (s, 1H)

1H-NMR (400 MHz), δ (ppm, DMSO-d$_6$): 2.26 (s, 3H) 2.50 (m, 4H) 3.32 (m, 4H) 5.07 (s, 2H) 6.91-6.96 (m, 2H) 6.98-7.02 (m, 4H) 7.12 (dd, J=8.90, 2.32 Hz, 1H) 7.20 (d, J=2.19 Hz, 1H) 7.30-7.52 (m, 6H) 7.93 (d, J=9.02 Hz, 2H) 10.41 (s, 1H) 12.75 (s, 1H)

N-[5-(3-fluorophenoxy)-1H-indazol-3-yl]-4-(4-methylpiperazin-1-yl)benzamide (Cpd. 71)

4-(4-methylpiperazin-1-yl)-N-[5-(4-phenoxyphenoxy)-1H-indazol-3-yl]benzamide (Cpd. 73)

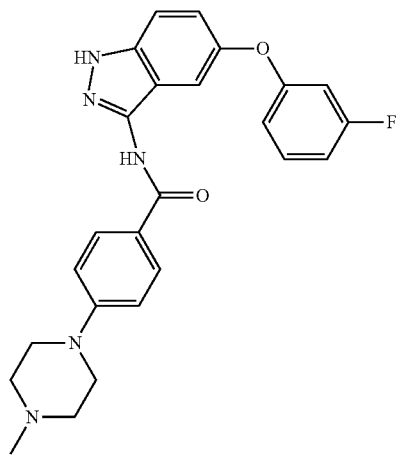 [SMILES: CN1CCN(c2ccc(C(=O)Nc3n[nH]c4ccc(Oc5cccc(F)c5)cc34)cc2)CC1]

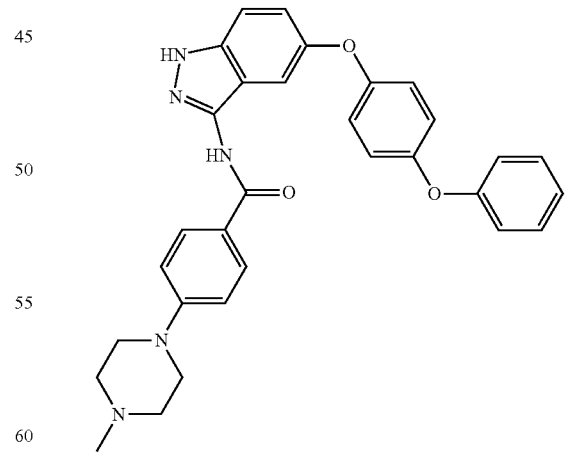

1H-NMR (400 MHz), δ (ppm, DMSO-d$_6$): 2.25 (s, 3H) 2.52 (m, 4H) 3.34 (m, 4H) 6.65-6.80 (m, 2H) 6.90 (tdd, J=8.66, 2.44, 0.85 Hz, 1H) 7.01 (d, J=9.02 Hz, 2H) 7.18 (dd, 1H-NMR (400 MHz), δ (ppm, DMSO-d$_6$): 2.27 (s, 3H) 2.52 (m, 4H) 3.34 (m, 4H) 6.95-7.05 (m, 8H) 7.10 (tt, J=7.32, 1.10 Hz, 1H) 7.17 (dd, J=8.90, 2.32 Hz, 1H) 7.30-7.38 (m, 3H) 7.52 (t, J=9.02 Hz, 1H) 7.95 (d, J=9.02 Hz, 2H) 10.46 (s, 1H) 12.79 (s, 1H)

N-{5-[3-(benzyloxy)phenoxy]-1H-indazol-3-yl}-4-(4-methylpiperazin-1-yl)benzamide (Cpd. 74)

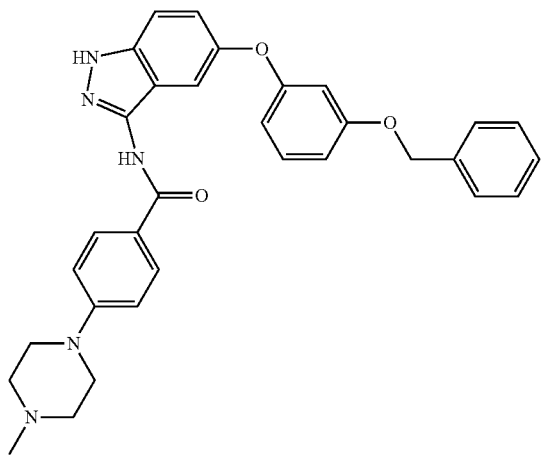 [SMILES: CN1CCN(c2ccc(C(=O)Nc3n[nH]c4ccc(Oc5cccc(OCc6ccccc6)c5)cc34)cc2)CC1]

1H-NMR (400 MHz), δ (ppm, DMSO-d$_6$): 2.26 (s, 3H) 2.49 (m, 4H) 3.34 (m, 4H) 5.07 (s, 2H) 6.50 (ddd, J=8.15, 2.32, 0.61 Hz, 1H) 6.61 (t, J=2.32 Hz, 1H) 6.72 (ddd, J=8.29, 2.32, 0.61 Hz, 1H) 7.01 (d, J=9.02 Hz, 2H) 7.14 (dd, J=8.90, 2.20 Hz, 1H) 7.24 (t, J=8.17 Hz, 1H) 7.30-7.43 (m, 6H) 7.53 (d, J=8.54, 1H) 7.95 (d, J=9.02 Hz, 2H) 10.47 (s, 1H) 12.80 (s, 1H)

N-[5-(3,5-difluorophenoxy)-1H-indazol-3-yl]-4-[(1-methylpiperidin-4-yl)oxy]benzamide (Cpd. 80)

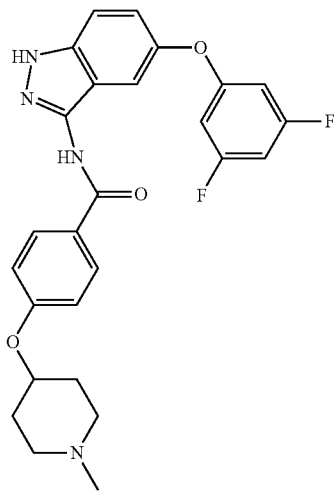 [SMILES: CN1CCC(Oc2ccc(C(=O)Nc3n[nH]c4ccc(Oc5cc(F)cc(F)c5)cc34)cc2)CC1]

1H-NMR (400 MHz), δ (ppm, DMSO-d$_6$): 1.67 (br. s., 2H) 1.96 (br. s., 2H) 2.21 (br. s., 3H) 2.24 (br. s., 2H) 2.65 (br. s., 2H) 4.51 (tt, J=7.90, 3.50 Hz, 1H) 6.58-6.67 (m, 2H) 6.91 (tt, J=9.31, 2.33 Hz, 1H) 7.05 (d, J=9.02 Hz, 2H) 7.19 (dd, J=8.90, 2.32 Hz, 1H) 7.47 (d, J=2.32 Hz, 1H) 7.57 (dd, J=8.96, 0.55 Hz, 1H) 8.01 (d, J=8.90 Hz, 2H) 10.65 (s, 1H) 12.90 (s, 1H)

N-[5-(3,5-difluorophenoxy)-1H-indazol-3-yl]-3-(4-methylpiperazin-1-yl)benzamide (Cpd. 81)

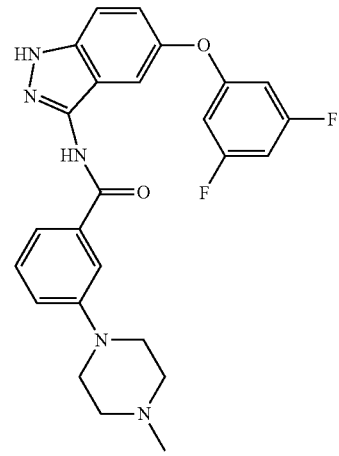 [SMILES: CN1CCN(c2cccc(C(=O)Nc3n[nH]c4ccc(Oc5cc(F)cc(F)c5)cc34)c2)CC1]

1H-NMR (400 MHz), δ (ppm, DMSO-d$_6$): 2.84 (d, J=4.63 Hz, 3H) 3.13 (m, 4H) 3.52 (d, J=12.07 Hz, 2H) 3.96 (d, J=12.07 Hz, 2H) 6.58-6.68 (m, 2H) 6.92 (tt, J=9.30, 2.35 Hz, 1H) 7.21 (dd, J=8.90, 2.32 Hz, 1H) 7.24 (dd, J=8.43, 2.32 Hz, 1H) 7.40 (t, J=7.93 Hz, 1H) 7.50 (dd, J=2.32, 0.49 Hz, 1H) 7.54 (d, J=7.68 Hz, 1H) 7.59 (dd, J=8.90, 0.61 Hz, 1H) 7.64 (t, J=2.01 Hz, 1H) 10.82 (s, 1H) 12.97 (br. s., 1H)

3-(4-methylpiperazin-1-yl)-N-(5-phenoxy-1H-indazol-3-yl)benzamide (Cpd. 83)

1H-NMR (400 MHz), δ (ppm, DMSO-d$_6$): 2.83 (d, J=4.63 Hz, 3H) 3.05-3.24 (m, 4H) 3.50 (t, J=10.85 Hz, 2H) 3.95 (d, J=11.22 Hz, 2H) 6.94 (dd, J=8.66, 0.98 Hz, 2H) 7.06 (tt, J=7.36, 0.99 Hz, 1H) 7.15 (dd, J=8.96, 2.26 Hz, 1H) 7.23 (dd, J=8.11, 2.01 Hz, 1H) 7.34 (m, 3H) 7.39 (t, J=7.93 Hz, 1H) 7.51 (d, 1H) 7.61-7.66 (m, 1H) 10.76 (s, 1H) 12.89 (br. s., 1H)

2-methoxy-4-(4-methylpiperazin-1-yl)-N-(5-phenoxy-1H-indazol-3-yl)benzamide hydrochloride (Cpd. 85)

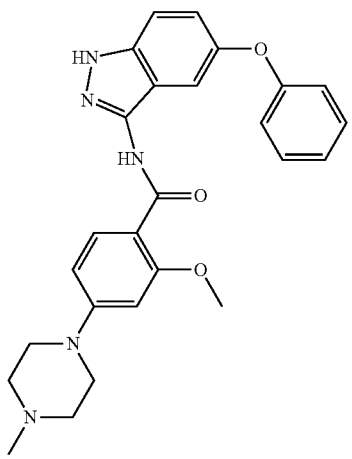 [SMILES: COc1cc(N2CCN(C)CC2)ccc1C(=O)Nc1n[nH]c2ccc(Oc3ccccc3)cc12]

1H-NMR (400 MHz), δ (ppm, DMSO-d$_6$): 2.85 (d, J=4.63 Hz, 3H) 3.02-3.26 (m, 4H) 3.47-3.55 (m, 2H) 4.01 (s, 3H) 4.04-4.13 (m, 2H) 6.67-6.74 (m, 2H) 6.96 (dd, J=8.72, 1.04 Hz, 2H) 7.07 (dt, J=14.75, 1.04 Hz, 1H) 7.15 (dd, J=9.02, 2.19 Hz, 1H) 7.36 (dd, J=8.66, 7.32 Hz, 2H) 7.51-7.55 (m, 2H) 7.85 (d, J=8.66 Hz, 1H) 10.09 (s, 1H) 10.36 (br. s., 1H) 12.82 (br. s., 1H)

N-[5-(3,5-difluorophenoxy)-1H-indazol-3-yl]-2-methoxy-4-(4-methylpiperazin-1-yl)benzamide hydrochloride (Cpd. 84)

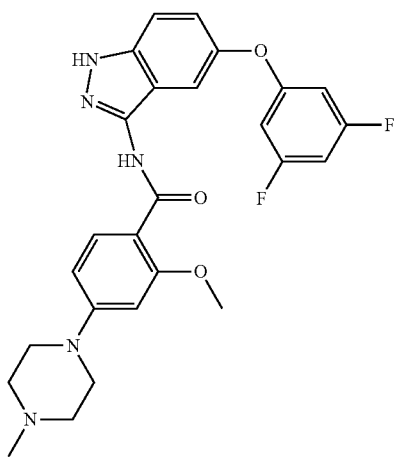 [SMILES: COc1cc(N2CCN(C)CC2)ccc1C(=O)Nc1n[nH]c2ccc(Oc3cc(F)cc(F)c3)cc12]

1H-NMR (400 MHz), δ (ppm, DMSO-d$_6$): 2.84 (d, J=4.51 Hz, 3H) 3.06-3.24 (m, 4H) 3.51 (d, J=10.97 Hz, 2H) 4.02 (s, 3H) 4.10 (d, J=11.58 Hz, 2H) 6.59-6.68 (m, 2H) 6.70 (s, 1H) 6.72 (m, 1H) 6.92 (tt, J=9.33, 2.32 Hz. 1H) 7.19 (dd, J=8.96, 2.38 Hz, 1H) 7.56 (d, J=9.02 Hz, 1H) 7.66 (d, J=1.95 Hz, 1H) 7.87 (d, J=8.54 Hz, 1H) 10.14 (s, 1H) 10.32 (br. s., 1H) 12.77-13.08 (m, 1H)

N-[5-(3,5-difluorophenoxy)-1H-indazol-3-yl]-3-[2-(dimethylamino)ethoxy]benzamide (Cpd. 86)

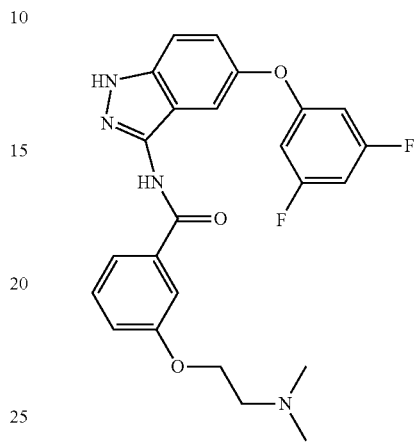

1H-NMR (400 MHz), δ (ppm, DMSO-d$_6$): 2.24 (s, 6H) 2.67 (t, J=5.61 Hz, 2H) 4.14 (t, J=5.79 Hz, 2H) 6.57-6.69 (m, 2H) 6.92 (tt, J=9.34, 2.30 Hz, 1H) 7.15 (ddd, J=8.26, 2.41, 0.91 Hz, 1H) 7.20 (dd, J=8.90, 2.32 Hz, 1H) 7.42 (t, J=8.17 Hz, 1H) 7.50 (d, J=2.19 Hz, 1H) 7.59 (dd, J=8.90, 0.49 Hz, 1H) 7.62 (m, 2H) 10.81 (s, 1H) 12.95 (s, 1H)

N-[5-(3,5-difluorophenoxy)-1H-indazol-3-yl]-4-[2-(dimethylamino)ethoxy]benzamide (Cpd. 93)

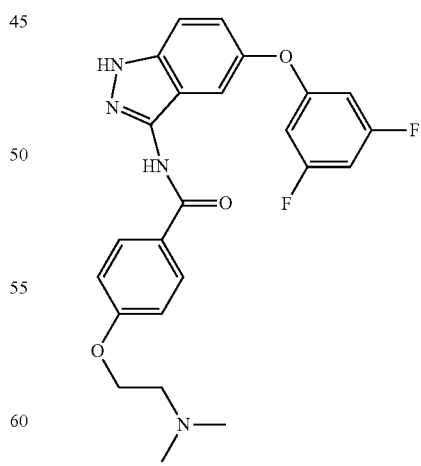

1H-NMR (400 MHz), δ (ppm, DMSO-d$_6$): 2.24 (s, 6H) 2.67 (t, J=5.55 Hz, 2H) 4.14 (t, J=5.80 Hz, 2H) 6.63 (dd, J=8.79, 2.20 Hz, 2H) 6.91 (tt, J=9.28, 2.26 Hz, 1H) 7.05 (d, J=8.91 Hz, 2H) 7.19 (dd, J=8.91, 2.32 Hz, 1H) 7.48 (d, J=2.20 Hz, 1H) 7.58 (d, J=8.91 Hz, 1H) 8.02 (d, J=8.91 Hz, 2H) 10.66 (s, 1H) 12.91 (s, 1H)

N-{5-(3,5-difluorophenoxy)-1H-indazol-3-yl}-1-(1-methylpiperidin-4-yl)-1H-pyrazole-4-carboxamide (Cpd. 79)

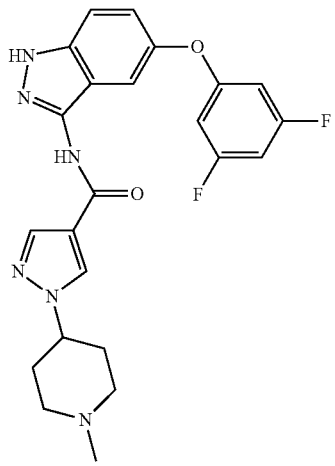 [SMILES: CN1CCC(n2cc(C(=O)Nc3n[nH]c4ccc(Oc5cc(F)cc(F)c5)cc34)cn2)CC1]

1H-NMR (400 MHz), δ (ppm, DMSO-d$_6$): 1.89-2.08 (m, 4H) 2.15 (br. s., 2H) 2.26 (br. s., 3H) 2.91 (d, J=7.80 Hz, 2H) 4.19 (tt, J=10.50, 3.80 Hz, 1H) 6.58-6.67 (m, 2H) 6.92 (tt, J=9.31, 2.27 Hz, 1H) 7.19 (dd, J=8.90, 2.32 Hz, 1H) 7.51 (d, J=2.32 Hz, 1H) 7.56 (dd, J=8.96, 0.55 Hz, 1H) 8.09 (s, 1H) 8.45 (s, 1H) 10.51 (s, 1H) 12.88 (s, 1H)

2-methyl-4-(4-methylpiperazin-1-yl)-N-(5-phenoxy-1H-indazol-3-yl)benzamide (Cpd. 78)

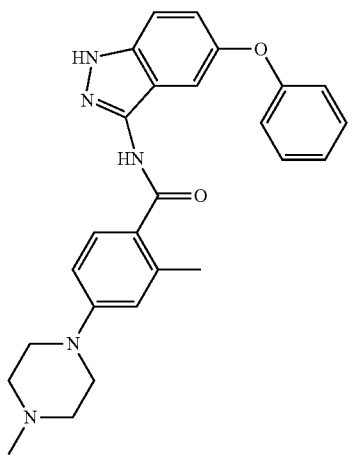 [SMILES: Cc1cc(N2CCN(C)CC2)ccc1C(=O)Nc1n[nH]c2ccc(Oc3ccccc3)cc12]

1H-NMR (400 MHz), δ (ppm, DMSO-d$_6$): 2.39 (s, 3H) 2.83 (s, 3H) 3.02-3.21 (m, 4H) 3.48 (m, 2H) 3.87-4.04 (m, 2H) 6.87 (dd, J=8.78, 2.20 Hz, 1H) 6.90 (d, J=2.20 Hz, 1H) 6.96 (dd, J=8.66, 0.98 Hz, 2H) 7.07 (t, J=7.38 Hz, 1H) 7.14 (dd, J=9.02, 2.32 Hz, 1H) 7.35 (m, 3H) 7.52 (d, J=8.54 Hz, 1H) 7.52 (dd, J=8.90, 0.61 Hz, 1H) 10.39 (s, 1H) 12.77 (br. s., 1H)

N-[5-(3,5-difluorophenoxy)-1H-indazol-3-yl]-2-methyl-4-(4-methylpiperazin-1-yl)benzamide (Cpd. 82)

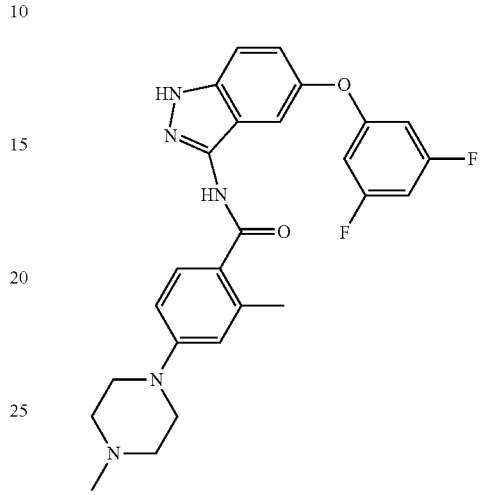

1H-NMR (400 MHz), δ (ppm, DMSO-d$_6$): 2.42 (s, 3H) 2.82 (s, 3H) 3.03-3.20 (m, 4H) 3.43-3.53 (m, 2H) 3.88-4.03 (m, 2H) 6.61-6.70 (m, 2H) 6.90 (m, 2H) 6.93 (tt, J=9.27, 2.32 Hz, 1H) 7.19 (dd, J=8.96, 2.26 Hz, 1H) 7.49 (d, J=2.30 Hz, 1H) 7.54 (d, J=9.00 Hz, 1H) 7.57 (dd, J=9.02, 0.49 Hz, 1H) 10.47 (s, 1H) 12.84 (br. s., 1H)

Example 2

Step d

N-(5-Benzyloxy-1H-indazol-3-yl)-4-(4-methyl-piperazin-1-yl)-2-[(tetrahydro-pyran-4-yl)-(2,2,2-trifluoro-acetyl)-amino]-benzamide 4-(4-Methyl-piperazin-1-yl)-2-[(tetrahydro-pyran-4-yl)-(2,2,2-trifluoro-acetyl)-amino]-benzoyl chloride (10.04 mmol), in dry pyridine (100 mL), under a nitrogen atmosphere, cooled to 4° C., was treated with 5-benzyloxy-1H-indazol-3-ylamine (2 g, 8.37 mmol) in pyridine (35 mL) and stirred for 3 hours. The mixture was concentrated in vacuo. The residue was added to iced water (350 mL) and extracted with EtOAc (400 mL and 2×200 mL). The combined organic layers were dried over anhydrous sodium sulfate. After removal of the volatiles a brown solid was obtained that was taken in Et20 (200 mL), stirred 2 hours at room temperature, filtered and dried at 50° C. under vacuum to afford 4 g of title compound.

1H-NMR (400 MHz), δ (ppm, DMSO-d$_6$): 1.24-1.40 (m, 1H) 1.57 (qd, J=12.38, 3.96 Hz, 1H) 1.72 (br. s., 1H) 1.95 (d, J=12.56 Hz, 1H) 2.29 (br. s., 3H) 2.42-2.61 (m, 4H) 3.25-3.45 (m, 6H) 3.75-3.92 (m, 2H) 4.40-4.54 (m, 1H) 5.02 (s, 2H) 6.91 (d, J=2.32 Hz, 1H) 7.07-7.13 (m, 3H) 7.30-7.37 (m, 1H)

7.45-7.49 (m, 2H) 7.86 (d, J=8.90 Hz, 1H) 10.54 (s, 1H) 12.62 (s, 1H)

Conversion 4, Step 4A

Preparation of 5-benzyloxy-3-{4-(4-methyl-piperazin-1-yl)-2-[(tetrahydro-pyran-4-yl)-(2,2,2-trifluoro-acetyl)-amino]-benzoylamino}-indazole-1-carboxylic acid tert-butyl ester N-(5-Benzyloxy-1H-indazol-3-yl)-4-(4-methyl-piperazin-1-yl)-2-[(tetrahydro-pyran-4-yl)-(2,2,2-trifluoro-acetyl)-amino]-benzamide (3.8 g, 5.97 mmol) in dry DMF (40 mL) was treated with DIPEA (4.1 mL, 23.88 mmol) and (Boc)$_2$O (1.92 g, 8.79 mmol). After three days at room temperature, more (Boc)$_2$O was added (360 mg). The following day the reaction mixture was poured into cold water (600 mL) and extracted with EtOAc (3×300 mL). The organic phase was dried over sodium sulfate and evaporated to leave an oil which was purified by flash chromatography over silica gel (eluent: DCM:EtOH:35% NH$_4$OH 95:5:0.5) to afford 2.64 g of title compound in 60% yield.

1H-NMR (400 MHz), δ (ppm, DMSO-d$_6$): 1.22-1.33 (m, 1H) 1.51-1.60 (m, 1H) 1.61-1.63 (m, 1H) 1.64 (s, 9H) 1.91-1.97 (m, 1H) 2.25 (s, 3H) 2.44-2.50 (m, 4H) 3.28-3.42 (m, 6H) 3.74-3.91 (m, 1H) 4.42-4.53 (m, 1H) 5.05 (s, 2H) 6.92 (d, J=2.44 Hz, 1H) 7.10 (dd, J=9.02, 2.56 Hz, 1H) 7.30-7.34 (m, 1H) 7.35-7.39 (m, 1H) 7.38-7.43 (m, 2H) 7.44-7.48 (m, 2H) 7.90 (d, J=8.90 Hz, 1H) 8.00 (d, J=9.15 Hz, 1H) 11.13 (s, 1H)

Conversion 4, Step 4B

Preparation of 5-hydroxy-3-{4-(4-methyl-piperazin-1-yl)-2-[(tetrahydro-pyran-4-yl)-(2,2,2-trifluoro-acetyl)-amino]-benzoylamino}indazole-1-carboxylic acid tert-butyl ester 5-Benzyloxy-3-{4-(4-methyl-piperazin-1-yl)-2-[(tetrahydro-pyran-4-yl)-(2,2,2-trifluoro-acetyl)-amino]-benzoylamino}-indazole-1-carboxylic acid tert-butyl ester (2.3 g, 3.13 mmol) in dioxane (46 mL) was treated with cyclohexene (18 mL) and 10% Pd/C (1.6 g). The mixture was stirred at reflux temperature. After 1.5 hs it was filtered over a celite funnel and washed with dioxane. Evaporation of the solvent left a solid that was washed with Et$_2$O. After drying at 45° C. under vacuum, 1.92 g of title compound in 95% yield were obtained.

1H-NMR (400 MHz), δ (ppm, DMSO-d$_6$): 1.23-1.33 (m, 1H) 1.46-1.59 (m, 1H) 1.60-1.66 (m, 1H) 1.63 (s, 9H) 1.87-1.95 (m, 1H) 2.29 (br. s., 3H) 2.44-2.60 (m, 4H) 3.28-3.44 (m, 6H) 3.81 (dd, J=11.58, 4.15 Hz, 1H) 3.88 (dd, J=10.67, 4.33 Hz, 1H) 4.38-4.53 (m, 1H) 6.90 (d, J=2.44 Hz, 1H) 6.97 (d, J=2.07 Hz, 1H) 7.07-7.11 (m, 1H) 7.09-7.12 (m, 1H) 7.84 (d, J=8.78 Hz, 1H) 7.90 (d, J=9.02 Hz, 1H) 9.64 (s, 1H) 11.01 (s, 1H)

Conversion 4, Step 4C

Preparation of 5-(2-chloro-5-fluoro-benzyloxy)-3-{4-(4-methyl-piperazin-1-yl)-2-[(tetrahydro-pyran-4-yl)-(2,2,2-trifluoro-acetyl)-amino]-benzoylamino}indazole-1-carboxylic acid tert-butyl ester Triphenylphosphine (146 mg, 0.557 mmol) in DCM (2 mL), cooled at 4° C., in a nitrogen atmosphere was treated with neat diisopropyl azodicarboxylate (0.106 mL, 0.5208 mmol) while stirring. After 20 minutes the colourless solution was treated with 5-hydroxy-3-{4-(4-methyl-piperazin-1-yl)-2-[(tetrahydro-pyran-4-yl)-(2,2,2-trifluoro-acetyl)-amino]-benzoylamino}indazole-1-carboxylic acid tert-butyl ester (82 mg, 0.5108 mmol) in DCM (2 mL). After 2 hours the crude was purified by flash chromatography over silica gel (DCM:EtOH:35% NH$_4$OH 95:5:0.5) and 108 mg of title compound were obtained as a white solid in 59% yield.

ESI(+) MS: m/z 790 (MH$^+$).

Operating in an analogous way, the following compounds were obtained:

tert-butyl 5-[(2-fluorobenzyl)oxy]-3-[({4-(4-methylpiperazin-1-yl)-2-[tetrahydro-2H-pyran-4-yl(trifluoroacetyl)amino]phenyl}carbonyl)amino]-1H-indazole-1-carboxylate ESI(+) MS: m/z 755 (MH$^+$).

tert-butyl 5-[(4-fluorobenzyl)oxy]-3-[({4-(4-methylpiperazin-1-yl)-2-[tetrahydro-2H-pyran-4-yl(trifluoroacetyl)amino]phenyl}carbonyl)amino]-1H-indazole-1-carboxylate ESI(+) MS: m/z 755 (MH$^+$).

tert-butyl 5-[(2-methoxybenzyl)oxy]-3-[({4-(4-methylpiperazin-1-yl)-2-[tetrahydro-2H-pyran-4-yl(trifluoroacetyl)amino]phenyl}carbonyl)amino]-1H-indazole-1-carboxylate ESI(+) MS: m/z 767 (MH$^+$).

tert-butyl 5-[(2,3-difluorobenzyl)oxy]-3-[({4-(4-methylpiperazin-1-yl)-2-[tetrahydro-2H-pyran-4-yl(trifluoroacetyl)amino]phenyl}carbonyl)amino]-1H-indazole-1-carboxylate ESI(+) MS: m/z 773 (MH$^+$).

tert-butyl 5-[(3,4-difluorobenzyl)oxy]-3-[({4-(4-methylpiperazin-1-yl)-2-[tetrahydro-2H-pyran-4-yl(trifluoroacetyl)amino]phenyl}carbonyl)amino]-1H-indazole-1-carboxylate ESI(+) MS: m/z 773 (MH$^+$).

tert-butyl 5-[(3-chloro-5-fluorobenzyl)oxy]-3[({4-(4-methylpiperazin-1-yl)-2-[tetrahydro-2H-pyran-4-yl(trifluoroacetyl)amino]phenyl}carbonyl)amino]-1H-indazole-1-carboxylate ESI(+) MS: m/z 790 (MH$^+$).

tert-butyl 5-[(5-fluoro-2-methylbenzyl)oxy]-3-[({4-(4-methylpiperazin-1-yl)-2-[tetrahydro-2H-pyran-4-yl(trifluoroacetyl)amino]phenyl}carbonyl)amino]-1H-indazole-1-carboxylate ESI(+) MS: m/z 769 (MH$^+$).

tert-butyl 5-[(5-fluoro-3-methylbenzyl)oxy]-3-[({4-(4-methylpiperazin-1-yl)-2-[tetrahydro-2H-pyran-4-yl(trifluoroacetyl)amino]phenyl}carbonyl)amino]-1H-indazole-1-carboxylate ESI(+) MS: m/z 769 (MH⁺).

Conversion 4, Step D

Preparation of N-[5-(2-chloro-5-fluoro-benzyloxy)-1H-indazol-3-yl]-4-(4-methyl-piperazin-1-yl)-2-(tetrahydro-pyran-4-ylamino)-benzamide (Cpd. 19)

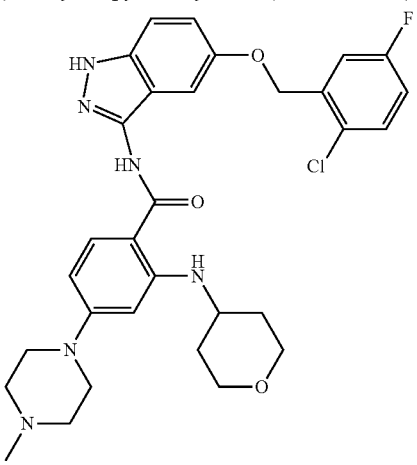

5-(2-Chloro-5-fluoro-benzyloxy)-3-{4-(4-methyl-piperazin-1-yl)-2-[(tetrahydro-pyran-4-yl)-(2,2,2-trifluoro-acetyl)-amino]-benzoylamino}-indazole-1-carboxylic acid tert-butyl ester (100 mg, 0.1269 mmol) in DCM (1.3 mL) was treated at room temperature with TFA (0.195 mL, 2.538 mmol). After 2 hours the volatiles were evaporated and the residue was treated with MeOH (3 mL) and TEA (0.357 mL, 2.538 mmol) and refluxed for three hours. After evaporation of the volatile components the crude was diluted with DCM (25 mL), washed with water, aqueous NaHCO₃, water and finally brine, dried over sodium sulfate, evaporated and purified by flash chromatography over silica gel (eluent: DCM: 7N NH₃ in MeOH 93:7) to give 40 mg of title compound.

1H-NMR (400 MHz), δ (ppm, DMSO-d₆): 1.29-1.42 (m, 2H) 1.90-1.98 (m, 2H) 2.24 (s, 3H) 2.43-2.48 (m, 4H) 3.25-3.29 (m, 4H) 3.45-3.54 (m, 2H) 3.64-3.74 (m, 1H) 3.82 (dt, J=11.61, 3.95 Hz, 2H) 5.13 (s, 2H) 6.14 (d, J=1.83 Hz. 1H) 6.24 (dd, J=8.96, 2.13 Hz, 1H) 7.13-7.17 (m, 2H) 7.26 (td, J=8.54, 3.17 Hz, 1H) 7.43 (d, J=9.51 Hz, 1H) 7.47-7.51 (m, 1H) 7.56 (dd, J=8.84, 5.06 Hz, 1H) 7.80 (d, J=9.15 Hz, 1H) 8.31 (d, J=7.80 Hz, 1H) 10.07 (s, 1H) 12.60 (s, 1H)

Operating in an analogous way, the following compounds were obtained:

N-{5-[(2-fluorobenzyl)oxy]-1H-indazol-3-yl}-4-(4-methylpiperazin-1-yl)-2-(tetrahydro-2H-pyran-4-ylamino)benzamide (Cpd. 14)

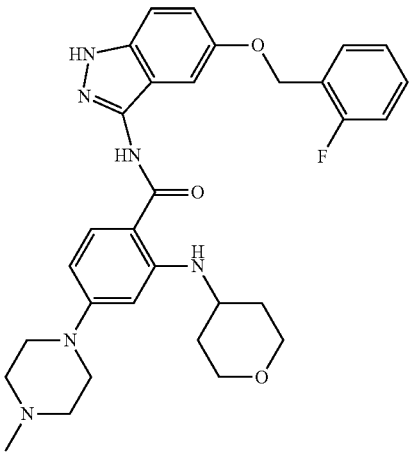 [SMILES: CN1CCN(c2ccc(C(=O)Nc3n[nH]c4ccc(OCc5ccccc5F)cc34)c(NC3CCOCC3)c2)CC1]

1H-NMR (400 MHz), δ (ppm, DMSO-d₆): 1.29-1.43 (m, 2H) 1.95 (dd, J=13.78, 2.44 Hz, 2H) 2.23 (s, 3H) 2.42-2.47 (m, 4H) 3.23-3.30 (m, 4H) 3.45-3.54 (m, 2H) 3.70 (m, 1H) 3.82 (dt, J=11.65, 3.87 Hz, 2H) 5.11 (s, 2H) 6.15 (d, J=2.19 Hz, 1H) 6.25 (dd, J=8.96, 2.26 Hz, 1H) 7.08 (dd, J=8.96, 2.38 Hz, 1H) 7.13 (d, J=2.19 Hz, 1H) 7.21-7.27 (m, 2H) 7.39-7.45 (m, 2H) 7.58 (td, J=7.65, 1.65 Hz, 1H) 7.80 (d, J=9.15 Hz, 1H) 8.30 (d, J=7.68 Hz, 1H) 10.05 (s, 1H) 12.58 (s, 1H)

N-{5-[(4-fluorobenzyl)oxy]-1H-indazol-3-yl}-4-(4-methylpiperazin-1-yl)-2-(tetrahydro-2H-pyran-4-ylamino)benzamide (Cpd. 28)

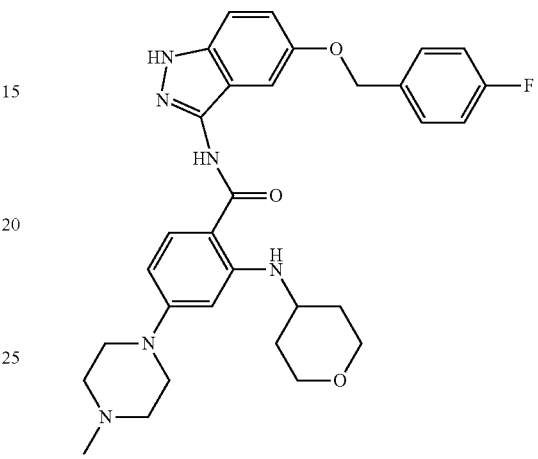

1H-NMR (400 MHz), δ (ppm, DMSO-d₆): 1.28-1.43 (m, 2H) 1.90-2.00 (m, 2H) 2.24 (s, 3H) 2.41-2.47 (m, 4H) 3.24-3.30 (m, 4H) 3.45-3.55 (m, 2H) 3.64-3.76 (m, 1H) 3.77-3.86 (m, 2H) 5.05 (s, 2H) 6.15 (d, J=1.83 Hz, 1H) 6.25 (d, J=8.78 Hz, 1H) 7.07-7.11 (m, 2H) 7.21 (t, J=8.78 Hz, 2H) 7.41 (d, J=9.75 Hz, 1H) 7.52 (dd, J=7.64, 5.06 Hz, 2H) 7.80 (d, J=9.02 Hz, 1H) 8.30 (d, J=7.68 Hz, 1H) 10.05 (s, 1H) 12.57 (s, 1H)

N-{5-[(2-methoxybenzyl)oxy]-1H-indazol-3-yl}-4-(4-methylpiperazin-1-yl)-2-(tetrahydro-2H-pyran-4-ylamino)benzamide (Cpd. 26)

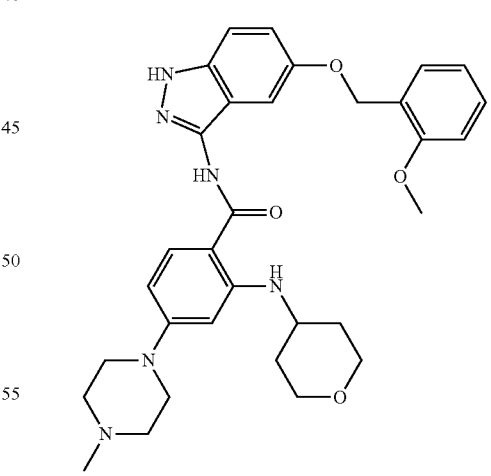

1H-NMR (400 MHz), δ (ppm, DMSO-d₆): 1.31-1.42 (m, 2H) 1.91-1.98 (m, 2H) 2.25 (s, 3H) 2.46 (br. s., 4H) 3.25-3.29 (m, 4H) 3.45-3.54 (m, 2H) 3.63-3.75 (m, 1H) 3.79 (s, 3H) 3.80-3.87 (m, 2H) 6.15 (d, J=1.95 Hz, 1H) 6.25 (dd, J=9.08, 2.13 Hz, 1H) 6.96 (td, J=7.44, 0.85 Hz, 1H) 7.03 (d, J=7.93 Hz, 1H) 7.05-7.09 (m, 2H) 7.29-7.35 (m, 1H) 7.38-7.41 (m, 1H) 7.44 (dd, J=7.50, 1.65 Hz, 1H) 7.80 (d, J=9.15 Hz. 1H) 8.30 (d, J=7.80 Hz, 1H) 10.05 (s, 1H) 12.55 (s, 1H)

N-{5-[(2,3-difluorobenzyl)oxy]-1H-indazol-3-yl}-4-(4-methylpiperazin-1-yl)-2-(tetrahydro-2H-pyran-4-ylamino)benzamide (Cpd. 12)

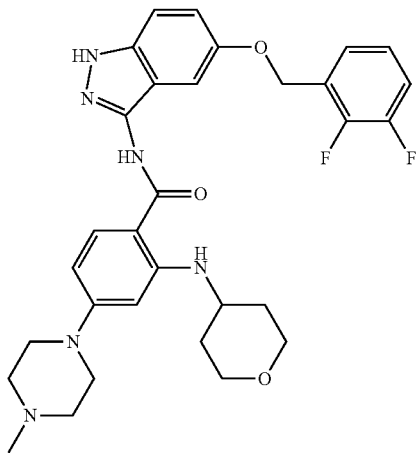 [SMILES: CN1CCN(c2ccc(C(=O)Nc3n[nH]c4ccc(OCc5cccc(F)c5F)cc34)c(NC3CCOCC3)c2)CC1]

1H-NMR (400 MHz), δ (ppm, DMSO-d$_6$): 1.30-1.43 (m, 2H) 1.88-2.00 (m, 2H) 2.25 (s, 3H) 2.46 (br. s., 4H) 3.25-3.31 (m, 4H) 3.45-3.54 (m, 2H) 3.65-3.73 (m, 1H) 3.77-3.86 (m, 2H) 5.17 (s, 2H) 6.15 (d, J=1.83 Hz, 1H) 6.25 (dd, J=8.96, 2.13 Hz, 1H) 7.09 (dd, J=8.90, 2.32 Hz, 1H) 7.14 (d, J=2.19 Hz, 1H) 7.19-7.28 (m, 1H) 7.36-7.47 (m, 3H) 7.80 (d, J=9.15 Hz, 1H) 8.29 (d, J=7.80 Hz, 1H) 10.06 (s, 1H) 12.59 (s, 1H)

N-{5-[(3,4-difluorobenzyl)oxy]-1H-indazol-3-yl}-4-(4-methylpiperazin-1-yl)-2-(tetrahydro-2H-pyran-4-ylamino)benzamide (Cpd. 13)

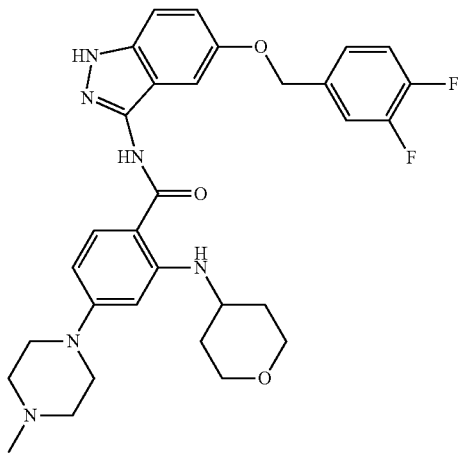 [SMILES: CN1CCN(c2ccc(C(=O)Nc3n[nH]c4ccc(OCc5ccc(F)c(F)c5)cc34)c(NC3CCOCC3)c2)CC1]

1H-NMR (400 MHz), δ (ppm, DMSO-d$_6$): 1.28-1.42 (m, 2H) 1.89-1.98 (m, 2H) 2.25 (br. s., 3H) 2.46 (br. s., 4H) 3.24-3.31 (m, 4H) 3.45-3.55 (m, 2H) 3.67 (br. s., 1H) 3.78-3.86 (m, 2H) 6.15 (d, J=1.95 Hz, 1H) 6.25 (dd, J=9.02, 2.07 Hz, 1H) 7.08 (d, J=2.07 Hz, 1H) 7.09-7.13 (m, 1H) 7.29-7.36 (m, 1H) 7.40-7.43 (m, 1H) 7.40-7.48 (m, 1H) 7.54 (ddd, J=11.52, 7.99, 1.95 Hz, 1H) 7.80 (d, J=9.15 Hz, 1H) 8.29 (d, J=6.56 Hz, 1H) 10.05 (s, 1H) 12.59 (s, 1H)

N-{5-[(3-chloro-5-fluorobenzyl)oxy]-1H-indazol-3-yl}-4-(4-methylpiperazin-1-yl)-2-(tetrahydro-2H-pyran-4-ylamino)benzamide (Cpd. 22)

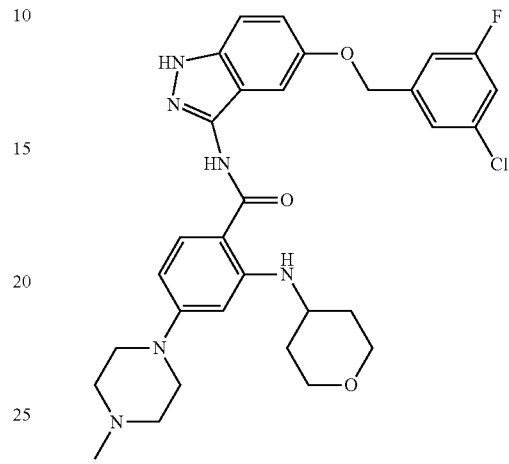

1H-NMR (400 MHz), δ (ppm, DMSO-d$_6$): 1.31-1.42 (m, 2H) 1.89-1.98 (m, 2H) 2.26 (br. s., 3H) 2.47 (br. s., 4H) 3.25-3.30 (m, 4H) 3.46-3.54 (m, 2H) 3.64-3.74 (m, 1H) 3.78-3.85 (m, 2H) 5.12 (s, 2H) 6.15 (d, J=2.19 Hz, 1H) 6.25 (dd, J=8.96, 2.13 Hz, 1H) 7.07 (d, J=2.32 Hz, 1H) 7.14 (dd, J=8.96, 2.38 Hz, 1H) 7.30-7.34 (m, 1H) 7.35-7.40 (m, 1H) 7.40 (s, 1H) 7.42 (d, J=9.02 Hz, 1H) 7.80 (d, J=9.15 Hz, 1H) 8.28 (d, J=7.68 Hz, 1H) 10.05 (s, 1H) 12.60 (s, 1H)

N-{5-[(5-fluoro-2-methylbenzyl)oxy]-1H-indazol-3-yl}-4-(4-methylpiperazin-1-yl)-2-(tetrahydro-2H-pyran-4-ylamino)benzamide (Cpd. 24)

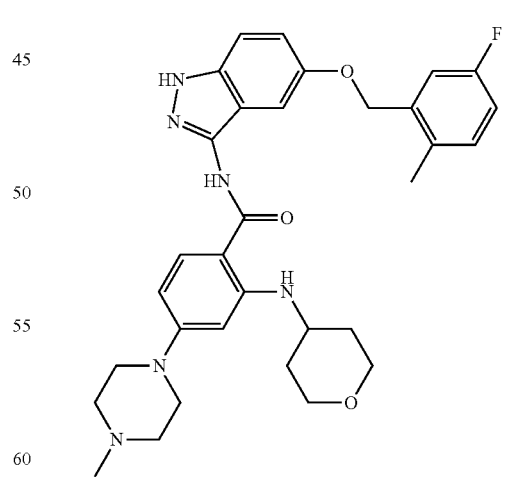

1H-NMR (400 MHz), δ (ppm, DMSO-d$_6$): 1.32-1.41 (m, 2H) 1.90-1.98 (m, 2H) 2.24 (s, 3H) 2.30 (s, 3H) 2.43-2.47 (m, 4H) 3.25-3.30 (m, 4H) 3.45-3.53 (m, 2H) 3.66-3.74 (m, 1H) 3.79-3.85 (m, 2H) 5.06 (s, 2H) 6.15 (d, J=2.07 Hz, 1H) 6.25 (dd, J=9.02, 2.32 Hz, 1H) 7.06 (td, J=8.57, 2.87 Hz, 1H)

7.10-7.15 (m, 2H) 7.22-7.30 (m, 2H) 7.40-7.44 (m, 1H) 7.80 (d, J=9.15 Hz, 1H) 8.32 (d, J=7.68 Hz, 1H) 10.06 (s, 1H) 12.59 (s, 1H)

N-{5-[(3-fluoro-5-methylbenzyl)oxy]-1H-indazol-3-yl}-4-(4-methylpiperazin-1-yl)-2H-pyran-4-ylamino)benzamide (Cpd. 23)

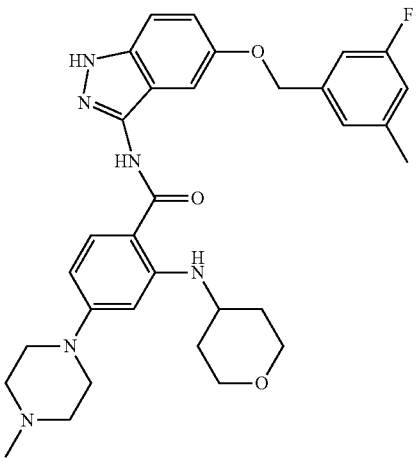 [SMILES: Cc1cc(F)cc(COc2ccc3[nH]nc(NC(=O)c4ccc(N5CCN(C)CC5)cc4NC4CCOCC4)c3c2)c1]

1H-NMR (400 MHz), δ (ppm, DMSO-$d_6$): 1.30-1.44 (m, 2H) 1.90-1.98 (m, 2H) 2.25 (s, 3H) 2.25 (s, 3H) 2.32 (s, 3H) 2.44-2.48 (m, 4H) 3.24-3.29 (m, 4H) 3.46-3.54 (m, 2H) 3.67-3.72 (m, 1H) 3.78-3.85 (m, 2H) 5.05 (s, 2H) 6.15 (d, J=2.20 Hz, 1H) 6.25 (dd, J=8.96, 2.26 Hz, 1H) 6.95-6.99 (m, 1H) 7.05-7.09 (m, 1H) 7.07 (d, J=2.44 Hz, 1H) 7.09-7.12 (m, 1H) 7.12-7.13 (m, 1H) 7.41 (d, J=9.27 Hz, 1H) 7.79 (d, J=9.02 Hz, 1H) 8.28 (d, J=7.80 Hz, 1H) 10.05 (s, 1H) 12.58 (s, 1H)

Example 3

Step d

Preparation of N-[5-(3,5-difluoro-benzyloxy)-1H-indazol-3-yl]-4-[(3-dimethylamino-propyl)-methyl-amino]-2-nitro-benzamide (Cpd. 21)

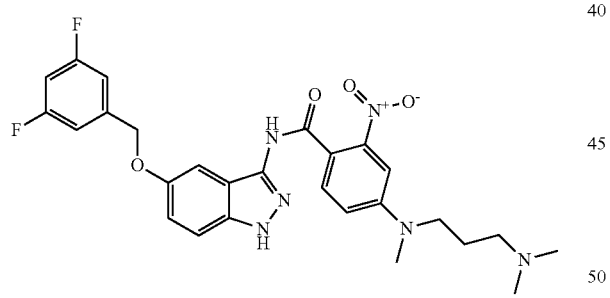

4-[(3-Dimethylamino-propyl)-methyl-amino]-2-nitro-benzoic acid hydrochloride (500 mg, 1.57 mmol) in dry THF (15 mL) was treated with one drop of DMF and with neat SOCl$_2$ (0.34 mL, 4.69 mmol). The reaction mixture was refluxed for 0.5 hours, evaporated. The residue was taken in toluene (10 mL) and evaporated to dryness to afford a yellow solid that was suspended in dry pyridine (15 mL), cooled to 4° C. and treated with 5-(3,5-difluoro-benzyloxy)-1H-indazol-3-ylamine (360 mg, 1.31 mmol) in pyridine (5 mL). The solution was left at 4° C. over night and evaporated. The residue was dissolved in DCM (250 mL), washed with saturated NaHCO$_3$ solution, water and brine. After drying over sodium sulfate and removal of the solvent, the crude was purified over silica gel (DCM: NH$_3$ 7N in MeOH 93:7) to afford 45 mg of title compound as an amorphous yellow solid (yield: 64%).

1H-NMR (400 MHz), δ (ppm, DMSO-$d_6$): 1.63-1.72 (m, 2H) 2.16 (s, 6H) 2.25 (t, J=6.10 Hz, 2H) 3.02 (s, 3H) 3.45-3.51 (m, 2H) 5.11 (s, 2H) 6.99 (d, J=9.27 Hz, 1H) 7.10-7.24 (m, 6H) 7.42 (d, J=8.90 Hz. 1H) 7.67 (d, J=5.61 Hz, 1H) 10.70 (br. s., 1H) 12.64 (s, 1H)

Operating in an analogous way, the following compounds were obtained:

N-[5-(benzyloxy)-1H-indazol-3-yl]-4-(4-methylpiperazin-1-yl)-2-nitrobenzamide (Cpd. 29)

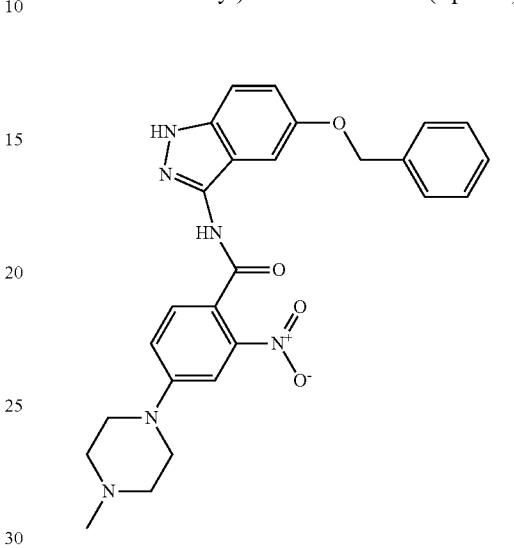

1H-NMR (400 MHz), δ (ppm, DMSO-$d_6$): 2.24 (s, 3H) 2.43-2.48 (m, 4H) 3.34-3.41 (m, 4H) 5.07 (s, 2H) 7.11 (dd, J=9.02, 2.19 Hz, 1H) 7.26 (d, J=2.07 Hz, 1H) 7.29 (br. s., 1H) 7.31-7.36 (m, 1H) 7.38-7.42 (m, 3H) 7.45 (s, 1H) 7.49 (d, J=7.68 Hz, 2H) 7.71 (d, J=4.88 Hz, 1H) 10.78 (br. s., 1H) 12.64 (s, 1H)

N-{5-[(3,5-difluorobenzyl)oxy]-1H-indazol-3-yl}-4-(4-methylpiperazin-1-yl)-2-nitrobenzamide (Cpd. 30)

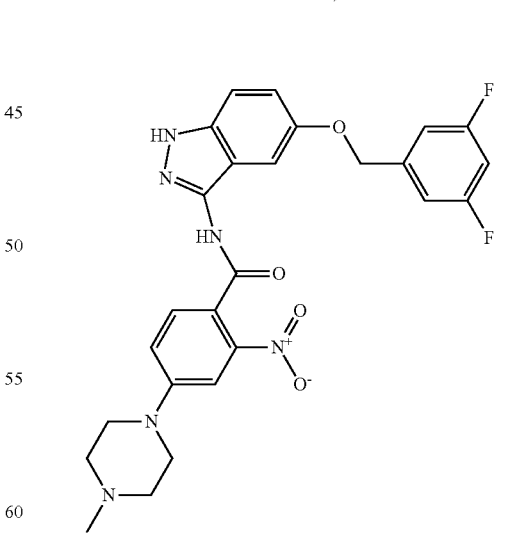

1H-NMR (400 MHz), δ (ppm, DMSO-$d_6$): 2.25 (s, 3H) 2.43-2.48 (m, 4H) 3.34-3.39 (m, 4H) 5.12 (s, 2H) 7.10-7.24 (m, 5H) 7.28 (d, J=10.85 Hz, 1H) 7.42 (d, J=9.02 Hz, 1H) 7.45 (br. s., 1H) 7.70 (d, J=5.85 Hz, 1H) 10.79 (br. s., 1H) 12.66 (s, 1H)

N-[5-(benzyloxy)-1H-indazol-3-yl]-4-{[3-(dimethylamino)propyl](methyl)amino}-2-nitrobenzamide (Cpd. 15)

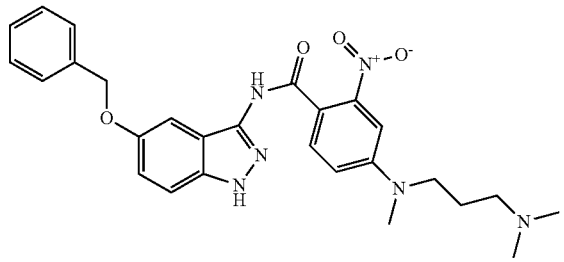 [SMILES: CN(C)CCCN(C)c1ccc(C(=O)Nc2n[nH]c3ccc(OCc4ccccc4)cc23)c([N+](=O)[O-])c1]

1H-NMR (400 MHz), δ (ppm, DMSO-d$_6$): 1.63-1.74 (m, 2H) 2.17 (s, 6H) 2.26 (t, J=6.83 Hz, 2H) 3.02 (s, 3H) 3.48 (t, J=6.40 Hz, 2H) 5.07 (s, 2H) 6.99 (d, J=8.17 Hz, 1H) 7.10 (dd, J=8.96, 2.38 Hz, 1H) 7.20 (d, J=2.56 Hz, 1H) 7.24 (d, J=2.19 Hz, 1H) 7.31-7.36 (m, 1H) 7.37-7.43 (m, 3H) 7.47-7.50 (m, 2H) 7.69 (d, J=11.22 Hz, 1H) 10.69 (br. s., 1H) 12.62 (s, 1H)

N-{5-[(3,5-difluorobenzyl)oxy]-1H-indazol-3-yl}-4-nitrobenzamide (Cpd. 64)

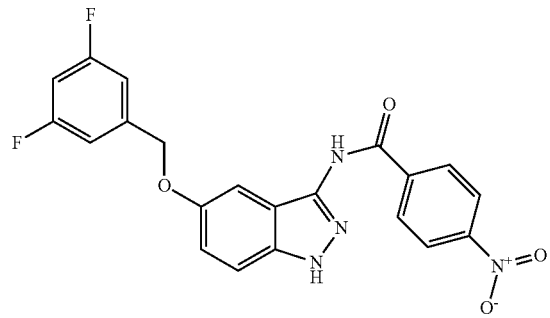 [SMILES: O=C(Nc1n[nH]c2ccc(OCc3cc(F)cc(F)c3)cc12)c1ccc([N+](=O)[O-])cc1]

1H-NMR (400 MHz), δ (ppm, DMSO-d$_6$): 5.12 (s, 2H) 7.13-7.24 (m, 5H) 7.45 (d, J=9.03 Hz, 1H) 8.26-8.31 (m, 2H) 8.36-8.41 (m, 2H) 11.05 (s, 1H) 12.78 (s, 1H)

N-{5-[(3,5-difluorobenzyl)oxy]-1H-indazol-3-yl}-3-nitrobenzamide (Cpd. 65)

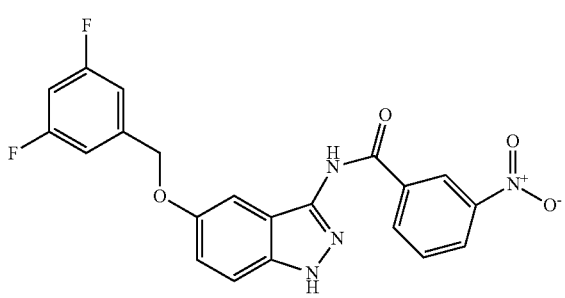 [SMILES: O=C(Nc1n[nH]c2ccc(OCc3cc(F)cc(F)c3)cc12)c1cccc([N+](=O)[O-])c1]

1H-NMR (400 MHz), δ (ppm, DMSO-d$_6$): 5.11 (s, 2H) 7.12-7.25 (m, 5H) 7.45 (d, J=9.03 Hz, 1H) 7.86 (t, J=8.06 Hz, 1H) 8.47 (dd, J=8.18, 1.46 Hz, 1H) 8.50 (d, J=7.69 Hz, 1H) 8.90 (s, 1H) 11.10 (s, 1H) 12.77 (s, 1H)

N-[5-(3,5-difluorophenoxy)-1H-indazol-3-yl]-3-nitrobenzamide (Cpd. 87)

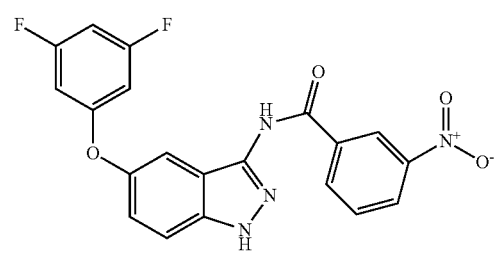 [SMILES: O=C(Nc1n[nH]c2ccc(Oc3cc(F)cc(F)c3)cc12)c1cccc([N+](=O)[O-])c1]

1H-NMR (400 MHz), δ (ppm, DMSO-d$_6$): 6.57-6.68 (m, 2H) 6.87-6.98 (m, 1H) 7.22 (d, J=9.03 Hz, 1H) 7.56 (s, 1H) 7.61 (d, J=8.67 Hz, 1H) 7.80-7.88 (m, 1H) 8.42-8.50 (m, 2H) 8.87 (s, 1H) 11.25 (s, 1H) 13.03 (s, 1H)

N-[5-(3,5-difluorophenoxy)-1H-indazol-3-yl]-4-nitrobenzamide (Cpd. 88)

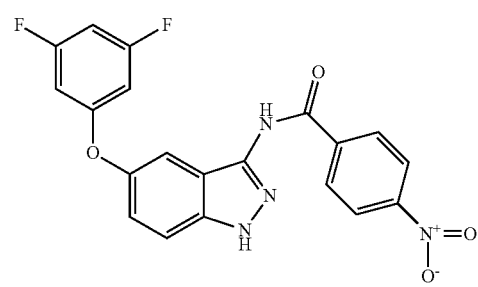 [SMILES: O=C(Nc1n[nH]c2ccc(Oc3cc(F)cc(F)c3)cc12)c1ccc([N+](=O)[O-])cc1]

1H-NMR (400 MHz), δ (ppm, DMSO-d$_6$): 6.60-6.68 (m, 2H) 6.92 (tt, J=9.34, 2.32 Hz, 1H) 7.22 (dd, J=8.97, 2.26 Hz, 1H) 7.55 (d, J=2.20 Hz, 1H) 7.60 (d, J=8.91 Hz, 1H) 8.26 (d, J=8.54 Hz, 2H) 8.33-8.39 (m, 2H) 11.19 (s, 1H) 13.03 (s, 1H)

Conversion 1

Preparation of 2-amino-N-[5-(3,5-difluoro-benzyloxy)-1H-indazol-3-yl]-4-[(3-dimethylamino-propyl)-methyl-amino]-benzamide (Cpd. 18)

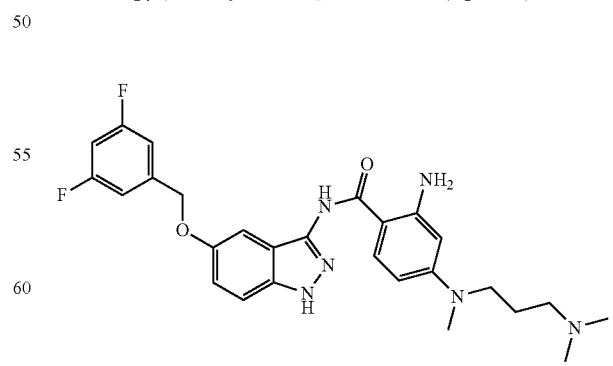

N-[5-(3,5-Difluoro-benzyloxy)-1H-indazol-3-yl]-4-[(3-dimethylamino-propyl)-methyl-amino]-2-nitro-benzamide (424 mg, 0.79 mmol) in DCM (5 mL) was treated with nBu₄NCl (149 mg, 0.54 mmol). Na₂S₂O₄ (969 mg, 4.73 mmol) in water (5 mL) was added drop-wise, with stirring. After 1 hour, the volatiles were removed by evaporation, the residue was taken twice in water, filtered and treated with 4N HCl in dioxane (12 mL). The volatile components were removed by evaporation. The solid was dissolved in DCM (100 mL), washed with saturated NaHCO₃ solution and brine. After drying over sodium sulfate and removal of the solvent, the crude was purified over silica gel (DCM: NH₃ 7N in MeOH 9:1) to afford 260 mg of title compound in 65% yield.

1H-NMR (400 MHz), δ (ppm, DMSO-d₆):1.59-1.71 (m, 2H) 2.17 (s, 6H) 2.25 (t, 2H) 2.91 (s, 3H) 3.30-3.39 (m, 2H) 5.11 (s, 2H) 5.95 (d, J=2.56 Hz, 1H) 6.05 (dd, J=9.02, 2.44 Hz, 1H) 6.54 (s, 2H) 7.10-7.14 (m, 2H) 7.14-7.19 (m, 1H) 7.19-7.24 (m, 2H) 7.38-7.43 (m, 1H) 7.70 (d, J=9.02 Hz, 1H) 9.88 (s, 1H) 12.53 (s, 1H)

Operating in an analogous way, the following compounds were obtained:

2-amino-N-[5-(benzyloxy)-1H-indazol-3-yl]-4-{[3-(dimethylamino)propyl](methyl)amino}benzamide (Cpd. 27)

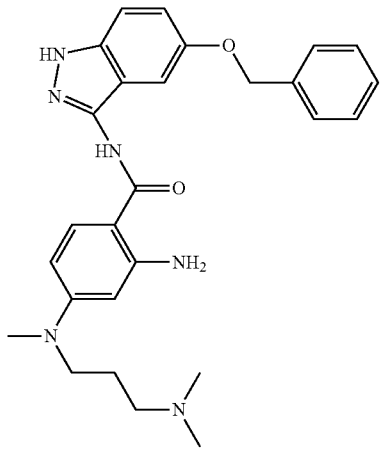 [SMILES: CN(C)CCCN(C)c1ccc(C(=O)Nc2n[nH]c3ccc(OCc4ccccc4)cc23)c(N)c1]

1H-NMR (400 MHz), δ (ppm, DMSO-d₆): 1.62-1.73 (m, 2H) 2.18 (s, 6H) 2.28 (t, J=6.71 Hz, 2H) 2.91 (s, 3H) 3.28-3.39 (m, 2H) 5.06 (s, 2H) 5.95 (d, J=2.44 Hz, 1H) 6.05 (dd, J=9.08, 2.50 Hz, 1H) 6.54 (s, 2H) 7.08 (dd, J=8.96, 2.38 Hz, 1H) 7.11-7.13 (m, 1H) 7.30-7.35 (m, 1H) 7.36-7.41 (m, 3H) 7.45-7.49 (m, 2H) 7.70 (d, J=9.02 Hz. 1H) 9.87 (s, 1H) 12.50 (s, 1H)

N-{5-[(3,5-difluorobenzyl)oxy]-1H-indazol-3-yl}-4-amino-benzamide (Cpd. 94)

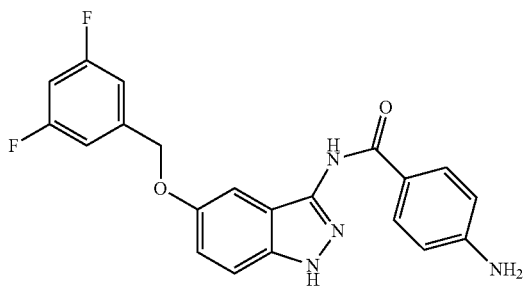 [SMILES: Nc1ccc(C(=O)Nc2n[nH]c3ccc(OCc4cc(F)cc(F)c4)cc23)cc1]

ESI(+) MS: m/z 395 (MH⁺).

N-{5-[(3,5-difluorobenzyl)oxy]-1H-indazol-3-yl}-3-amino-benzamide (Cpd. 95)

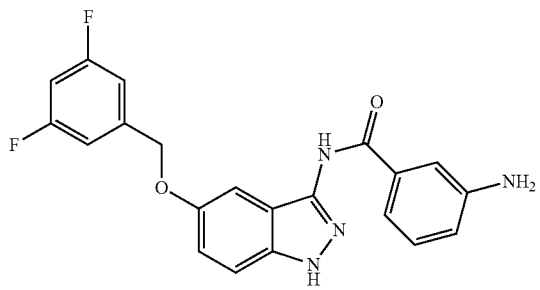 [SMILES: Nc1cccc(C(=O)Nc2n[nH]c3ccc(OCc4cc(F)cc(F)c4)cc23)c1]

ESI(+) MS: m/z 395 (MH⁺).

4-amino-N-[5-(3,5-difluorophenoxy)-1H-indazol-3-yl]benzamide (Cpd. 90)

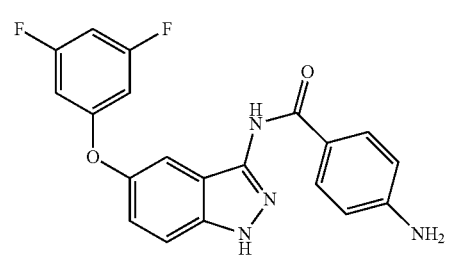 [SMILES: Nc1ccc(C(=O)Nc2n[nH]c3ccc(Oc4cc(F)cc(F)c4)cc23)cc1]

1H-NMR (400 MHz), δ (ppm, DMSO-d₆): 5.74 (s, 2H) 6.58 (d, J=8.79 Hz, 2H) 6.62 (dd, J=8.79, 2.20 Hz, 2H) 6.91 (tt, J=9.29, 2.36 Hz, 1H) 7.18 (dd, J=8.91, 2.32 Hz, 1H) 7.45 (dd, J=2.38, 0.43 Hz, 1H) 7.55 (dd, J=8.97, 0.55 Hz, 1H) 7.77 (d, J=8.67 Hz, 2H) 10.30 (s, 1H) 12.82 (br. s., 1H)

3-amino-N-[5-(3,5-difluorophenoxy)-1H-indazol-3-yl]benzamide (Cpd. 89)

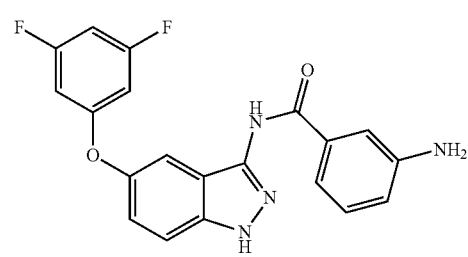 [SMILES: Nc1cccc(C(=O)Nc2n[nH]c3ccc(Oc4cc(F)cc(F)c4)cc23)c1]

1H-NMR (400 MHz), δ (ppm, DMSO-d₆): 5.26 (s, 2H) 6.59-6.68 (m, 2H) 6.75 (ddd, J=7.78, 2.17, 1.28 Hz, 1H) 6.92 (tt, J=9.29, 2.30 Hz, 1H) 7.13 (t, J=7.87 Hz, 1H) 7.19 (dd, J=8.91, 2.44 Hz, 1H) 7.20 (d, J=2.32 Hz, 1H) 7.45 (d, J=2.20 Hz, 1H) 7.57 (d, J=9.03 Hz, 1H) 10.54 (s, 1H) 12.89 (s, 1H)

Conversion 2

Preparation of N-[2-({5-[(3,5-difluorobenzyl)oxy]-1H-indazol-3-yl}carbamoyl)-5-{[3-(dimethylamino)propyl](methyl)amino}phenyl]-1H-pyrrole-2-carboxamide (Cpd. 25)

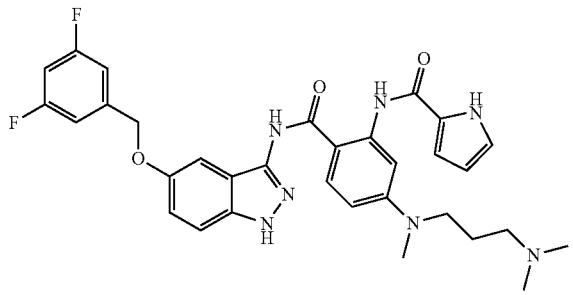 [SMILES: CN(C)CCCN(C)c1ccc(C(=O)Nc2n[nH]c3ccc(OCc4cc(F)cc(F)c4)cc23)c(NC(=O)c2ccc[nH]2)c1]

2-Amino-N-[5-(3,5-difluoro-benzyloxy)-1H-indazol-3-yl]-4-[(3-dimethylamino-propyl)-methyl-amino]-benzamide (115 mg, 0.23 mmol) in pyridine (2.2 mL), cooled to 4° C., was treated with solid 1H-pyrrole-2-carbonyl chloride (34 mg, 0.27 mmol). The reaction was stirred until clear and left to room temperature over night. After removal of the volatiles, the crude was purified over silica gel to afford 90 mg of title compound in 66% yield.

1H-NMR (400 MHz), δ (ppm, DMSO-$d_6$): 1.70-1.81 (m, 2H) 2.24 (br. s., 6H) 2.31-2.42 (m, 2H) 3.03 (s, 3H) 3.47 (t, J=7.01 Hz, 2H) 5.09 (s, 2H) 6.09 (dt, J=3.63, 2.39 Hz, 1H) 6.51 (dd, J=9.08, 2.62 Hz, 1H) 6.67 (ddt, J=3.66, 1.83 Hz, 1H) 6.96 (td, J=2.62, 1.46 Hz, 1H) 7.07-7.20 (m, 5H) 7.44-7.49 (m, 1H) 8.01 (d, J=9.27 Hz, 1H) 8.19 (d, J=2.56 Hz, 1H) 10.49 (s, 1H) 11.75 (br. s., 1H) 12.65 (s, 1H) 12.73 (s, 1H)

Conversion 3

Preparation of N-[5-(3,5-Difluoro-benzyloxy)-1H-indazol-3-yl]-4-[(3-dimethylamino-propyl)-methyl-amino]-2-(tetrahydro-pyran-4-ylamino)-benzamide (Cpd. 20)

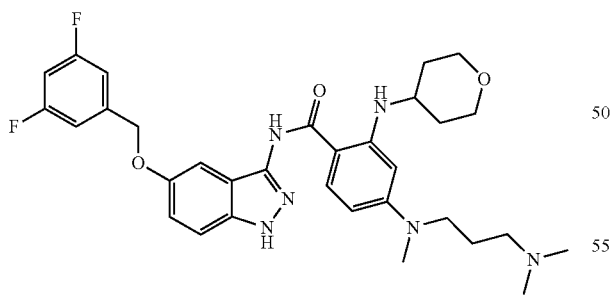

2-Amino-N-[5-(3,5-difluoro-benzyloxy)-1H-indazol-3-yl]-4-[(3-dimethylamino-propyl)-methyl-amino]-benzamide (150 mg, 0.29 mmol) in DCM (4 mL) was treated, at 4° C., under a nitrogen atmosphere, with tetrahydro-4H-pyran-4-one (0.34 mL, 0.37 mmol), TFA (0.23 mL, 2.95 mmol) and finally with tetramethylammonium triacetoxyborohydride ((204 mg, 0.74 mmol). After 1.5 hours DCM, was added (25 mL) and the organic layer was washed with water (25 mL), saturated NaHCO₃ solution (25 mL) and brine. After drying over anhydrous sodium sulfate, removal of the solvent and purification of the crude over silica gel (DCM: 7N NH₃ in MeOH 9:1), 80 mg of title compound were obtained in 46% yield.

1H-NMR (400 MHz), δ (ppm, DMSO-$d_6$): 1.37 (m, J=13.18, 9.75, 9.75, 4.02 Hz, 2H) 1.67 (quin, J=6.95 Hz, 2H) 1.95 (dq, J=13.34, 2.95 Hz, 2H) 2.20 (br. s., 6H) 2.30 (br. s., 2H) 2.95 (s, 3H) 3.39 (t, J=13 Hz, 2H) 3.47 (ddd, J=11.83, 9.94, 2.26 Hz, 2H) 3.58-3.68 (m, 1H) 3.82 (dt, J=11.61, 3.83 Hz, 2H) 5.11 (s, 2H) 5.87 (d, J=2.07 Hz, 1H) 6.04 (dd, J=9.08, 2.26 Hz, 1H) 7.06 (d, J=2.19 Hz, 1H) 7.12 (dd, J=9.02, 2.44 Hz, 1H) 7.19 (m, 2H) 7.41 (d, J=8.90 Hz, 1H) 7.76 (d, J=9.15 Hz, 1H) 8.33 (d, J=7.56 Hz, 1H) 9.93 (s, 1H) 12.56 (s, 1H)

Operating in an analogous way, the following compounds were obtained:

N-{5-[(3,5-difluorobenzyl)oxy]-1H-indazol-3-yl}-3-[(1-methylpiperidin-4-yl)amino]benzamide (Cpd. 66)

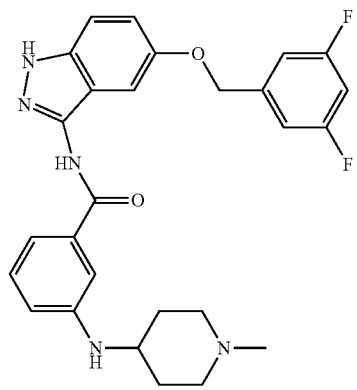 [SMILES: CN1CCC(Nc2cccc(C(=O)Nc3n[nH]c4ccc(OCc5cc(F)cc(F)c5)cc34)c2)CC1]

1H-NMR (400 MHz), δ (ppm, DMSO-$d_6$): ppm 1.46 (q, J=10.94 Hz, 2H) 1.95 (d, J=13.67 Hz, 2H) 2.29 (br. s., 5H) 2.87 (br. s., 2H) 3.31 (m, 1H) 5.10 (s, 2H) 5.72 (d, J=7.32 Hz, 1H) 6.80 (dt, J=7.11, 2.06 Hz, 1H) 7.10-7.25 (m, 8H) 7.43 (d, J=9.64 Hz, 1H) 10.44 (s, 1H) 12.66 (s, 1H)

N-{5-[(3,5-difluorobenzyl)oxy]-1H-indazol-3-yl}-4-[(1-methylpiperidin-4-yl)amino]benzamide (Cpd. 67)

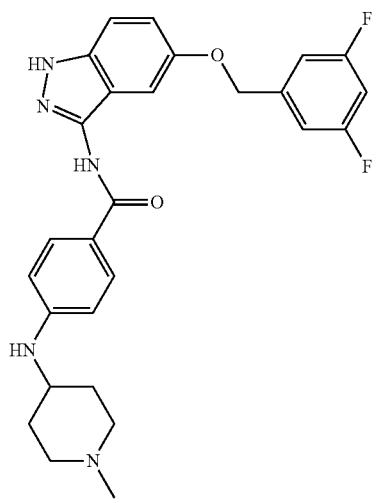 [SMILES: CN1CCC(Nc2ccc(C(=O)Nc3n[nH]c4ccc(OCc5cc(F)cc(F)c5)cc34)cc2)CC1]

1H-NMR (400 MHz), δ (ppm, DMSO-d$_6$): 1.43 (qd, J=11.50, 3.80 Hz, 2H) 1.90 (dd, J=13.30, 2.69 Hz. 2H) 2.03 (td, J=11.47, 2.08 Hz, 2H) 2.18 (s, 3H) 2.74 (dt, J=11.78, 3.14 Hz, 2H) 3.31 (m, 1H) 5.09 (s, 2H) 6.15 (d, J=7.81 Hz, 1H) 6.63 (d, J=8.79 Hz, 2H) 7.08-7.22 (m, 5H) 7.40 (dd, J=8.79, 0.61 Hz, 1H) 7.84 (d, J=8.79 Hz, 2H) 10.16 (s, 1H) 12.57 (s, 1H)

N-[5-(3,5-difluorophenoxy)-1H-indazol-3-yl]-3-[(1-methylpiperidin-4-yl)amino]benzamide (Cpd. 91)

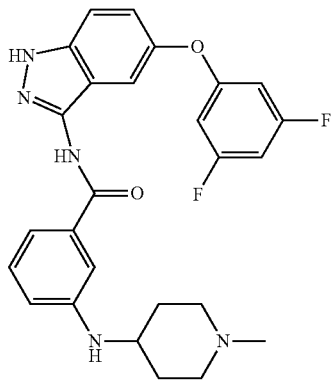 [SMILES: CN1CCC(Nc2cccc(C(=O)Nc3n[nH]c4ccc(Oc5cc(F)cc(F)c5)cc34)c2)CC1]

1H-NMR (400 MHz), δ (ppm, DMSO-d$_6$): 1.40 (qd, J=11.70, 3.50 Hz, 2H) 1.89 (d, J=13.06 Hz, 2H) 2.02 (t, J=12.33 Hz, 2H) 2.17 (s, 3H) 2.73 (dt, J=11.66, 3.75 Hz, 2H) 3.31 (m, 1H) 5.65 (d, J=8.06 Hz, 1H) 6.57-6.69 (m, 2H) 6.77 (ddd, J=5.58, 3.11, 2.90 Hz, 1H) 6.92 (tt, J=9.32, 2.27 Hz, 1H) 7.13-7.18 (m, 3H) 7.19 (dd, J=8.91, 2.32 Hz, 1) 7.45 (d, J=2.20 Hz, 1H) 7.58 (d, J=9.40 Hz, 1H) 10.60 (s, 1H) 12.91 (s, 1H)

N-[5-(3,5-difluorophenoxy)-1H-indazol-3-yl]-4-[(1-methylpiperidin-4-yl)amino]benzamide (Cpd. 92)

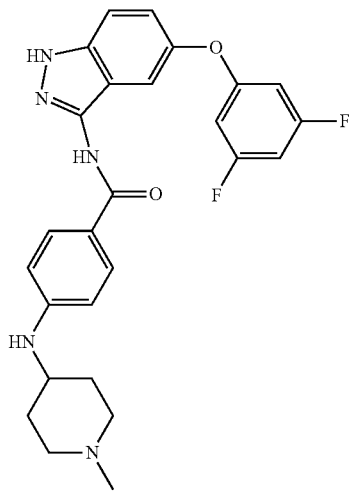 [SMILES: CN1CCC(Nc2ccc(C(=O)Nc3n[nH]c4ccc(Oc5cc(F)cc(F)c5)cc34)cc2)CC1]

1H-NMR (400 MHz), δ (ppm, DMSO-d$_6$): 1.51 (q, J=11.00 Hz, 2H) 1.96 (d, J=12.21 Hz, 2H) 2.39 (br. s., 5H) 2.97 (br. s., 2H) 3.39 (br. s., 1H) 6.24 (d, J=7.81 Hz, 1H) 6.56-6.68 (m, 4H) 6.91 (tt, J=9.29, 2.30 Hz, 1H) 7.18 (dd, J=8.97, 2.38 Hz, 1H) 7.45 (d, J=2.20 Hz, 1H) 7.56 (d, J=9.03 Hz, 1H) 7.83 (d, J=8.79 Hz, 2H) 10.34 (s, 1H) 12.83 (s, 1H)

Example 4

Step d

Preparation of 3-chloromethyl-N-[5-(3,5-difluoro-benzyloxy)-1H-indazol-3-yl]-benzamide (Cpd. 40)

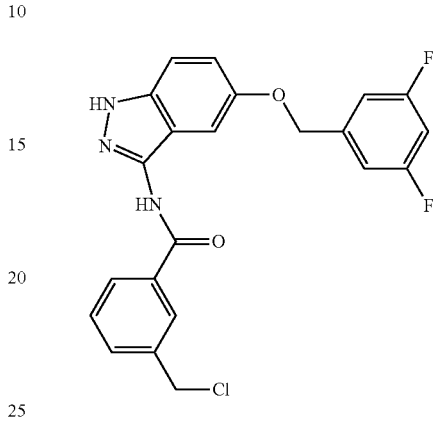

5-(3,5-Difluoro-benzyloxy)-1H-indazol-3-ylamine (550 mg, 2 mmol) was dissolved in sym-collidine, cooled to 4° C. and treated with neat 3-chloromethyl-benzoyl chloride (0.34 mL, 2.4 mmol). After 1 hour the reaction mixture was added drop wise into iced water, with stirring and separation of a yellow oil occurred. Then, EtOAc (50 mL) and 2N HCl (25 mL) were added. The organic phase was separated, washed with aqueous NaHCO$_3$ (50 mL), brine, dried over sodium sulfate and evaporated to dryness. After purification over silica gel (eluent: DCM:MeOH 95:5) 378 mg of title compound were obtained as a whitish solid in 56% yield.

1H-NMR (400 MHz), δ (ppm, DMSO-d$_6$): 4.88 (s, 2H) 5.12 (s, 2H) 7.14-7.17 (m, 1H) 7.18-7.25 (m, 4H) 7.45 (d, J=8.90 Hz, 1H) 7.57 (t, J=7.68 Hz, 1H) 7.69 (d, J=7.68 Hz, 1H) 8.06 (d, J=8.05 Hz, 1H) 8.14 (s, 1H) 10.75 (s, 1) 12.72 (s, 1H)

Operating in an analogous way, the following compound was obtained:

4-chloromethyl-N-[5-(3,5-difluoro-benzyloxy)-1H-indazol-3-yl]-benzamide (Cpd. 96)

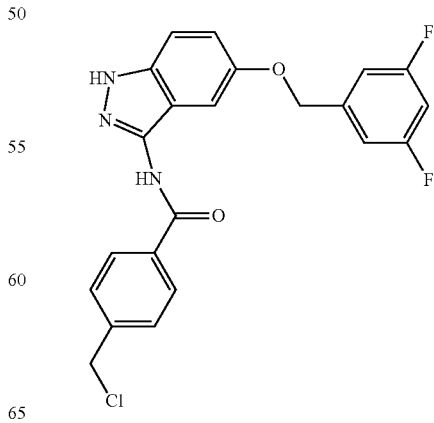

ESI(+) MS: m/z 428 (MH$^+$).

Preparation of N-[5-(3,5-difluoro-benzyloxy)-1H-indazol-3-yl]-3-piperidin-1-ylmethyl-benzamide (Cpd. 41)

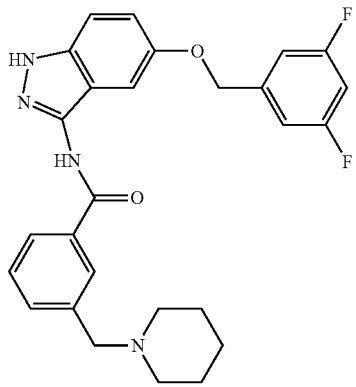 [SMILES: O=C(Nc1n[nH]c2ccc(OCc3cc(F)cc(F)c3)cc12)c1cccc(CN2CCCCC2)c1]

3-Chloromethyl-N-[5-(3,5-difluoro-benzyloxy)-1H-indazol-3-yl]-benzamide (100 mg, 0.2342 mmol) in absolute ethanol (2.5 mL) was treated with DIPEA (0.12 mL, 0.7026 mmol) and piperidine (0.069 mL, 0.7026 mmol) and heated to reflux temperature. After 1 hour the reaction mixture was diluted with water, filtered with suction and dried at 50° C. under vacuum. Purification by flash chromatography over silica gel (eluent: DCM:MeOH:7N $NH_3$ in MeOH 95:5:0.5) afforded 74 mg of title compound in 66% yield.

1H-NMR (400 MHz), δ (ppm, DMSO-$d_6$): 1.34-1.45 (m, 2H) 1.51 (quin, J=5.40 Hz, 4H) 2.36 (br. s., 4H) 3.50 (s, 2H) 5.11 (s, 2H) 7.14 (dd, J=8.90, 2.32 Hz, 1H) 7.18-7.22 (m, 4H) 7.43 (dd, J=8.90, 0.49 Hz, 1H) 7.48 (t, J=7.45 Hz, 1H) 7.53 (dt, J=7.56, 1.50 Hz, 1H) 7.95 (d, J=8.78 Hz, 1H) 7.96 (s, 1H) 10.65 (s, 1H) 12.69 (s, 1H)

Operating in an analogous way, the following compounds were obtained:

N-{5-[(3,5-difluorobenzyl)oxy]-1H-indazol-3-yl}-3-(pyrrolidin-1-ylmethyl)benzamide (Cpd. 43

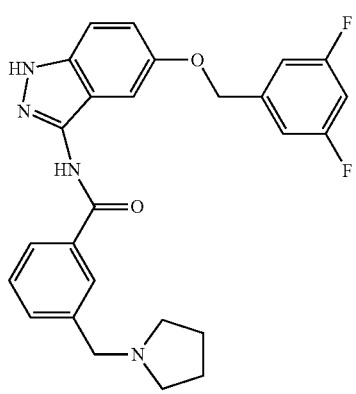 [SMILES: O=C(Nc1n[nH]c2ccc(OCc3cc(F)cc(F)c3)cc12)c1cccc(CN2CCCC2)c1]

1H-NMR (400 MHz), δ (ppm, DMSO-$d_6$): 1.64-1.80 (m, 4H) 2.47 (br. s., 4H) 3.66 (s, 2H) 5.11 (s, 2H) 7.14 (dd, J=8.90, 2.44 Hz, 1H) 7.17 (d, J=2.40 Hz, 1H) 7.21 (m, 3H) 7.43 (dd, J=8.90, 0.49 Hz, 1H) 7.47 (t, J7.62 Hz, 1) 7.54 (dt, J=7.68, 1.40 Hz, 1H) 7.95 (d, J=7.68 Hz, 1H) 7.99 (s, 1H) 10.66 (s, 1H) 12.69 (s, 1H)

3-(azetidin-1-ylmethyl)-N-{5-[(3,5-difluorobenzyl)oxy]-1H-indazol-3-yl}benzamide (Cpd. 42)

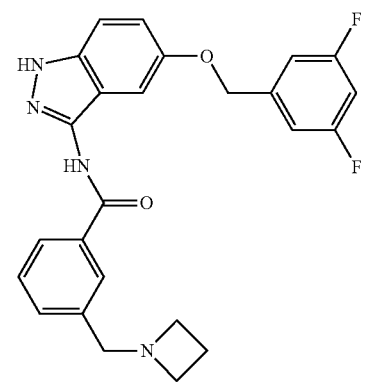 [SMILES: O=C(Nc1n[nH]c2ccc(OCc3cc(F)cc(F)c3)cc12)c1cccc(CN2CCC2)c1]

1H-NMR (400 MHz), δ (ppm, DMSO-$d_6$): 2.00 (quin, J=6.95 Hz, 2H) 3.16 (t, J=6.95 Hz, 4H) 3.60 (s, 2) 5.11 (s, 2H) 7.14 (dd, J=8.90, 2.44 Hz, 1H) 7.17 (d, J=2.44 Hz, 1H) 7.21 (m, 3H) 7.44 (dd, J=8.90, 0.61 Hz, 1H) 7.46 (dt, J=7.30 Hz, 1H) 7.50 (dt, J=7.40, 1.70 Hz, 1H) 7.93 (dt, J=7.56, 1.71 Hz, 1H) 7.95 (d, J=1.22 Hz, 1H) 10.65 (s, 1H) 12.69 (s, 1H)

N-{5-[(3,5-difluorobenzyl)oxy]-1H-indazol-3-yl}-4-(piperidin-1-ylmethyl)benzamide (Cpd. 61)

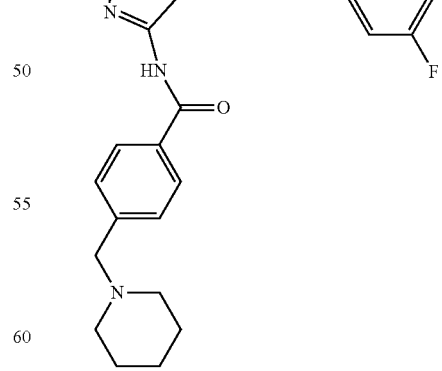

1H-NMR (400 MHz), δ (ppm, DMSO-$d_6$): 1.31-1.45 (m, 2H) 1.45-1.61 (m, 4H) 2.35 (br. s., 4H) 3.51 (br. s., 2H) 5.10

(s, 2H) 7.13-7.22 (m, 5H) 7.43 (d, J=8.78 Hz, 1H) 7.45 (d, J=8.17 Hz, 2H) 8.02 (d, J=7.93 Hz, 2H) 10.61 (s, 1H) 12.68 (s, 1H)

N-{5-[(3,5-difluorobenzyl)oxy]-1H-indazol-3-yl}-4-(morpholin-4-ylmethyl)benzamide (Cpd. 62)

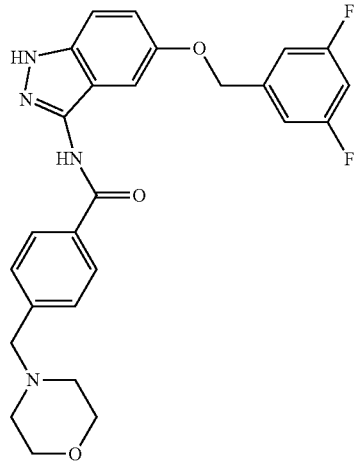 [SMILES: O=C(Nc1n[nH]c2ccc(OCc3cc(F)cc(F)c3)cc12)c1ccc(CN2CCOCC2)cc1]

1H-NMR (400 MHz), δ (ppm, DMSO-d₆): 2.39 (t, J=5.00 Hz, 4H) 3.56 (s, 2H) 3.60 (t, J=4.50 Hz, 4H) 5.10 (s, 2H) 7.12-7.22 (m, 5H) 7.43 (dd, 1H) 7.47 (d, J=8.29 Hz, 2H) 8.03 (d, J=8.17 Hz, 2H) 10.62 (s, 1H) 12.68 (s, 1H)

Example 5

Preparation of N-[5-(benzyloxy)-1H-indazol-3-yl]-1-(piperidin-4-yl)-1H-pyrazole-4-carboxamide hydrochloride (Cpd. 51)

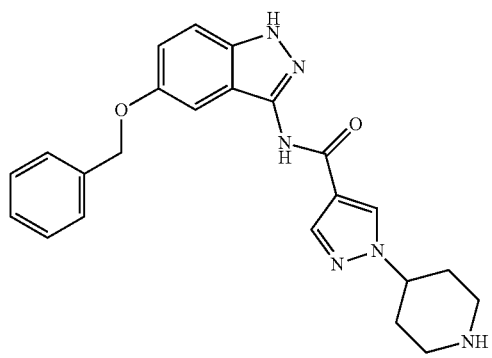 [SMILES: O=C(Nc1n[nH]c2ccc(OCc3ccccc3)cc12)c1cnn(C2CCNCC2)c1]

To a solution of tert-butyl 4-(4-{[5-(benzyloxy)-1H-indazol-3-yl]carbamoyl}-1H-pyrazol-1-yl)piperidine-1-carboxylate (100 mg, 0.19 mmol) in dioxane (4 mL), 4M HCl in dioxane (0.72 ml, 2.88 mmol) was added. The mixture was stirred at room temperature for 18 hours. The solvent was removed under reduced pressure and the crude was diluted with Et₂O and decanted, to give after filtration, the final compound as hydrochloride salt (80 mg, 93%).

1H-NMR (400 MHz), δ (ppm, DMSO-d₆): 2.15 (br. s., 2H) 2.25 (br. s., 2H) 3.03-3.17 (m, 2H) 3.38-3.46 (m, 2H) 4.54-4.63 (m, 1H) 5.06 (s, 2H) 7.11 (dd, J=9.02, 2.44 Hz, 1H) 7.23 (d, J=2.19 Hz, 1H) 7.31-7.36 (m, 1H) 7.37-7.43 (m, 3H) 7.46-7.50 (m, 2H) 8.16 (s, 1H) 8.49 (s, 1H) 8.67-8.81 (m, 8.17 Hz, 1H) 10.40 (s, 1) 12.65 (br. s., 1H)

Operating in an analogous way, the following compound was obtained:

N-[5-(benzyloxy)-1H-indazol-3-yl]-3-(piperazin-1-yl)benzamide hydrochloride (Cpd. 53)

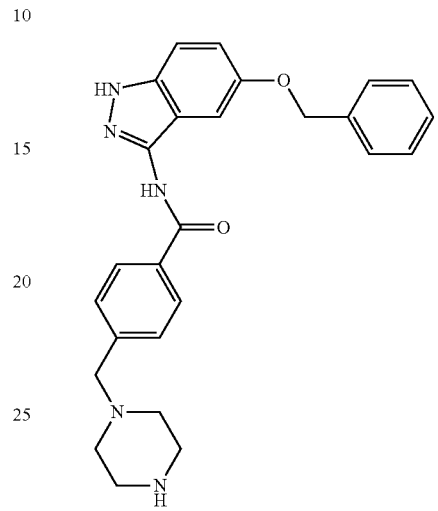

1H-NMR (400 MHz), δ (ppm, DMSO-d₆): 3.27 (br. s., 4H) 3.46-3.52 (m, 4H) 5.06 (s, 2H) 7.12 (dd, J=9.02, 2.44 Hz, 1H) 7.20 (d, J=2.07 Hz, 1H) 7.25 (dd, J=8.29, 1.83 Hz, 1H) 7.31-7.36 (m, 1H) 7.37-7.41 (m, 2H) 7.44 (m, 2H) 7.46-7.50 (m, 2H) 7.58 (d, J=7.56 Hz, 1H) 7.67 (s, 1H) 9.02 (br. s., 2H) 10.66 (s, 1H) 12.70 (br. s., 1H)

Preparation 3

Preparation of 4-fluoro-2-nitro-benzoic acid tert-butyl ester

A solution of 4-fluoro-2-nitro benzoic acid (10 g, 54 mmol), (Boc)₂O (2 eq., 23.6 g, 108 mmol) and 4-(N,N-dimethylamino)pyridine (0.3 eq., 1.98 g, 16.2 mmol) in tert-butanol (100 mL) and dichloromethane (100 mL) was stirred at room temperature for 20 hours. The reaction mixture was then diluted with ethyl acetate (500 mL), washed with 1N HCl (500 mL), water (500 mL), brine (500 mL), dried over sodium sulfate and evaporated to dryness. The title compound was obtained as pale yellow oil (quantitative) and it was used in the next step without any further purification.

1H-NMR (400 MHz), δ (ppm, DMSO-d₆): 8.04 (dd, J=8.47, 2.50 Hz, 1H) 7.95 (dd, J=8.66, 5.37 Hz, 1H) 7.71 (ddd, J=8.66, 8.17, 2.56 Hz, 1H) 1.51 (s, 9H).

Operating in an analogous way, the following compound was obtained:

tert-butyl 5-fluoro-2-nitrobenzoate

1H-NMR (400 MHz), δ (ppm, DMSO-d₆):1.53 (s, 9H) 7.66 (m, 1H) 7.73 (dd, J=8.29, 2.80 Hz, 1H) 8.18 (dd, J=9.15, 4.76 Hz, 1H)

Preparation of 4-(4-methyl-piperazin-1-yl)-2-nitro-benzoic acid tert-butyl ester A solution of 4-fluoro-2-nitro-benzoic acid tert-butyl ester (13 g, 54 mmol) and N-methylpiperazine (17 mL) was stirred at room temperature for 6 hours. The reaction mixture was then diluted with water (800 mL) and maintained under magnetic stirring for 20 hours. The resulting solid was filtered, washed thoroughly with water and dried under vacuum at 40° C. The title compound was obtained as yellow solid (16.4 g, 94% yield) and it was used in the next step without any further purification.

1H-NMR (400 MHz), δ (ppm, DMSO-$d_6$): 7.69 (d, J=8.90 Hz, 1H) 7.29 (d, J=2.56 Hz, 1H), 7.15 (dd, J1=8.90 Hz, J2=2.56 Hz, 1H), 3.37 (m, 4H), 2.44 (m, 4H), 1.46 (s, 9H).

Operating in an analogous way, the following compounds were obtained:

tert-butyl 5-(4-methylpiperazin-1-yl)-2-nitrobenzoate

1H-NMR (400 MHz), δ (ppm, DMSO-$d_6$):1.52 (s, 9H) 2.22 (s, 3H) 2.39-2.44 (m, 4H) 6.96 (d, J=2.93 Hz, 1H) 7.05 (dd, J=9.46, 2.87 Hz, 1H) 7.96 (d, J=9.40 Hz, 1H)

4-[(3-Dimethylamino-propyl)-methyl-amino]-2-nitro-benzoic acid tert-butyl ester

1H-NMR (400 MHz), δ (ppm, DMSO-$d_6$): 7.67 (d, J=9.0 Hz, 1H), 7.02 (d, J=2.6 Hz, 1H), 6.90 (dd, J1=9.0 Hz, J2=2.6 Hz, 1H), 3.46 (m, 2H), 3.00 (s, 3H), 2.22 (m, 2H), 2.14 (s, 6H), 1.65 (m, 2H), 1.45 (s, 9H).

tert-butyl 4-{[3-(dimethylamino)propyl](methyl)amino}benzoate

1H-NMR (400 MHz), δ (ppm, DMSO-$d_6$): 1.51 (s, 9H) 1.65 (quin, J=7.04 Hz, 2H) 2.15 (s, 6H) 2.24 (t, J=6.77 Hz, 2H) 2.96 (s, 3H) 3.42 (t, J=7.19 Hz, 2H) 6.64-6.75 (m, 2H) 7.65-7.74 (m, 2H)

Preparation of 2-amino-4-(4-methyl-piperazin-1-yl)-benzoic acid tert-butyl ester A mixture of 4-(4-methyl-piperazin-1-yl)-2-nitro-benzoic acid tert-butyl ester (13.3 g, 41.5 mmol) cyclohexene (45 mL), ethanol (300 mL) and 10% Pd/C (0.4 g) was stirred at 80° C. for 7 hours. More 10% Pd/C was added (0.9 g) and the mixture stirred at 80° C. for additional 4 hours. The reaction mixture was filtered over a celite pad washing thoroughly with ethanol and the filtrate was evaporated to dryness affording the title compound as a pale yellow solid (11.5 g, 95% yield).

1H-NMR (400 MHz), δ (ppm, DMSO-$d_6$): 7.47 (d, J=9.0Hz, 1H), 6.40 (bs, 2H), 6.18 (dd, J1=9.0 Hz, 1H), 6.11 (d, J=2.4 Hz, 1H), 3.16 (m, 4H), 2.41 (m, 4H), 2.21 (s, 3H), 1.49 (s, 9H).

Operating in an analogous way, the following compounds were obtained:

tert-butyl 2-amino-5-(4-methylpiperazin-1-yl)benzoate

1H-NMR (400 MHz), δ (ppm, DMSO-$d_6$):1.53 (s, 9H) 2.20 (s, 3H) 2.40-2.46 (m, 4H) 2.84-2.95 (m, 4H) 6.13 (s, 2H) 6.68 (d, J=9.03 Hz, 1H) 7.04 (dd, J=8.97, 2.99 Hz, 1H) 7.15 (d, J=2.93 Hz, 1H)

2-Amino-4-[(3-dimethylamino-propyl)-methyl-amino]-benzoic acid tert-butyl ester

1H-NMR (400 MHz), δ (ppm, DMSO-$d_6$): 7.45 (d, J=9.0 Hz, 1H), 6.36 (bs, 2H), 5.99 (dd, J1=9.0 Hz, J2=2.6 Hz, 1H), 5.86 (d, J=2.6 Hz, 1H), 3.31 (m, 2H), 2.87 (s, 3H), 2.22 (m, 2H), 2.15 (s, 6H), 1.62 (m, 2H), 1.48 (s, 9H).

Preparation of 4-(4-methyl-piperazin-1-yl)-2-(tetrahydro-pyran-4-ylamino)-benzoic acid tert-butyl ester To a solution of 2-amino-4-(4-methyl-piperazin-1-yl)-benzoic acid tert-butyl ester (11.5 g, 39.5 mmol) in dichloromethane (340 mL) were added tetrahydro-pyran-4-one (4.5 mL, 49.3 mmol), trifluoroacetic acid (8.2 mL) and tetramethylammonium triacetoxyborohydride (15.57 g, 59.2 mmol). The mixture was stirred at room temperature for 2 hours then washed with 0.5N hydrochloric acid, with 0.5N NaOH and with a saturated solution of NaHCO$_3$. The organic layer was dried over sodium sulfate and evaporated to dryness affording the title compound as a pale yellow solid (13.3 g, 90% yield).

1H-NMR (400 MHz), δ (ppm, DMSO-$d_6$): 7.72 (d, J=7.7 Hz, 1H), 7.58 (d, J=9.1 Hz, 1H), 6.20 (dd, J1=9.1 Hz, J2=2.2 Hz, 1H), 6.08 (d, J=2.2 Hz, 1H), 3.85 (m, 2H), 3.70 (m, 1H), 3.50 (m, 2H), 2.47 (m, 4H), 2.26 (bt, 3H), 1.96 (m, 2H), 1.51 (s, 9H), 1.39 (m, 2H).

Operating in an analogous way, the following compounds were obtained:

4-[(3-Dimethylamino-propyl)-methyl-amino]-2-(tetrahydro-pyran-4-ylamino)-benzoic acid tert-butyl ester 1H-NMR (400 MHz), δ (ppm, DMSO-$d_6$): 7.70 (bd, J=7.4 Hz, 1H), 7.54 (d, J=9.0 Hz, 1H), 5.99 (dd, J1=9.0 Hz, J2=2.3 Hz, 1H), 5.79 (d, J=2.3 Hz, 1H), 3.86 (m, 2H), 3.62 (m, 1H), 3.47 (m, 2H), 3.36 (m, 2H) (s, 3H), 2.28 (m, 2H), 2.18 (bs, 6H), 1.97 (m, 2H), 1.64 (m, 2H), 1.49 (s, 9H), 1.39 (m, 2H).

tert-butyl 2-(cyclohexylamino)-4-(4-methylpiperazin-1-yl)benzoate

ESI(+) MS: m/z 374 (MH$^+$).

tert-butyl 2-[(1,3-dimethoxypropan-2-yl)amino]-4-(4-methylpiperazin-1-yl)benzoate ESI(+) MS: m/z 394 (MH$^+$).

tert-butyl 2-(benzylamino)-4-(4-methylpiperazin-1-yl)benzoate

ESI(+) MS: m/z 382 (MH$^+$).

tert-butyl 5-(4-methylpiperazin-1-yl)-2-(tetrahydro-2H-pyran-4-ylamino)benzoate

ESI(+) MS: m/z 376 (MH$^+$).

Preparation of 4-(4-methyl-piperazin-1-yl)-2-[(tetrahydro-pyran-4-yl)-(2,2,2-trifluoro-acetyl)-amino]-benzoic acid tert-butyl ester To a solution of 4-(4-methyl-piperazin-1-yl)-2-(tetrahydro-pyran-4-ylamino)-benzoic acid tert-butyl ester (13.3 g, 35.4 mmol) in dry dichloromethane (350 mL), under argon, at 0° C., were added triethylamine (7.5 mL, 53.1 mmol) and trifluoroacetic anhydride (6.5 mL, 46.1 mmol). The mixture was stirred at 0° C. for 20 minutes, then water (350 mL) was dropped. The phases were separated and the organic phase washed with brine, dried over sodium sulfate and evaporated to dryness. The crude residue was purified by chromatography on silica gel using dichloromethane/ethanol 95:5 as the eluant, affording 12.1 g of the title compound as a pale yellow solid (73% yield).

1H-NMR (400 MHz), δ (ppm, DMSO-$d_6$): 7.83 (d, J=9.0 Hz, 1H), 7.06 (dd, J1=9.0 Hz, J2=2.5 Hz, 1H), 6.82 (J=2.5 Hz, 1H), 4.48 (m, 1H), 3.85 (m, 2H), 3.5-3.3 (m, 6H), 2.49 (m, 4H), 2.26 (bs, 3H), 2.0 (m, 1H), 1.59 (m, 1H) 1.51 (m, 1H), 1.46 (s, 9H), 1.03 (m, 1H).

Operating in an analogous way, the following compounds were obtained:

4-[(3-Dimethylamino-propyl)-methyl-amino]-2-[(tetrahydro-pyran-4-yl)-(2,2,2-trifluoro-acetyl)-amino]-benzoic acid tert-butyl ester 1H-NMR (400 MHz), δ (ppm, DMSO-$d_6$): 7.79 (d, J=9.1 Hz, 1H), 6.79 (dd, J1=9.1 Hz, J2=2.6 Hz, 1H), 6.52 (d, J=2.6 Hz, 1H), 4.48 (m, 1H), 3.87 (m, 1H), 3.79 (m, 1H), 3.51-3.32 (m, 4H), 2.98 (s, 3H), 2.22 (m, 2H) 2.12 (s, 6H) 1.99 (m, 1H), 1.70-1.46 (m, 4H), 1.44 (s, 9H), 1.03 (m, 1H).

tert-butyl 2-[cyclohexyl(trifluoroacetyl)amino]-4-(4-methylpiperazin-1-yl)benzoate ESI(+) MS: m/z 470 (MH$^+$).

tert-butyl 2-[(1,3-dimethoxypropan-2-yl)(trifluoroacetyl)amino]-4-(4-methylpiperazin-1-yl)benzoate ESI(+) MS: m/z 490 (MH$^+$).

tert-butyl 2-[benzyl(trifluoroacetyl)amino]-4-(4-methylpiperazin-1-yl)benzoate

ESI(+) MS: m/z 478 (MH$^+$).

tert-butyl 5-(4-methylpiperazin-1-yl)-2-[tetrahydro-2H-pyran-4-yl(trifluoroacetyl)amino]benzoate 1H-NMR (400 MHz), δ (ppm, DMSO-$d_6$): 0.91-1.03 (m, 1H) 1.43-1.53 (m, 1H) 1.48 (s, 9H) 1.90-1.97 (m, 1H) 2.24 (s, 3H) 2.43-2.49 (m, 4H) 3.26 (dd, J=5.73, 4.27 Hz, 4H) 3.33-3.46 (m, 2H) 3.80 (m, 2H) 3.80 (dd, J=11.16, 3.96 Hz, 1H) 3.83-3.90 (m, 1H) 4.43-4.53 (m, 1H) 7.16-7.19 (m, 1H) 7.20-7.23 (m, 1H) 7.39 (d, J=2.07 Hz, 1H)

Preparation of 4-(4-methyl-piperazin-1-yl)-2-[(tetrahydro-pyran-4-yl)-(2,2,2-trifluoro-acetyl)-amino]-benzoic acid trifluoroacetate A mixture of 4-(4-methyl-piperazin-1-yl)-2-[(tetrahydro-pyran-4-yl)-(2,2,2-trifluoro-acetyl)-amino]-benzoic acid tert-butyl ester (12.1 g, 25.7 mmol), trifluoroacetic acid (48.5 mL) and dichloromethane (195 mL) was stirred at room temperature for 2 hours. The volatiles were then evaporated, the residue taken up with diethylether and evaporated again. The procedure was repeated for 5 times, then the solid was triturated with diethylether, filtered and dried in oven at 40° C. affording the title compound as a pale brown solid (13.4 g).

1H-NMR (400 MHz), δ (ppm, DMSO-$d_6$): 12.78 (bs, 1H), 9.74 (bs, 1H), 7.93 (d, J=8.8 Hz, 1H) 7.13 (dd, J1=8.8 Hz, J2=2.5 Hz, 1H), 6.98 (d, J=2.5 Hz, 1H), 4.49 (m, 1H), 4.11 (m, 2H), 3.84 (m, 2H), 3.6-3.0 (m, 8H), 2.89 (s, 3H), 1.98 (m, 1H), 1.59 (m, 1H), 1.53 (m, 1H), 1.08 (m, 1H).

Operating in an analogous way, the following compounds were obtained:

4-[(3-Dimethylamino-propyl)-methyl-amino]-2-[(tetrahydro-pyran-4-yl)-(2,2,2-trifluoro-acetyl)-amino]-benzoic acid trifluoroacetate ESI(+) MS: m/z 432 (MH$^+$).

2-[cyclohexyl(trifluoroacetyl)amino]-4-(4-methylpiperazin-1-yl)benzoic acid hydrochloride ESI(+) MS: m/z 414 (MH$^+$).

2-[(1,3-dimethoxypropan-2-yl)(trifluoroacetyl)amino]-4-(4-methylpiperazin-1-yl)benzoic acid hydrochloride ESI(+) MS: m/z 434 (MH$^+$).

2-[benzyl(trifluoroacetyl)amino]-4-(4-methylpiperazin-1-yl)benzoic acid hydrochloride ESI(+) MS: m/z 422 (MH$^+$).

5-(4-methylpiperazin-1-yl)-2-[tetrahydro-2H-pyran-4-yl(trifluoroacetyl)amino]benzoic acid trifluoroacetate ESI(+) MS: m/z 416 (MH$^+$).

4-{[3-(dimethylamino)propyl](methyl)amino}benzoic acid hydrochloride

1H-NMR (400 MHz), δ (ppm, DMSO-$d_6$): 1.86-1.96 (m, 2H) 2.75 (s, 3H) 2.76 (s, 3H) 2.99 (s, 3H) 3.03-3.13 (m, 2H) 3.47 (br. s., 2H) 6.73-6.78 (m, 2H) 7.73-7.78 (m, 2H) 9.92 (br. s., 1H)

Preparation 4

Preparation of 2,4-difluoro-benzoic acid tert-butyl ester

To a solution of 2,4-difluorobenzoic acid (5 g, 31.62 mmol) in a mixture of dichloromethane (100 mL) and t-BuOH (50 mL) were added (Boc)$_2$O (13.8 g, 63.24 mmol) and N,N-dimethylaminopyridine (1.16 g, 9.49 mmol). The solution was stirred at room temperature for 24 hours then diluted with dichloromethane and washed twice with 1N HCl, NaHCO$_3$ satured solution, water (3 times) and brine. The organic phase was dried over sodium sulfate, filtered and evaporated to give the title compound (5.70 g, 84%) as yellowish oil.

1H-NMR (400 MHz), δ (ppm, DMSO-$d_6$): 7.91 (m, 1H), 7.36 (m, 1H), 7.20 (m, 1H), 1.53 (s, 9H).

Preparation of 4-fluoro-2-((R)-2-methoxy-1-methyl-ethylamino)-benzoic acid tert-butyl ester A mixture of 2,4-difluoro-benzoic acid tert-butyl ester (30 g, 140.05 mmol) and (R)-2-methoxy-1-methyl-ethylamine (100 mL) was stirred at 65° C. for 2 days. A satured solution of NaHCO$_3$ was added and the mixture was extracted with dichloromethane (3 times). The organic phase was washed twice with water then with brine, dried over sodium sulfate filtered and evaporated to dryness to obtain a crude, which was purified by column chromatography on silica gel (exane/ethyl acetate 9:1). The title compound (33.38 g, 84%) was obtained as oil.

1H-NMR (400 MHz), δ (ppm, DMSO-$d_6$): 7.87 (d, J=7.80 Hz, 1H), 7.80 (t, J=7.19 Hz, 1H), 6.60 (dd,m J1=13.05 Hz, J2=2.44 Hz, 1H), 6.36 (m, 1H), 3.80 (m, 1H), 3.40 (d, J=4.76 Hz, 2H), 3.30 (s, 9H), 1.17 (d, J=6.58 Hz, 3H).

Operating in a way analogous to that described above, the following compounds were obtained:

4-Fluoro-2-(2-methoxy-ethylamino)-benzoic acid tert-butyl ester

1H-NMR (400 MHz), δ (ppm, DMSO-$d_6$): 7.89 (t, J=5.00 Hz, 1H), 7.80 (t, J=7.07 Hz, 1H), 6.56 (dd, J1=12.80 Hz, J2=2.56 Hz, 1H), 6.37 (m, 1H), 3.55 (t, J=5.37 Hz, 2H), 3.33 (m, 2H), 3.29 (s, 3H), 1.53 (s, 9H).

tert-butyl 4-fluoro-2-[(3-methoxypropyl)amino]benzoate

1H-NMR (400 MHz), δ (ppm, DMSO-$d_6$): 1.51-1.53 (m, 9H) 1.76-1.85 (m, 2H) 2.18-3.23 (m, 2H) 3.25 (s, 3H) 3.38-3.44 (m, 2H) 6.32-6.39 (m, 1H) 6.49 (dd, J=12.80, 2.44 Hz, 1H) 7.79 (dd, J=8.90, 7.07 Hz, 1H) 7.88 (br. s., 1H)

tert-butyl 4-fluoro-2-[(2-fluoroethyl)amino]benzoate

1H-NMR (400 MHz), δ (ppm, DMSO-$d_6$): 1.54 (s, 9H) 3.50 (dd, J=27.00, 5.00 Hz, 2H) 4.63 (dt, J=47.56, 4.88 Hz, 2H) 6.41 (td, J=8.57, 2.50 Hz, 1H) 6.62 (dd, J=12.62, 2.38 Hz, 1H) 7.82 (dd, J=8.90, 7.07 Hz, 1) 8.05 (t, J=4.82 Hz, 1H)

tert-butyl 4-fluoro-2-[(1-methoxy-2-methylpropan-2-yl)amino]benzoate

1H-NMR (400 MHz), δ (ppm, DMSO-$d_6$): 1.34 (s, 6H) 1.53 (s, 9H) 3.33 (br. s., 3H) 3.40 (s, 2H) 6.31-6.39 (m, 1H) 6.67 (dd, J=13.29, 2.44 Hz, 1H) 7.82 (d, J=8.84, 7.38 Hz, 1H) 8.22 (s, 1H)

Preparation of 4-fluoro-2-[((R)-2-methoxy-1-methyl-ethyl)-(2,2,2-trifluoro-acetyl)-amino]-benzoic acid tert-butyl ester A solution of 4-fluoro-2-((R)-2-methoxy-1-methyl-ethylamino)-benzoic acid tert-butyl ester (1.54 g, 5.44 mmol) in dichloromethane (30 mL) was cooled to 0°-5° C. Triethylamine (1.11 mL, 8.16 mmol) and trifluoroacetic anhydride (1.15 mL, 8.16 mmol) were added. After 3 hours at 0°-5° C. the mixture was washed with NaHCO$_3$ satured solution, water and brine. The organic layer was dried over sodium sulfate, filtered and evaporated to give the title compound as yellowish oil (2 g, 99%).

1H-NMR (400 MHz), δ (ppm, DMSO-$d_6$): (mixture of tautomers) 8.07 (m, 1H), 7.53 (m, 1H), 7.29 (dd, J1=9.39 Hz, J2=2.68 Hz, 1H), 4.83 (m, 1H), 3.44 (m, 1H), 3.30 (s, 3H), 1.49 (s, 9H), 0.86 (d, 3H).

Operating in a way analogous to that described above, the following compounds were obtained:

4-Fluoro-2-[(2-methoxy-ethyl)-(2,2,2-trifluoro-acetyl)-amino]-benzoic acid tert-butyl ester 1H-NMR (400 MHz), δ (ppm, DMSO-$d_6$): 8.07 (m, 1H), 7.50 (m, 1H), 7.41 (dd, J1=9.39 Hz, J2=2.56 Hz, 1H), 4.28 (m, 1H), 3.55 (m, 1H), 3.46 (m, 1H), 3.38 (m, 1H), 3.18 (s, 3H), 1.49 (s, 9H).

tert-butyl 4-fluoro-2-[(3-methoxypropyl)(trifluoroacetyl)amino]benzoate

1H-NMR (400 MHz), δ (ppm, DMSO-$d_6$): 1.48 (s, 9H) 1.68-1.83 (m, 2H) 3.18 (s, 3H) 3.21-3.29 (m, 1H) 3.33-3.38 (m, 2H) 4.06-4.18 (m, 1H) 7.46-7.52 (m, 1H) 7.56 (dd, J=9.27, 2.68 Hz, 1H) 8.06 (dd, J=8.84, 6.40 Hz, 1H)

tert-butyl 4-fluoro-2-[(2-fluoroethyl)(trifluoroacetyl)amino]benzoate

1H-NMR (400 MHz), δ (ppm, DMSO-$d_6$): 1.50 (s, 9H) 3.54-3.74 (m, 1H) 4.26-4.80 (m, 2H) 7.47-7.55 (m, 2H) 8.08 (dd, J=9.27, 6.46 Hz, 1H)

tert-butyl 4-fluoro-2-[(1-methoxy-2-methylpropan-2-yl)(trifluoroacetyl)amino]benzoate 1H-NMR (400 MHz), δ (ppm, DMSO-$d_6$): 1.09 (s, 3H) 1.47 (s, 3H) 1.52 (s, 9H) 3.17 (s, 3H) 3.19 (d, J=9.75 Hz, 1H) 3.80 (d, J=9.63 Hz, 1H) 7.36 (dd, J=9.45, 2.62 Hz, 1H) 7.47 (td, J=8.41, 2.68 Hz, 1H) 7.93 (dd, J=8.78, 6.46 Hz, 1H)

Preparation of 2[((R)-2-methoxy-1-methyl-ethyl)-(2,2,2-trifluoro-acetyl)-amino]-4-(4-methyl-piperazin-1-yl)-benzoic acid tert-butyl ester A solution of 4-fluoro-2-[((R)-2-methoxy-1-methyl-ethyl)-(2,2,2-trifluoro-acetyl)-amino]-benzoic acid tert-butyl ester (2 g, 5.28 mmol) and N-methylpiperazine (5.86 mL, 52.8 mmol) in tetrahydrofuran (20 mL) was stirred at 60° C. for 7 days. The solution was then evaporated, NaHCO$_3$ satured solution was added and the mixture extracted with dichloromethane (3 times). The organic layer was washed with water, brine, dried over sodium sulfate filtered and evaporated to obtain a crude, which was purified by column chromatography on silica gel (dichloromethane-methanol 93:7). The title compound (2.04 g, 84%) was obtained as yellowish solid.

1H-NMR (400 MHz), δ (ppm, DMSO-$d_6$): (mixture of tautomers) 7.81 (d, J=9.15 Hz, 1H), 7.06 (dd, J1=9.15 Hz, J2=2.56 Hz, 1H), 6.79 (d, J=2.56 Hz, 1H), 4.80 (m, 1H), 3.39 (m, 2H), 3.34-3.28 (m, 7H), 2.55 (m, 4H), 2.29 (bs, 3H), 1.46 (s, 9H), 0.83 (d, 3H).

Operating in a way analogous to that described above, the following compounds were obtained:

2-[(2-Methoxy-ethyl)-(2,2,2-trifluoro-acetyl)-amino]-4-(4-methyl-piperazin-1-yl)-benzoic acid tert-butyl ester 1H-NMR (400 MHz), δ (ppm, DMSO-$d_6$): (mixture of tautomers) 7.83 (d, J=9.02 Hz, 1H), 7.05 (dd, J1=9.02 Hz, J2=2.68 Hz, 1H), 6.86 (d, J=2.68 Hz, 1H), 4.31 (m, 1H), 3.55 (m, 1H), 3.40 (m, 1H) 3.32 (m, 4H), 3.25 (m, 1H), 3.21 (s, 1H), 2.44 (t, J=5.12 Hz, 4H), 2.22 (bs, 3H), 1.46 (s, 9H).

tert-butyl 2-[(3-methoxypropyl)(trifluoroacetyl)amino]-4-(4-methylpiperazin-1-yl)benzoate 1H-NMR (400 MHz), δ (ppm, DMSO-$d_6$): 1.45 (s, 9H) 1.68-1.84 (m, 2H) 2.26 (br. s., 3H) 2.44-2.60 (m, 4H) 3.12-3.23 (m, 1H) 3.18 (s, 3H) 3.25-3.48 (m, 6H) 4.08 (d, J=22.92 Hz, 1H) 6.92 (d, J=2.19 Hz, 1H) 7.02 (dd, J=9.02, 2.44 Hz, 1H) 7.81 (d, J=9.02 Hz, 1H)

tert-butyl 2-[(2-fluoroethyl)(trifluoroacetyl)amino]-
4-(4-methylpiperazin-1-yl)benzoate 1H-NMR (400 MHz), δ (ppm, DMSO-d$_6$): 1.46 (s, 9H)
2.22 (s, 3H) 2.43 (t, J=4.76 Hz, 4H) 3.25-3.31 (m, 4H) 3.41-
3.59 (m, 1H) 4.27-4.46 (m, 1H) 4.46-4.78 (m, 2H) 6.90 (d,
J=2.07 Hz, 1H) 7.05 (dd, J=9.02, 2.68 Hz, 1H) 7.83 (d, J=9.02
Hz, 1H)

tert-butyl 2-[(1-methoxy-2-methylpropan-2-yl)(trif-
luoroacetyl)amino]-4-(4-methylpiperazin-1-yl)ben-
zoate 1H-NMR (400 MHz), δ (ppm, DMSO-d$_6$): 1.04 (s, 3H)
1.45 (s, 3H) 1.49 (s, 9H) 2.22 (s, 3H) 2.44 (t, J=4.94 Hz, 4H)
3.20 (d, J=9.51 Hz, 1H) 3.23 (s, 3H) 3.25-3.30 (m, 4H) 3.93
(d, J=9.51 Hz, 1H) 6.89 (d, J=2.32 Hz, 1H) 7.00 (dd, J=8.96,
2.62 Hz, 1H) 7.70 (d, J=8.90 Hz, 1H)

Preparation of 2-[((R)-2-methoxy-1-methyl-ethyl)-
(2,2,2-trifluoro-acetyl)-amino]-4-(4-methyl-piper-
azin-1-yl)-benzoic acid trifluoroacetate To a solution of 2-[((R)-2-methoxy-1-methyl-ethyl)-(2,2,
2-trifluoro-acetyl)-amino]-4-(4-methyl-piperazin-1-yl)-ben-
zoic acid tert-butyl ester (2.03 g, 4.42 mmol) in dichlo-
romethane (15 mL) trifluoroacetic acid (3.4 mL, 44.2 mmol)
was added. The mixture was stirred at room temperature for
15 hours then the solution was evaporated to dryness afford-
ing the title compound as oil that was used for the next step
without any further purification.

1H-NMR (400 MHz), δ (ppm, DMSO-d$_6$): (mixture of
tautomers) 12.10 (bs, 1H), 9.74 (bs, 1H), 7.90 (d, J=8.90 Hz,
1H), 7.15 (dd, J1=8.90 Hz, J2=2.56 Hz, 1H), 6.89 (d, J=2.56
Hz, 1H), 4.76 (m, 1H), 4.03 (t, 2H), 3.55 (m, 2H), 3.37 (m,
2H), 3.30 (s, 3H), 3.18 (m, 2H), 2.88 (bs, 3H), 0.85 (d, 3H).

Operating in a way analogous to that described above, the
following compounds were obtained:

2-[(2-Methoxy-ethyl)-(2,2,2-trifluoro-acetyl)-
amino]-4-(4-methyl-piperazin-1-yl)-benzoic acid
trifluoroacetate 1H-NMR (400 MHz), δ (ppm, DMSO-d$_6$): (mixture of
tautomers) 12.76 (bs, 1H), 9.73 (bs, 1H), 7.91 (d, J=8.78 Hz,
1H), 7.10 (dd, J1=8.78 Hz, J2=2.68 Hz, 1H), 7.01 (d, J=2.68
Hz, 1H), 4.15 (m, 1H), 4.04 (m, 2H), 3.54 (m, 2H), 3.42 (m,
2H), 3.38 (m, 2H), 3.33 (m, 2H), 3.19 (s, 3H), 3.14 (m, 2H),
2.86 (bs, 3H).

2-[(3-methoxypropyl)(trifluoroacetyl)amino]-4-(4-
methylpiperazin-1-yl)benzoic acid hydrochloride 1H-NMR (400 MHz), δ (ppm, DMSO-d$_6$): 1.70-1.81 (m,
2H) 2.84 (d, J=2.93 Hz, 3H) 3.06-3.40 (m, 7H) 3.19 (s, 3H)
3.52 (d, J=10.36 Hz, 2H) 3.96-4.06 (m, 1H) 4.09 (br. s., 2H)
7.07 (d, J=2.56 Hz, 1H) 7.10 (dd, J=8.90, 2.68 Hz, 1H) 7.93
(d, J=8.78 Hz, 1H) 10.27 (br. s., 1H) 12.76 (br. s., 1H)

2-[(2-fluoroethyl)(trifluoroacetyl)amino]-4-(4-meth-
ylpiperazin-1-yl)benzoic acid hydrochloride 1H-NMR (400 MHz), δ (ppm, DMSO-d$_6$): 2.84 (br. s., 3H)
3.04-3.30 (m, 4H) 3.47-3.56 (m, 2H) 3.54-3.67 (m, 1H) 4.06
(d, 2H) 4.18-4.40 (m, 1H) 4.46-4.79 (m, 2H) 7.07 (d, J=2.19
Hz, 1H) 7.12 (dd, J=8.96, 2.62 Hz, 1H) 7.91-7.97 (m, 1H)
10.33 (br. s., 1H) 12.83 (br. s., 1H)

2-[(1-methoxy-2-methylpropan-2-yl)(trifluoroacetyl)
amino]-4-(4-methylpiperazin-1-yl)benzoic acid
hydrochloride 1H-NMR (400 MHz), δ (ppm, DMSO-d$_6$): 1.07 (s, 3H)
1.43 (s, 3H) 2.84 (s, 3H) 3.10-3.38 (m, 5H) 3.25 (s, 3H)
3.47-3.57 (m, 2H) 3.92 (d, J=9.51 Hz, 1H) 3.95-4.02 (m, 2H)
7.00 (d, J=2.44 Hz, 1H) 7.10 (dd, J=8.84, 2.50 Hz, 1H) 7.84
(d, J=8.78 Hz, 1H) 10.25 (br. s., 1H) 12.77 (br. s., 1H)

Preparation 5

Preparation of ethyl 4-{[2-(tert-butoxycarbonyl)-5-
(4-methylpiperazin-1-yl)phenyl]amino}piperidine-1-
carboxylate tert-Butyl 2-amino-4-(4-methylpiperazin-1-yl)benzoate
(1.5 g, 5.15 mmol) was dissolved in dry dioxane (25 mL)
under a nitrogen atmosphere. N-ethoxycarbonylpiperidone
(1.06 g, 0.932 mL, 6.18 mmol, 1.2 eq) was added, followed by
trifluoroacetic acid (1.03 mL, 13.39 mmol, 2.6 eq) and
sodium triacetoxyborohydride (1.72 g, 7.73 mmol, 1.5 eq).
The mixture was stirred at room temperature for 4 hours. A
saturated aqueous solution of NaHCO$_3$ was then added, the
mixture was concentrated under reduced pressure and
extracted with dichloromethane (3×40 mL). The combined
organic layers were washed with brine, dried over Na2SO4
and concentrated under reduced pressure. After purification
by chromatography over silica gel (DCM/EtOH 93:7) 2.187 g
of title compound were obtained as a white solid (95% yield).

1H-NMR (400 MHz), δ (ppm, DMSO-d$_6$): 1.19 (t, J=7.50
Hz, 3H) 1.24-1.34 (m, 2H) 1.50 (s, 9H) 1.89-2.00 (m, 2H)
2.22 (s, 3H) 2.39-2.45 (m, 4H) 3.03-3.16 (m, 2H) 3.20-3.29
(m, 4H) 3.80-3.90 (m, 2H) 4.05 (q, J=7.07 Hz, 2H) 6.07 (d,
J=2.07 Hz, 1H) 6.20 (dd, J=9.15, 2.19 Hz, 1H) 7.57 (d, J=9.02
Hz, 1H) 7.70 (d, J=7.93 Hz, 1H)

Preparation of ethyl 4-{[2-(tert-butoxycarbonyl)-5-
(4-methylpiperazin-1-yl)phenyl](trifluoroacetyl)
amino}piperidine-1-carboxylate Ethyl 4-{[2-(tert-butoxycarbonyl)-5-(4-methylpiperazin-
1-yl)phenyl]amino}piperidine-1-carboxylate (2.18 g, 4.88
mmol) was dissolved in dry dichloromethane (20 mL) under
nitrogen atmosphere and the solution was cooled to 0° C.
Triethylamine (1.02 mL, 7.32 mmol, 1.5 eq) was added, fol-
lowed by trifluoroacetic anhydride (0.827 mL, 5.856 mmol,
1.2 eq) and the mixture was stirred at 0° C. After 3 hours an
extra addition of triethylamine (0.815 mL, 5.86 mmol, 1.2 eq)
and trifluoroacetic anhydride (0.415 mL, 2.93 mmol, 0.6 eq)
was made and the mixture was allowed to warm to room
temperature overnight. The mixture was diluted with dichlo-
romethane and washed twice with saturated aqueous
NaHCO$_3$. The aqueous phase was back-extracted with
dichloromethane. The combined organic layers were dried
over Na$_2$SO$_4$ and concentrated under reduced pressure. The
crude product was purified by chromatography on silica gel
(DCM/EtOH 95:5) to give 2.15 g of title compound as a
yellow oil that becomes solid upon drying (81% yield).

1H-NMR (400 MHz), δ (ppm, DMSO-d$_6$): 0.77-0.93 (m,
1H) 1.13 (t, J=7.07 Hz, 3H) 1.34-1.44 (m, 1H) 1.46 (s, 9H)
1.56-1.63 (m, 1H) 2.01-2.10 (m, 1H) 2.22 (s, 3H) 2.40-2.44
(m, 4H) 2.78-2.97 (m, 2H) 3.27-3.36 (m, 4H) 3.91-4.06 (m, 2H) 3.94-4.01 (m, 2H) 4.37-4.47 (m, 1H) 6.78 (d, J=2.44 Hz, 1H) 7.04 (dd, J=9.02, 2.56 Hz, 1H) 7.81 (d, J=9.02 Hz, 1H)

Preparation of 2-{[(ethoxycarbonyl)piperidin-4-yl] (trifluoroacetyl)amino}-4-(4-methylpiperazin-1-yl) benzoic acid hydrochloride ethyl 4-{[2-(tert-butoxycarbonyl)-5-(4-methylpiperazin-1-yl)phenyl](trifluoroacetyl)amino}piperidine-1-carboxylate (2.15 g, 3.960 mmol) was dissolved in dry dichloromethane (8 mL) under nitrogen atmosphere. A 4 M solution of HCl in dioxane (9.9 mL, 39.6 mmol, 10 eq) was then added dropwise and the mixture was stirred at room temperature. After 5 hours 5 more equivalents of HCl were added and the reaction was stirred at room temperature overnight. The mixture was evaporated to dryness and stripped twice with DCM. It was then taken up with DCM/dioxane 1:3 and slurried for 1 hour. The solid was filtered, washed with ether and dried under vacuum at 50° C. for 1 hour. 1.78 g of title compound were obtained as a beige powder (86% yield).

1H-NMR (400 MHz), δ (ppm, DMSO-$d_6$): 0.83-0.98 (m, 1H) 1.13 (t, J=7.01 Hz, 3H) 1.34-1.47 (m, 1H) 1.63 (d, J=10.85 Hz, 1H) 2.04 (d, J=13.66 Hz, 1H) 2.84 (s, 3H) 2.88 (m, 2H) 3.16 (m, 4H) 3.52 (m, 2H) 3.94-4.02 (m, 2H) 4.05 (m, 4H) 4.34-4.48 (m, 1H) 6.96 (d, J=2.32 Hz, 1H) 7.11 (dd, J=8.90, 2.56 Hz, 1H) 7.91 (d, J=8.90 Hz, 1H) 10.26 (br. s., 1H) 12.79 (br. s., 1H)

Preparation 6

Preparation of methyl 2-methoxy-4-(4-methylpiperazin-1-yl)benzoate

Methyl 2-methoxy-4-fluoro-benzoate (1.6 gr, 9.7 mmol), $K_2CO_3$ (1.3 gr, 9.7 mmol) and N-methyl piperazine (1.3 mL, 11.7 mmol) were heated at 100° C. in DMSO (5 mL) for 20 hours. Reaction mixture was diluted with DCM and washed with water. Organic phase was dried over sodium sulfate and evaporated to dryness. Column chromatography purification on silica gel using dichloromethane/methanol 95:5 as the eluant, afforded 1.7 g (yield 66%) of the title compound.

1H-NMR (400 MHz), δ (ppm, DMSO-$d_6$): 2.25 (s, 3H) 2.45 (br. s., 4H) 3.26-3.34 (m, 4H) 3.70 (s, 3H) 3.80 (s, 3H) 6.49 (d, J=2.32 Hz, 1H) 6.53 (dd, J=8.84, 2.38 Hz, 1H) 7.61 (d, J=8.78 Hz, 1H)

Preparation of 2-methoxy-4-(4-methylpiperazin-1-yl)benzoic acid hydrochloride

Methyl 2-methoxy-4-(4-methylpiperazin-1-yl)benzoate (1.9 gr, 7.2 mmol) was heated at 40° C. in a mixture 2N NaOH (10 mL) and MeOH (10 mL) for 2 hours. MeOH was evaporated and the acqueous layer was acidified to pH=6 with 25% HCl and extracted with n-BuOH. Organic phase was dried over sodium sulfate and evaporated to dryness. affording 1.0 g (yield 61%) of the title compound.

1H-NMR (400 MHz), δ (ppm, DMSO-$d_6$): 2.82 (br. s., 3H) 2.99-3.31 (m, 4H) 3.47 (br. s., 2H) 3.83 (s, 3H) 4.04 (br. s., 2H) 6.61 (d, 1H) 6.59 (s, 1H) 7.66 (d, J=8.78 Hz, 1H) 10.49 (br. s., 1H) 11.91 (br. s., 1H)

Preparation 7

Preparation of methyl 4-fluoro-2-methylbenzoate

In a cylindrical quartz tube was placed 4-fluoro-2-methylbenzoic acid (1.5 g, 9.7 mmol) in MeOH (15 ml) and 2 drops of $H_2SO_4$ conc. were added. The tube was introduced into a Smith Creator® Personal chemistry microwave reactor. Microwave irradiation was carried out at 130° C. for 1 h until HPLC revealed the disappearance of the starting-material. The mixture was allowed to cool down and the solvent was removed under reduced pressure. The crude was diluted with DCM and washed with $NaHCO_3$ sat. The organic phase was dried over anhydrous $Na_2SO_4$ and concentration of the solution gave the final compound (1.3 g, 78%) as colourless oil.

1H-NMR (400 MHz), δ (ppm, DMSO-$d_6$): 7.91 (dd, J=6.2, 8.7 Hz, 1H), 7.22 (dd, J=2.6, 10.2 Hz, 1H), 7.15 (td, J=2.4, 8.4 Hz, 1H), 3.83 (s, 3H), 2.54 (s, 3H)

Preparation of methyl 2-methyl-4-(4-methylpiperazin-1-yl)benzoate

In a cylindrical quartz tube were placed 4-fluoro-2-methylbenzoic acid methyl ester (1.2 g, 7.14 mmol), N-methylpiperazine (0.95 ml, 8.5 mmol), $K_2CO_3$ (990 mg, 7.14 mmol) and DMSO (4 ml). The reaction was heated for 20 hours at 110° C. until HPLC revealed the disappearance of the starting-material. DCM (15 ml) was added and the solution was washed twice with water and the organic phase was dried over anhydrous $Na_2SO_4$. The crude was purified by flash chromatography (DCM/MeOH 95:5) affording the desired compound (670 mg, 38%).

1H-NMR (400 MHz), δ (ppm, DMSO-$d_6$): 7.72-7.79 (m, 1H), 6.75-6.84 (m, 2H), 3.75 (s, 3H), 3.29 (br. s., 4H), 2.44 (d, J=5.0 Hz, 4H), 2.24 (s, 3H).

Preparation of 2-methyl-4-(4-methylpiperazin-1-yl)benzoic acid

To a solution of 2-methyl-4-(4-methyl-piperazin-1-yl)-benzoic acid methyl ester (660 mg, 2.66 mmol) in MeOh (4 ml), 2M NaOH (4 ml, 8 mmol) was added. The reaction was heated for 3 hours at 40° C. until HPLC revealed the disappearance of the starting-material. The solvent was removed under reduced pressure and the solution was diluted with water and neutralized to pH 7 with aqueous 25% HCl. The precipitate was filtrated and washed with $Et_2O$ to afford the desired final compound as with solid (400 mg, 64%).

ESI(+) MS: m/z 235 (MH$^+$).

Preparation 8

Preparation of 1-[1-(tert-butoxycarbonyl)piperidin-4-yl]-1H-pyrazole-4-carboxylic acid A mixture of ethyl 1H-pyrazole-4-carboxylate (700 mg, 5 mmol) and NaH 60% (6 mmol) was stirred under nitrogen at 0° C. for 1 hour in dry DMF (15 mL). tert-Butyl 4-[(methylsulfonyl)oxy]piperidine-1-carboxylate (1.53 gr, 5.5 mmol) dissolved in 4 mL of dry DMF was added and the resulting solution was heated at 100° C. overnight. Reaction mixture was quenched with water and extracted (×3) with ethyl acetate. Collected organic phases were dried over $Na_2SO_4$, filtered and evaporated to dryness. Residue was dissolved in MeOH (20 mL) and water (5 mL) and KOH (1.12 gr, 20 mmol) was added. The resulting solution was stirred at room temperature 24 hours, then solvents removed under reduced pressure. The residue was taken-up with AcOEt and $KHSO_4$ 5% solution. Acqueous phase was extracted with EtOAc several times. Collected organic phases were dried with $Na_2SO_4$, filtered and evaporated to dryness affording 600 mg of the title compound.

1H-NMR (400 MHz), δ (ppm, DMSO-d$_6$): 1.42 (s, 9H) 1.73-1.87 (m, 2H) 1.96-2.03 (m, 2H) 2.82-2.99 (m, 2H) 4.04 (d, J=12.93 Hz, 2H) 4.34-4.47 (m, 1H) 7.81 (s, 1H) 8.29 (s, 1H) 12.26 (br. s., 1H)

Preparation of 1-(1-methyl-piperidin-4-yl)-1H-pyrazole-4-carboxylic acid

According to the previously reported procedure, before the basic hydrolysis (KOH/MeOH/water), 4-(4-ethoxycarbonyl-pyrazol-1-yl)-piperidine-1-carboxylic acid tert-butyl ester (776 mg, 2.4 mmol) was dissolved in DCM (24 mL) and treated with TFA (1.85 mL, 24 mmol) for 3 hours. The reaction was poured into saturated NaHCO$_3$ solution (100 mL), extracted with DCM (2×200 mL). The combined organic layers were dried over anhydrous sodium sulfate and evaporated to dryness to afford 550 mg of crude product that was dissolved in DCM (20 mL) and treated first with TEA (1.058 mL, 7.595 mmol), then with 37 wt. % in water formaldehyde solution (0.22 mL, 2.95 mmol) and finally with sodium triacetoxyborohydride (782 mg, 3.69 mmol) at room temperature, with stirring, under a nitrogen atmosphere. After 1 hour, DCM was added (20 mL) and the organic layer was washed with saturated NaHCO$_3$ solution (25 mL), dried over anhydrous sodium sulfate and evaporated to leave an oil that was employed in the basic hydrolysis step with no further purification affording title compound.

ESI(+) MS: m/z 210 (MH$^+$).

Preparation 9

Preparation of 3-[4-(tert-butoxycarbonyl)piperazin-1-yl]benzoic acid

To a solution of 1-Boc-4-[3-(ethoxycarbonyl)phenyl]piperazine (200 mg, 0.6 mmol) in EtOH (1 ml), 2M NaOH (1 ml, 2 mmol) was added. The reaction was heated for 2 hours at 40° C. until HPLC revealed the disappearance of the starting material. The solution was neutralized to pH 7 with aqueous 25% HCl. The precipitate was filtrated and washed with Et$_2$O to afford the desired final compound as beige solid (80 mg, 40%).

ESI(+) MS: m/z 307 (MH$^+$).

The invention claimed is:
1. A compound of formula (I)

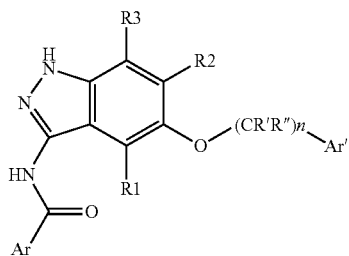

(I)

Ar is aryl or heteroaryl substituted with Ra and Rb, wherein
Ra is $NO_2$, $NH_2$, NH-G, N-(E)-G, O-G', $(CH_2)_n$-A or $CH_2$-Hal and
Rb is hydrogen, halogen, $NO_2$, $NH_2$, NH-G, NH—CO-L, O-E or E, wherein
Hal is halogen,
A is optionally substituted heterocyclyl,
E is straight or branched unsubstituted $C_1$-$C_6$ alkyl,
G is straight or branched substituted $C_1$-$C_6$ alkyl or an optionally substituted heterocyclyl,
G' is straight or branched $C_1$-$C_6$ alkyl substituted with $N(C_1$-$C_6$ alkyl$)_2$, or an optionally substituted heterocyclyl, and
L is optionally substituted heteroaryl;
Ar' is an optionally substituted aryl or heteroaryl;
R1, R2 and R3 are independently hydrogen, halogen, nitro, an optionally substituted straight or branched $C_1$-$C_6$ alkyl,
NR4R5 or OR6, wherein
R4 and R5 are independently hydrogen, alkenyl, alkynyl, R8R9N—$C_2$-$C_6$ alkyl, R8O—$C_2$-$C_6$ alkyl, an optionally further substituted straight or branched $C_1$-$C_6$ alkyl, $C_3$-$C_6$ cycloalkyl, heterocyclyl, aryl or heteroaryl, or R4 and R5, taken together with the nitrogen atom to which they are bonded, may form an optionally substituted heterocyclyl group;
R6 is hydrogen, alkenyl, alkynyl, COR7, SOR10, $SO_2$R10, R8R9N—$C_2$-$C_6$ alkyl, R8O—$C_2$-$C_6$ alkyl, an optionally further substituted straight or branched $C_1$-$C_6$ alkyl, $C_3$-$C_6$ cycloalkyl, heterocyclyl, aryl or heteroaryl;
R7 is hydrogen, alkenyl, alkynyl, NR4R5, OR6, SR6, R8R9N—$C_1$-$C_6$ alkyl, R8O—$C_1$-$C_6$ alkyl, an optionally further substituted straight or branched $C_1$-$C_6$ alkyl, $C_3$-$C_6$ cycloalkyl, heterocyclyl, aryl or heteroaryl, wherein R4, R5 and R6 are defined as above;
R8 and R9 are independently hydrogen, alkenyl, alkynyl, COR7, an optionally further substituted straight or branched $C_1$-$C_6$ alkyl, $C_3$-$C_6$ cycloalkyl, heterocyclyl, aryl or heteroaryl, or R8 and R9, taken together with the nitrogen atom to which they are bonded, may form an optionally substituted heterocyclyl group, wherein R7 is as defined above;
R10 is hydrogen, alkenyl, alkynyl, NR4R5, OR6, R8R9N—$C_1$-$C_6$ alkyl, R8O—$C_1$-$C_6$ alkyl, an optionally further substituted straight or branched $C_1$-$C_6$ alkyl, $C_3$-$C_6$ cycloalkyl, heterocyclyl, aryl or heteroaryl, wherein R4, R5, R6, R8 and R9 are as defined above;
R' and R'' are each independently hydrogen or an optionally substituted straight or branched $C_1$-$C_6$ alkyl;
n is 0 or 1, and
pharmaceutically acceptable salt thereof.

2. A compound of formula (I) as defined in claim 1 wherein:
R' and R'' are each independently hydrogen or $C_1$-$C_3$ alkyl, and
R1, R2 and R3 are independently hydrogen, halogen or hydroxy.

3. A compound of formula (I) as defined in claim 1 wherein:
R' and R'' are each independently hydrogen or methyl, and R1, R2 and R3 are hydrogen.

4. A compound of formula (I) as defined in claim 1, wherein Ar is a group of formula:

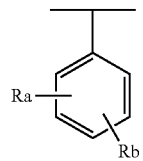

wherein Ra is $(CH_2)_n$-A or O-G', wherein A, G' and n are as defined in claim 1, and
Rb is as defined in claim 1.

5. A compound of formula (I) as defined in claim 1, wherein Ar is a group of formula:

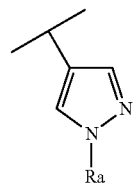

wherein Ra is $(CH_2)_n$-A, wherein A and n are as defined in claim 1.

6. A compound or a pharmaceutically acceptable salt thereof which is selected from the group consisting of:
N-(5-benzyloxy-1H-indazol-3-yl)-4-(4-methyl-piperazin-1-yl)-benzamide,
N-[5-(3-fluoro-benzyloxy)-1H-indazol-3-yl]-4-(4-methyl-piperazin-1-yl)-benzamide,
N-(5-benzyloxy-1H-indazol-3-yl)-2-(2-methoxy-ethylamino)-4-(4-methyl-piperazin-1-yl)-benzamide,
N-[5-(2-chloro-3,6-difluoro-benzyloxy)-1H-indazol-3-yl]-4-(4-methyl-piperazin-1-yl)-benzamide,
N-[5-(3,5-difluoro-benzyloxy)-1H-indazol-3-yl]-2-(2-methoxy-ethylamino)-4-(4-methyl-piperazin-1-yl)-benzamide, N-(5-benzyloxy-1H-indazol-3-yl)-4-(4-methyl-piperazin-1-yl)-2-(tetrahydro-pyran-4-ylamino)-benzamide,
N-[5-(3-fluoro-benzyloxy)-1H-indazol-3-yl]-4-(4-methyl-piperazin-1-yl)-2-(tetrahydro-pyran-4-ylamino)-benzamide,
N-[5-(3,5-difluoro-benzyloxy)-1H-indazol-3-yl]-4-(4-methyl-piperazin-1-yl)-2-(tetrahydro-pyran-4-ylamino)-benzamide,
N-(5-benzyloxy-1H-indazol-3-yl)-5-(4-methyl-piperazin-1-yl)-2-(tetrahydro-pyran-4-ylamino)-benzamide,
N-5-[1-(3,5-difluoro-phenyl)-ethoxy]-1H-indazol-3-yl-4-(4-methyl-piperazin-1-yl)-2-(tetrahydro-pyran-4-ylamino)-benzamide,
N-[5-(2,5-difluoro-benzyloxy)-1H-indazol-3-yl]-4-(4-methyl-piperazin-1-yl)-2-(tetrahydro-pyran-4-ylamino)-benzamide,
N-[5-(2,3-difluoro-benzyloxy)-1H-indazol-3-yl]-4-(4-methyl-piperazin-1-yl)-2-(tetrahydro-pyran-4-ylamino)-benzamide,
N-[5-(3,4-difluoro-benzyloxy)-1H-indazol-3-yl]-4-(4-methyl-piperazin-1-yl)-2-(tetrahydro-pyran-4-ylamino)-benzamide,
N-[5-(2-fluoro-benzyloxy)-1H-indazol-3-yl]-4-(4-methyl-piperazin-1-yl)-2-(tetrahydro-pyran-4-ylamino)-benzamide,
N-(5-benzyloxy-1H-indazol-3-yl)-4-[(3-dimethylamino-propyl)-methyl-amino]-2-nitro-benzamide,
N-{5-[(R)-1-(3,5-difluoro-phenyl)-ethoxy]-1H-indazol-3-yl}-4-(4-methyl-piperazin-1-yl)-2-(tetrahydro-pyran-4-ylamino)-benzamide,
N-{5-[(S)-1-(3,5-difluoro-phenyl)-ethoxy]-1H-indazol-3-yl}-4-(4-methyl-piperazin-1-yl)-2-(tetrahydro-pyran-4-ylamino)-benzamide,
2-amino-N-[5-(3,5-difluoro-benzyloxy)-1H-indazol-3-yl]-4-[(3-dimethylamino-propyl)-methyl-amino]-benzamide,
N-[5-(2-chloro-5-fluoro-benzyloxy)-1H-indazol-3-yl]-4-(4-methyl-piperazin-1-yl)-2-(tetrahydro-pyran-4-ylamino)-benzamide,
N-[5-(3,5-difluoro-benzyloxy)-1H-indazol-3-yl]-4-[(3-dimethylamino-propyl)-methyl-amino]-2-(tetrahydro-pyran-4-ylamino)-benzamide,
N-[5-(3,5-difluoro-benzyloxy)-1H-indazol-3-yl]-4-[(3-dimethylamino-propyl)-methyl-amino]-2-nitro-benzamide,
N-[5-(3-chloro-5-fluoro-benzyloxy)-1H-indazol-3-yl]-4-(4-methyl-piperazin-1-yl)-2-(tetrahydro-pyran-4-ylamino)-benzamide,
N-[5-(3-fluoro-5-methyl-benzyloxy)-1H-indazol-3-yl]-4-(4-methyl-piperazin-1-yl)-2-(tetrahydro-pyran-4-ylamino)-benzamide,
N-[5-(5-fluoro-2-methyl-benzyloxy)-1H-indazol-3-yl]-4-(4-methyl-piperazin-1-yl)-2-(tetrahydro-pyran-4-ylamino)-benzamide,
1H-pyrrole-2-carboxylic acid {2-[5-(3,5-difluoro-benzyloxy)-1H-indazol-3-ylcarbamoyl]-5-[(3-dimethylamino-propyl)-methyl-amino]-phenyl}-amide,
N-[5-(2-methoxy-benzyloxy)-1H-indazol-3-yl]-4-(4-methyl-piperazin-1-yl)-2-(tetrahydro-pyran-4-ylamino)-benzamide,
2-amino-N-(5-benzyloxy-1H-indazol-3-yl)-4-[(3-dimethylamino-propyl)-methyl-amino]-benzamide,
N-[5-(4-fluoro-benzyloxy)-1H-indazol-3-yl]-4-(4-methyl-piperazin-1-yl)-2-(tetrahydro-pyran-4-ylamino)-benzamide,
N-(5-benzyloxy-1H-indazol-3-yl)-4-(4-methyl-piperazin-1-yl)-2-nitro-benzamide,
N-[5-(3,5-difluoro-benzyloxy)-1H-indazol-3-yl]-4-(4-methyl-piperazin-1-yl)-2-nitro-benzamide,
N-[5-(3,5-difluoro-benzyloxy)-1H-indazol-3-yl]-2-(3-methoxy-propylamino)-4-(4-methyl-piperazin-1-yl)-benzamide,
N-[5-(3,5-difluoro-benzyloxy)-1H-indazol-3-yl]-2-((R)-2-methoxy-1-methyl-ethylamino)-4-(4-methyl-piperazin-1-yl)-benzamide,
N-[5-(3,5-difluoro-benzyloxy)-1H-indazol-3-yl]-2-fluoro-4-(4-methyl-piperazin-1-yl)-benzamide,
N-[5-(3,5-difluoro-benzyloxy)-1H-indazol-3-yl]-2-(2-methoxy-1,1-dimethyl-ethylamino)-4-(4-methyl-piperazin-1-yl)-benzamide,
4-[2-[5-(3,5-difluoro-benzyloxy)-1H-indazol-3-ylcarbamoyl]-5-(4-methyl-piperazin-1-yl)-phenylamino]-piperidine-1-carboxylic acid ethyl ester,
N-[5-(3,5-difluoro-benzyloxy)-1H-indazol-3-yl]-2-(2-fluoro-ethylamino)-4-(4-methyl-piperazin-1-yl)-benzamide,
2-benzylamino-N-[5-(3,5-difluoro-benzyloxy)-1H-indazol-3-yl]-4-(4-methyl-piperazin-1-yl)-benzamide,
N-[5-(3,5-difluoro-benzyloxy)-1H-indazol-3-yl]-2-(1,2-dimethoxy-ethylamino)-4-(4-methyl-piperazin-1-yl)-benzamide,
4-(4-methylpiperazin-1-yl)-N-[5-[(3-phenoxybenzyl)oxy]-1H-indazol-3-yl]benzamide,
3-chloromethyl-N-[5-(3,5-difluoro-benzyloxy)-1H-indazol-3-yl]-benzamide
N-[5-(3,5-difluoro-benzyloxy)-1H-indazol-3-yl]-3-piperidin-1-ylmethyl-benzamide,
3-(azetidin-1-ylmethyl)-N-{5-[(3,5-difluorobenzyl)oxy]-1H-indazol-3-yl}benzamide,
N-{5-[(3,5-difluorobenzyl)oxy]-1H-indazol-3-yl}-3-(pyrrolidin-1-ylmethyl)benzamide,
N-{5-[(3,5-difluorobenzyl)oxy]-1H-indazol-3-yl}-3-[(2-methoxyethyl)(methyl)amino]benzamide,
N-{5-[1-(3,5-difluorophenyl)ethoxy]-1H-indazol-3-yl}-4-(4-methylpiperazin-1-yl)benzamide,
N-{5-[1-(3,5-difluorophenyl)ethoxy]-1H-indazol-3-yl}-3-(4-methylpiperazin-1-yl)benzamide,
N-{5-[(3,5-difluorobenzyl)oxy]-1H-indazol-3-yl}-3-[(1-methylpiperidin-4-yl)oxy]benzamide,
N-{5-[(3,5-difluorobenzyl)oxy]-1H-indazol-3-yl}-1-(1-methylpiperidin-4-yl)-1H-pyrazole-4-carboxamide,
N-5-[(3,5-difluorobenzyl)oxy]-1H-indazol-3-yl]-4-[(1-methylpiperidin-4-yl)oxy]benzamide,
N-[5-(benzyloxy)-1H-indazol-3-yl]-3-(4-methylpiperazin-1-yl)benzamide,
N-[5-(benzyloxy)-1H-indazol-3-yl]-1-(piperidin-4-yl)-1H-pyrazole-4-carboxamide,
N-{5-[(2-chloro-3,6-difluorobenzyl)oxy]-1H-indazol-3-yl}-3-(4-methylpiperazin-1-yl)benzamide,
N-[5-(benzyloxy)-1H-indazol-3-yl]-3-(piperazin-1-yl)benzamide,
N-[5-(benzyloxy)-1H-indazol-3-yl]-2-methyl-4-(4-methylpiperazin-1-yl)benzamide,
N-{5-[(2-chloro-3,6-difluorobenzyl)oxy]-1H-indazol-3-yl}-2-methyl-4-(4-methylpiperazin-1-yl)benzamide,
N-{5-[(3,5-difluorobenzyl)oxy]-1H-indazol-3-yl}-4-(4-methylpiperazin-1-yl)benzamide,
N-[5-(benzyloxy)-1H-indazol-3-yl]-2-methoxy-4-(4-methylpiperazin-1-yl)benzamide,
N-{5-[(2-chloro-3,6-difluorobenzyl)oxy]-1H-indazol-3-yl}-2-methoxy-4-(4-methylpiperazin-1-yl)benzamide,
N-{5-[(3,5-difluorobenzyl)oxy]-1H-indazol-3-yl}-3-(4-methylpiperazin-1-yl)benzamide, N-{5-[(3,5-difluorobenzyl)oxy]-1H-indazol-3-yl}-4-{[3-(dimethylamino)propyl](methyl)amino}benzamide,
N-{5-[(3,5-difluorobenzyl)oxy]-1H-indazol-3-yl}-4-(piperidin-1-ylmethyl)benzamide,
N-{5-[(3,5-difluorobenzyl)oxy]-1H-indazol-3-yl}-4-(morpholin-4-ylmethyl)benzamide,
N-{5-[(3,5-difluorobenzyl)oxy]-1H-indazol-3-yl}-3-[2-(dimethylamino)ethoxy]benzamide,
N-{5-[(3,5-difluorobenzyl)oxy]-1H-indazol-3-yl}-4-nitrobenzamide,
N-{5-[(3,5-difluorobenzyl)oxy]-1H-indazol-3-yl}-3-nitrobenzamide,
N-{5-[(3,5-difluorobenzyl)oxy]-1H-indazol-3-yl}-3-[(1-methylpiperidin-4-yl)amino]benzamide,
N-{5-[(3,5-difluorobenzyl)oxy]-1H-indazol-3-yl}-4-[(1-methylpiperidin-4-yl)amino]benzamide
N-{5-[(2,5-difluorobenzyl)oxy]-1H-indazol-3-yl}-4-(4-methylpiperazin-1-yl)benzamide,
N-{5-[(3,5-difluorobenzyl)oxy]-1H-indazol-3-yl}-3-(4-methylpiperazin-1-yl)benzamide,
4-(4-methylpiperazin-1-yl)-N-(5-phenoxy-1H-indazol-3-yl)benzamide,
N-[5-(3-fluorophenoxy)-1H-indazol-3-yl]-4-(4-methylpiperazin-1-yl)benzamide
N-{5-[4-(benzyloxy)phenoxy]-1H-indazol-3-yl}-4-(4-methylpiperazin-1-yl)benzamide,
4-(4-methylpiperazin-1-yl)-N-[5-(4-phenoxyphenoxy)-1H-indazol-3-yl]benzamide,
N-{5-[3-(benzyloxy)phenoxy]-1H-indazol-3-yl}-4-(4-methylpiperazin-1-yl)benzamide,
N-[5-(3,5-difluorophenoxy)-1H-indazol-3-yl]-4-(4-methylpiperazin-1-yl)benzamide,
N-[5-(3,5-difluorophenoxy)-1H-indazol-3-yl]-4-(4-methylpiperazin-1-yl)-2-(tetrahydro-2H-pyran-4-ylamino)benzamide,
N-[5-(3,5-difluorophenoxy)-1H-indazol-3-yl]-3-[(1-methylpiperidin-4-yl)oxy]benzamide,
2-methyl-4-(4-methylpiperazin-1-yl)-N-(5-phenoxy-1H-indazol-3-yl)benzamide
N-{5-(3,5-difluorophenoxy)-1H-indazol-3-yl}-1-(1-methylpiperidin-4-yl)-1H-pyrazole-4-carboxamide,
N-[5-(3,5-difluorophenoxy)-1H-indazol-3-yl]-4-[(1-methylpiperidin-4-yl)oxy]benzamide,
N-[5-(3,5-difluorophenoxy)-1H-indazol-3-yl]-3-(4-methylpiperazin-1-yl)benzamide,
N-[5-(3,5-difluorophenoxy)-1H-indazol-3-yl]-2-methyl-4-(4-methylpiperazin-1-yl)benzamide,
3-(4-methylpiperazin-1-yl)-N-(5-phenoxy-1H-indazol-3-yl)benzamide,
N-[5-(3,5-difluorophenoxy)-1H-indazol-3-yl]-2-methoxy-4-(4-methylpiperazin-1-yl)benzamide hydrochloride,
2-methoxy-4-(4-methylpiperazin-1-yl)-N-(5-phenoxy-1H-indazol-3-yl)benzamide hydrochloride,
N-[5-(3,5-difluorophenoxy)-1H-indazol-3-yl]-3-[2-(dimethylamino)ethoxy]benzamide,
N-[5-(3,5-difluorophenoxy)-1H-indazol-3-yl]-3-nitrobenzamide,
N-[5-(3,5-difluorophenoxy)-1H-indazol-3-yl]-4-nitrobenzamide,
3-amino-N-[5-(3,5-difluorophenoxy)-1H-indazol-3-yl]benzamide,
4-amino-N-[5-(3,5-difluorophenoxy)-1H-indazol-3-yl]benzamide,
N-[5-(3,5-difluorophenoxy)-1H-indazol-3-yl]-3-[(1-methylpiperidin-4-yl)amino]benzamide,
N-[5-(3,5-difluorophenoxy)-1H-indazol-3-yl]-4-[(1-methylpiperidin-4-yl)amino]benzamide,
N-[5-(3,5-difluorophenoxy)-1H-indazol-3-yl]-4-[2-(dimethylamino)ethoxy]benzamide,
N-{5-[(3,5-difluorobenzyl)oxy]-1H-indazol-3-yl}-4-amino-benzamide,
N-{5-[(3,5-difluorobenzyloxy]-1H-indazol-3-yl}-3-amino-benzamide and
4-chloromethyl-N-[5-(3,5-difluoro-benzyloxy)-1H-indazol-3-yl]-benzamide.

7. A process for preparing a compound of formula (I) as defined in claim 1, characterized in that the process comprises:
d) condensing a compound of formula (III):

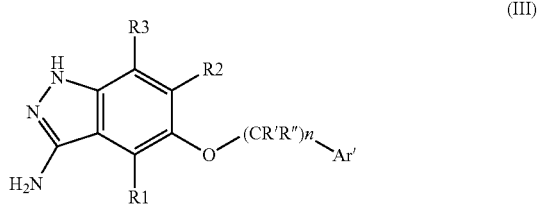

wherein n, Ar', R1, R2, R3, R' and R" are as defined in claim 1, with a compound of formula (II):

wherein Ar is as defined in claim 1 and Y represents hydroxy, or a suitable leaving group, the suitable leaving group comprising halogen, to give a compound of formula (I), as defined above, optionally separating the resultant compound into the single isomers, converting the compound of formula (I) into a different compound of formula (I), and/or into a pharmaceutically acceptable salt if desired.

8. A process for preparing a compound of formula (I) according to claim 7, characterized in that the compound of formula (III) as defined in claim 7, is prepared according to the following steps:
a) condensing a compound of formula (VI):

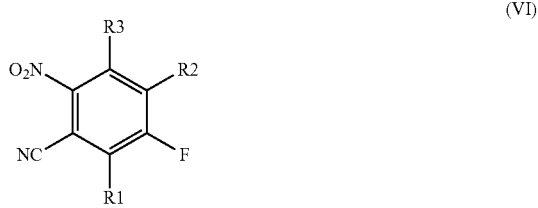

wherein R1, R2 and R3 are independently hydrogen, halogen, nitro, an optionally substituted straight or branched $C_1$-$C_6$ alkyl, NR4R5 or OR6, wherein
R4 and R5 are independently hydrogen, alkenyl, alkynyl, R8R9N—$C_7$-$C_6$ alkyl, R8O—$C_7$-$C_6$ alkyl, an optionally further substituted straight or branched $C_1$-$C_6$ alkyl, $C_3$-$C_6$ cycloalkyl, heterocyclyl, aryl or heteroaryl, or R4 and R5, taken together with the nitrogen atom to which they are bonded, may form an optionally substituted heterocyclyl group;

R6 is hydrogen, alkenyl, alkynyl, COR7, SOR10, SO$_2$R10, R8R9N—C$_1$-C$_6$ alkyl, R8O—C$_2$-C$_6$ alkyl, an optionally further substituted straight or branched C$_1$-C$_6$ alkyl, C$_3$-C$_6$ cycloalkyl, heterocyclyl, aryl or heteroaryl;

R7 is hydrogen, alkenyl, alkenyl, NR4R5, OR6, SR6, R8R9N—C$_1$-C$_6$ alkyl, R8O—C$_1$-C$_6$ alkyl, an optionally further substituted straight or branched C$_1$-C$_6$ alkyl, C$_3$-C$_6$ cycloalkyl, heterocyclyl, aryl or heteroaryl, wherein R4, R5 and R6 are defined as above;

R8 and R9 are independently hydrogen, alkenyl, alkynyl, COR7, an optionally further substituted straight or branched C$_1$-C$_6$ alkyl, C$_3$-C$_6$ cycloalkyl, heterocyclyl, aryl or heteroaryl, or R8 and R9, taken together with the nitrogen atom to which they are bonded, may form an optionally substituted heterocyclyl group, wherein R7 is as defined above;

R10 is hydrogen, alkenyl, alkynyl, NR4R5, OR6, R8R9N—C$_1$-C$_6$ alkyl, R8O—C$_1$-C$_6$ alkyl, an optionally further substituted straight or branched C$_1$-C$_6$ alkyl, C$_3$-C$_6$ cycloalkyl, heterocyclyl, aryl or heteroaryl, wherein R4, R5, R6, R8 and R9 are as defined above, with an alcohol derivative of formula (VII):

Ar'(CR'R")$_n$OH    (VII), wherein n is 0 or 1, Ar' is an optionally substituted aryl or heteroaryl, and R' and R" are each independently hydrogen or an optionally substituted straight or branched C$_1$-C$_6$ alkyl;

b) reducing the nitro group of the resultant compound of formula (V):

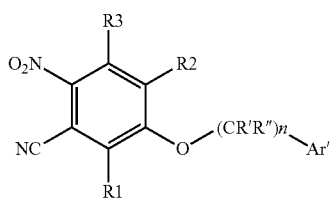

(V)

wherein n, Ar', R', R", R1, R2 and R3 are as defined above;

c) reducing the cyano group of the resultant compound of formula (IV):

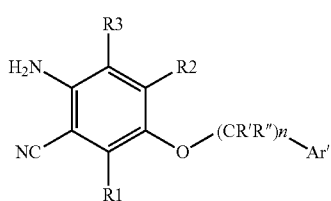

(IV)

wherein n, Ar', R', R", R1, R2 and R3 are as defined above, in the presence of a suitable reagent system, the suitable reagent system comprising at least one of NaNO$_2$/HCl and SnCl$_2$, to give a compound of formula (III) as defined above.

9. A process for preparing a compound of formula (I) according to claim 7 characterized in that the optional conversion of a compound of formula (I) into another compound of formula (I), is carried out by one or more of the following reactions:

1) reducing a compound of formula (I) wherein Ar is a substituted aryl and one of the substituents is NO$_2$, for obtaining a compound of formula (I) wherein such substituent is NH$_2$;

2) acylating a compound of formula (I) wherein Ar is a substituted aryl and one of the substituents is NH$_2$, by reaction with an acylating agent of formula (VIII) or (IX):

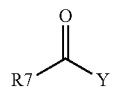

(VIII)

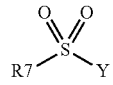

(IX)

wherein R7 is hydrogen, alkenyl, alkynyl, NR4R5, OR6, SR6, R8R9N—C$_1$-C$_6$ alkyl, R8O—C$_1$-C$_6$ alkyl, an optionally further substituted straight or branched C$_1$-C$_6$ alkyl, C$_3$-C$_6$ cycloalkyl, heterocyclyl, aryl or heteroaryl, wherein R4, R5 and R6 are defined below; R4 and R5 are independently hydrogen, alkenyl, alkynyl, R8R9N—C$_2$-C$_6$ alkyl, R8O—C$_2$-C$_6$ alkyl, an optionally further substituted straight or branched C$_1$-C$_6$ alkyl, C$_3$-C$_6$ cycloalkyl, heterocyclyl, aryl or heteroaryl, or R4 and R5, taken together with the nitrogen atom to which they are bonded, may form an optionally substituted heterocyclyl group; R6 is hydrogen, alkenyl, alkynyl, COR7, SOR10, SO$_2$R10, R8R9N—C$_1$-C$_6$ alkyl, R8O—C$_2$-C$_6$ alkyl, an optionally further substituted straight or branched C$_1$-C$_6$ alkyl, C$_3$-C$_6$ cycloalkyl, heterocyclyl, aryl or heteroaryl;

and Y is hydroxy, or a suitable leaving group, the suitable leaving group comprising halogen, for obtaining a compound of formula (I) wherein such substituent is a NHCOR7 or NHSO$_2$R7 residue, wherein R7 is as defined above;

3) reacting a compound of formula (I) wherein Ar is a substituted aryl and one of the substituents is NH$_2$, with a suitable aldehyde or ketone in the presence of a reducing agent, for obtaining a compound of formula (I) wherein such substituent is a NR4R5 group, wherein one of the R4 or R5 is hydrogen and the other is an optionally further substituted straight or branched C$_1$-C$_6$ alkyl, C$_3$-C$_6$ cycloalkyl, heterocyclyl, aryl, heteroaryl, R8R9N—C$_2$-C$_6$ alkyl or R8O—C$_2$-C$_6$ alkyl, wherein R8 and R9 are independently hydrogen, alkenyl, alkynyl, COR7, an optionally further substituted straight or branched C$_1$-C$_6$ alkyl, C$_3$-C$_6$ cycloalkyl, heterocyclyl, aryl or heteroaryl, or R8 and R9, taken together with the nitrogen atom to which they are bonded, may form an optionally substituted heterocyclyl group, wherein R7 is as defined above;

4) converting a compound of formula (I) wherein n is 1, into another compound of formula (I) with a different Ar' group by a multi-step process consisiting in:

4A) protecting a compound of formula (I);
4B) reducing the resultant compound of formula (Xa):

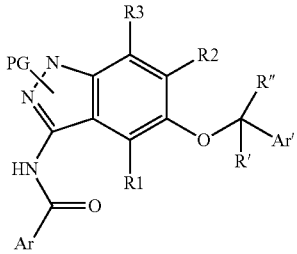

(Xa)

wherein Ar is aryl or heteroaryl substituted with Ra and Rb, wherein
Ra is $NO_2$, NH, NH-G, N-(E)-G, O-G', $(CH_2)_n$-A or $CH_2$-Hal and
Rb is hydrogen, halogen, $NO_2$, $NH_2$, NH-G, NH—CO-L, O-E or E, wherein
Hal is halogen,
A is optionally substituted heterocyclyl,
E is straight or branched unsubstituted $C_1$-$C_6$ alkyl,
G is straight or branched substituted $C_1$-$C_6$ alkyl or an optionally substituted heterocyclyl,
G' is straight or branched $C_1$-$C_6$ alkyl substituted with $N(C_1$-$C_6alkyl)_2$ or an optionally substituted heterocyclyl, and
L is optionally substituted heteroaryl,
Ar' is an optionally substituted aryl or heteroaryl, R' and R" are each independently hydrogen or an optionally substituted straight or branched $C_1$-$C_6$ alkyl, R1, R2 and R3 are independently hydrogen, halogen, nitro, an optionally substituted straight or branched $C_1$-$C_6$ alkyl, NR4R5 or OR6, wherein R10 is hydrogen, alkenyl, alkynyl, NR4R5, OR6, R8R9N—$C_1$-$C_6$ alkyl, R8O—$C_1$-$C_6$ alkyl, an optionally further substituted straight or branched $C_1$-$C_6$ alkyl, $C_3$-$C_6$ cycloalkyl, heterocyclyl, aryl or heteroaryl, wherein R4, R5, R6, R8 and R9 are as defined above and PG is a suitable protecting group, the suitable protecting group comprising at least one of ethoxycarbonyl, methoxycarbonyl, tert-butoxycarbonyl and trifluoroacetyl;
4C) coupling the resultant compound of formula (XI):

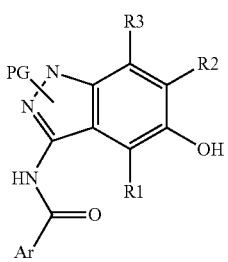

(XI)

wherein Ar, R1, R2, R3 and PG are as defined above, with a compound of formula (XII)

Ar'(CR'R")W          (XII)

wherein Ar', R' and R" are as defined above but Ar' is different from Ar' of formula (Xa), and W represents a halogen atom, such as chlorine, bromine or iodine, or a suitable leaving group, the suitable leaving group comprising at least one of hydroxy-group and sulphonates, such as p-toulenesulphonate, methanesulphonate or trifluoromethanesulphonate;
4D) removing the protecting group from the resultant compound of formula (X):

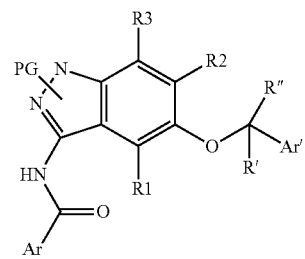

(X)

wherein Ar, Ar', R', R", R1, R2, R3 and PG are as defined above, to give a compound of formula (I) wherein n is 1 and Ar, Ar', R1, R2, R3, R' and R" are as defined above but Ar' is different from Ar' of formula (Xa).

10. A method for treating a disease, the disease selected from the group consisting of lung cancer, colon cancer, lymphoma, and leukaemia, the method comprising administering to a mammal in need thereof an effective amount of a compound of formula (I) as defined in claim 1.

11. An in-vitro method for inhibiting ALK activity which comprises contacting the said receptor with an effective amount of a compound as defined in claim 1.

12. A pharmaceutical composition comprising a therapeutically effective amount of a compound of formula (I) or a pharmaceutically acceptable salt thereof, as defined in claim 1, and at least one pharmaceutically acceptable excipient, carrier and/or diluent.

13. A product or kit comprising a compound of formula (I) or a pharmaceutically acceptable salt thereof, as defined in claim 1, or pharmaceutical compositions thereof comprising a therapeutically effective amount of a compound of formula (I) or a pharmaceutically acceptable salt thereof, as defined in claim 1, and at least one pharmaceutically acceptable excipient, carrier and/or diluent, and one or more chemotherapeutic agents, as a combined preparation for simultaneous, separate or sequential use in anticancer therapy.

14. A compound of formula (I) or a pharmaceutically acceptable salt thereof, as defined in claim 1, for use as a medicament.

* * * * *